(12) United States Patent
Tassi et al.

(10) Patent No.: US 11,470,827 B2
(45) Date of Patent: Oct. 18, 2022

(54) TRANSGENIC MICE EXPRESSING HUMAN TREM PROTEINS AND METHODS OF USE THEREOF

(71) Applicant: Alector LLC, South San Francisco, CA (US)

(72) Inventors: Ilaria Tassi, San Francisco, CA (US); Asa Abeliovich, New York, NY (US); Seung-Joo Lee, Benicia, CA (US); Arnon Rosenthal, Woodside, CA (US); Tina Schwabe, San Francisco, CA (US)

(73) Assignee: Alector LLC, South San Francisco, CA (US)

( * ) Notice: Subject to any disclaimer, the term of this patent is extended or adjusted under 35 U.S.C. 154(b) by 0 days.

(21) Appl. No.: 16/218,299

(22) Filed: Dec. 12, 2018

(65) Prior Publication Data

US 2019/0174730 A1 Jun. 13, 2019

Related U.S. Application Data

(60) Provisional application No. 62/597,750, filed on Dec. 12, 2017.

(51) Int. Cl.
*A01K 67/027* (2006.01)
*C07H 21/04* (2006.01)
*C07K 14/705* (2006.01)
*A61K 49/00* (2006.01)

(52) U.S. Cl.
CPC ...... *A01K 67/0278* (2013.01); *A61K 49/0008* (2013.01); *C07K 14/70503* (2013.01); *A01K 2207/15* (2013.01); *A01K 2227/105* (2013.01); *A01K 2267/0312* (2013.01); *A01K 2267/0318* (2013.01); *A01K 2267/0325* (2013.01)

(58) Field of Classification Search
CPC ............ A01K 67/0278; A01K 2207/15; A01K 2217/052; A01K 2227/105; C07H 21/04
See application file for complete search history.

(56) References Cited

U.S. PATENT DOCUMENTS

| 4,469,863 | A | 9/1984 | Ts'o et al. |
|---|---|---|---|
| 4,873,191 | A | 10/1989 | Wagner et al. |
| 5,175,384 | A | 12/1992 | Krimpenfort et al. |
| 5,536,821 | A | 7/1996 | Agrawal et al. |
| 5,541,306 | A | 7/1996 | Agrawal et al. |
| 5,602,229 | A | 2/1997 | Malabarba et al. |
| 5,614,622 | A | 3/1997 | Iyer et al. |
| 5,637,683 | A | 6/1997 | Usher et al. |
| 5,637,684 | A | 6/1997 | Cook et al. |
| 5,700,922 | A | 12/1997 | Cook |
| 5,717,083 | A | 2/1998 | Cook et al. |
| 5,719,262 | A | 2/1998 | Buchardt et al. |
| 5,739,308 | A | 4/1998 | Kandimalla et al. |
| 5,739,314 | A | 4/1998 | Roy et al. |
| 5,773,601 | A | 6/1998 | Agrawal |
| 5,886,165 | A | 3/1999 | Kandimalla et al. |
| 5,929,226 | A | 7/1999 | Padmapriya et al. |
| 5,955,599 | A | 9/1999 | Iyer et al. |
| 5,962,674 | A | 10/1999 | Iyer et al. |
| 5,977,296 | A | 11/1999 | Nielsen et al. |
| 6,037,521 | A | 3/2000 | Sato et al. |
| 6,066,778 | A | 5/2000 | Ginsburg et al. |
| 6,117,992 | A | 9/2000 | Iyer |
| 6,140,482 | A | 10/2000 | Iyer et al. |
| 6,455,308 | B1 | 9/2002 | Freier |

FOREIGN PATENT DOCUMENTS

| WO | WO-1995/02697 A1 | 1/1995 |
|---|---|---|
| WO | WO-1999/32619 A1 | 7/1999 |
| WO | WO-2000/44895 A1 | 8/2000 |
| WO | WO-2000/56746 A2 | 9/2000 |
| WO | WO-2000/75372 A1 | 12/2000 |
| WO | WO-2001/14398 A1 | 3/2001 |
| WO | WO-2001/29058 A1 | 4/2001 |
| WO | WO-2001/36646 A1 | 5/2001 |

OTHER PUBLICATIONS

Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*
Maksimenko et al., 2013, Acta Naturae, vol. 5, No. 1, p. 33-46.*
Yang et al., 2016, PNAS, 113(41), E6209-E6218, p. 1-10.*
Guo et al., 2015, Cell Research, vol. 25, p. 767-768.*
Lee et al., 2016, Drug Discovery Today: Disease Models, vol. 20, p. 13-20.*
Kang et al., 2018, Human Molecular Genetics, vol. 27, No. 2, p. 211-223.*
Beattie, M.S. et al. (Oct. 24, 2002). "ProNGF Induces p75-Mediated Death of Oligodendrocytes following Spinal Cord Injury," *Neuron* 36(3):375-386.
Blesa, J. et al. (Dec. 15, 2014). "Parkinson's Disease: Animal Models and Dopaminergic Cell Vulnerability," *Front. Neuroanat.* 8(Article155):1-12.

(Continued)

*Primary Examiner* — Shin Lin Chen
(74) *Attorney, Agent, or Firm* — Morrison & Foerster LLP

(57) ABSTRACT

Provided herein are transgenic non-human animals whose genomes comprise two or more human genes selected from TREM1, TREML1, TREM2, TREML2, and TREML4, to methods of screening candidate agents that bind to and/or modulate the function and/or activity of at least one of the human genes in the transgenic non-human animals, and to methods of screening candidate agents to determine their effect on one or more activities and/or functions associated with expression of at least one of the human genes in the transgenic non-human animals. Further provided herein are methods of recapitulating a human TREM immune system in a non-human animal, and methods of generating a non-human animal disease model comprising a human TREM repertoire.

10 Claims, 14 Drawing Sheets
(6 of 14 Drawing Sheet(s) Filed in Color)
Specification includes a Sequence Listing.

(56) References Cited

OTHER PUBLICATIONS

Bouchon, A. et al. (2001). "A DAP12-Mediated Pathway Regulates Expression of CC Chemokine Receptor 7 and Maturation of Human Dendritic Cells," *J. Exp. Med.* 194(8):1111-1122.

Bradley, A. et al. (May 17, 1984). "Formation of Germ-Line Chimaeras From Embryo-Derived Teratocarcinoma Cell Lines," *Nature* 309(5965):255-256.

Cruts, M. et al. (2008; e-pub. Mar. 6, 2008). "Loss of Progranulin Function in Frontotemporal Lobar Degeneration," *Trends Genetics* 24(4):186-194.

Evans, M.J. et al. (Jul. 9, 1981). "Establishment in Culture of Pluripotential Cells From Mouse Embryos," *Nature* 292:154-156.

Gordon, J.W. yet al. (Dec. 1980). "Genetic Transformation of Mouse Embryos by Microinjection of Purified DNA," *PNAS* 77(12):7380-7384.

Gossler, A. et al. (Dec. 1986). "Transgenesis by Means of Blastocyst-Derived Embryonic Stem Cell Lines," *PNAS* 83:9065-9069.

Götz, J. et al. (2009). "Animal Models for Alzheimer's Disease and Frontotemporal Dementia: A Perspective," *ASN Neuro.* 1(4):251-264.

Götz, J. et al. (Jul. 2008). "Animal Models of Alzheimer's Disease and Frontotemporal Dementia," *Nat Rev Neurosci.* 9(7):532-544.

Harrington, A.W. et al. (Apr. 20, 2004). "Secreted proNGF is a Pathophysiological Death-Inducing Ligand After Adult CNS Injury," *Proc. Natl. Acad. Sci USA* 101(16):6226-6230.

Hutton, M. et al. (Jun. 18, 1998). "Association of Missense and 5'-Splice-Site Mutations in Tau with the Inherited Dementia FTDP-17," *Nature* 393(6689):702-705.

Jaenisch, R. (Jun. 10, 1988). "Transgenic Animals," *Science* 240(4858):1468-1474.

Kaifu, T. et al. (Feb. 1, 2003). "Osteopetrosis and Thalamic Hypomyelinosis with Synaptic Degeneration in DAP12-deficient Mice," *J Clin. Invest.* 111(3): 323-332.

Koson, P. et al. (Jul. 2008). "Truncated Tau Expression Levels Determine Life Span of a Rat Model of Tauopathy Without Causing Neuronal Loss or Correlating With Terminal Neurofibrillary Tangle Load," *Eur. J Neurosci.* 28(2): 239-246.

Laird, A.S. et al. (Oct. 13, 2010). "Progranulin is Neurotrophic in Vivo and Protects against a Mutant TDP-43 Induced Axonopathy," *PLOS ONE* 5(10):e13368, seven pages.

Lavitrano, M. et al. (Jun. 2, 1989). "Sperm Cells as Vectors for Introducing Foreign DNA into Eggs: Genetic Transformation of Mice," *Cell* 57(5):717-723.

Lo, C.W. (Oct. 1983). "Transformation by Iontophoretic Microinjection of DNA: Multiple Integrations Without Tandem Insertions," *Mol. Cell. Biol.* 3(10):1803-1814.

Luk, K.C. et al. (Nov. 16, 2012). "Pathological α-Synuclein Transmission Initiates Parkinson-like Neurodegeneration in Non-transgenic Mice," *Science* 338(6109):949-953, 9 pages.

Neary, D. et al. (Dec. 1998). "Frontotemporal Lobar Degeneration: A Consensus on Clinical Diagnostic Criteria," *Neurology* 51:1546-1554.

Neumann, M. et al. (Oct. 2007). "TDP-43 Proteinopathy in Frontotemporal Lobar Degeneration and Amyotrophic Lateral Sclerosis Protein Misfolding Diseases Without Amyloidosis," *Arch. Neurol.* 64(10):1388-1394.

Peng, Q. et al. (May 18, 2010). "TREM2- and DAP12-Dependent Activation of PI3K Requires DAP10 and Is Inhibited by SHIP1," *Science Signaling* 3(122):1-15.

Philips, T. et al. (Jun. 1, 2015). "Rodent Models of Amyotrophic Lateral Sclerosis," *Curr. Protoc. Pharmacol.* 69:5.67.1-5.67.21, 26 pages.

Ramaswamy, S. et al. (Jan. 2007). "Animal Models of Huntington's Disease," *ILAR J* 48(4):356-373.

Ratnavalli, E. et al. (June (1 of 2) 2002). "The Prevalence of Frontotemporal Dementia," *Neurology* 58:1615-1621.

Robertson, E. et al. (Oct. 2, 1986). "Germ-Line Transmission of Genes Introduced Into Cultured Pluripotential Cells by Retroviral Vector," *Nature* 323(6087):445-448.

Schymick, J.C. et al. (2007). "Progranulin Mutations and Amyotrophic Lateral Sclerosis or Amyotrophic Lateral Sclerosis—Frontotemporal Dementia Phenotypes," *Journal of Neurology Neurosurgery and Psychiatry* 78:754-756.

Thompson, S. et al. (Jan. 27, 1989). "Germ Line Transmission and Expression of a Corrected HPRT Gene Produced by Gene Targeting in Embryonic Stem Cells," *Cell* 56(2):313-321.

Van Der Putten, H. et al. (Sep. 1985). "Efficient Insertion of Genes Into the Mouse Germ Line Via Retroviral Vectors," *PNAS* 82:6148-6152.

Whittaker, G.C. et al. (Jan. 29, 2010; e-pub. Nov. 30, 2009). "The Linker for Activation of B Cells (LAB)/Non-T Cell Activation Linker (NTAL) Regulates Triggering Receptor Expressed on Myeloid Cells (TREM)-2 Signaling and Macrophage Inflammatory Responses Independently of the Linker for Activation of T Cells," *The Journal of Biological Chemistry* 285(5):2976-2985.

Carrasquillo et al., (2017). "A candidate regulatory variant at the TREM gene cluster associates with decreased Alzheimer's disease risk, and increased TREML1 and TREM2 brain gene expression," Alzheimers Dement., 13(6):663-673, 37 pages.

Colonna, (2003). "TREMS in the Immune System and Beyond," The Journal of Immunology, 3(6):445-453.

Derive et al., (2012). "Soluble TREM-like transcript-1 regulates leukocyte activation and controls microbial sepsis," Journal of immunology, 188:5585-92.

Guerreiro et al., (2013). "TREM2 variants in Alzheimer's disease," N Engl J Med., 368(2):117-27.

Hickman et al., (2014). "TREM2 and the neuroimmunology of Alzheimer's disease," Biochem Pharmacol., 88(4):495-498, 9 pages.

Hsieh et al., (2009). "A role for TREM2 ligands in the phagocytosis of apoptotic neuronal cells by microglia," J Neurochem., 109(4):1144-56.

Jay et al., (2014). "TREM2 in Neurodegenerative Diseases," Mol Neurodegener., 2;12(1):56, 33 pages.

Lue et al., (2015) "TREM2 Protein Expression Changes Correlate with Alzheimer's Disease Neurodegenerative Pathologies in Post-Mortem Temporal Cortices," Brain Pathol., 25(4):469-80.

Paloneva et al., (2002). "Mutations in two genes encoding different subunits of a receptor signaling complex result in an identical disease phenotype," Am J Hum Genet., 71(3):656-62.

Pelham et al., (2014) "Triggering receptor expressed on myeloid cells receptor family modulators: a patent review," Expert Opin Ther Pat., 24(12):1383-95, 22 pages.

Sessa et al., (2004). "Distribution and signaling of TREM2/DAP12, the receptor system mutated in human polycystic lipomembraneous osteodysplasia with sclerosing leukoencephalopathy dementia," European Journal of Neuroscience, 20(10):2617-2628.

Takahashi et al., (2005). "Clearance of Apoptotic Neurons Without Inflammation by Microglial Triggering Receptor Expressed on Myeloid Cells-2," Journal of Experimental Medicine, 201(4):647-657.

Washington et al., (2002). "Initial characterization of TREM-like transcript (TLT)-1: a putative inhibitory receptor within the TREM cluster," Blood, 100 (10):3822-3824.

Washington et al., (2004) "A TREM family member, TLT-1, is found exclusively in the alpha-granules of megakaryocytes and platelets," Blood, 104(4):1042-7.

Yoon et al., (2012). "TLT-1s, Alternative Transcripts of Triggering Receptor Expressed on Myeloid Cell-like Transcript-1 (TLT-1), Inhibits the Triggering Receptor Expressed on Myeloid Cell-2 (TREM-2)-mediated Signaling Pathway during Osteoclastogenesis," The Journal of Biological Chemistry, 287(35):29620-29626.

Zhang et al., (2004). "An RNA-sequencing transcriptome and splicing database of glia, neurons, and vascular cells of the cerebral cortex," J Neurosci., 34(36):11929-47.

Zhou et al., (2020). "Human and mouse single-nucleus transcriptomics reveal TREM2-dependent and TREM2-independent cellular responses in Alzheimer's disease," Nature medicine, 26(1):131-142, 54 pages.

* cited by examiner

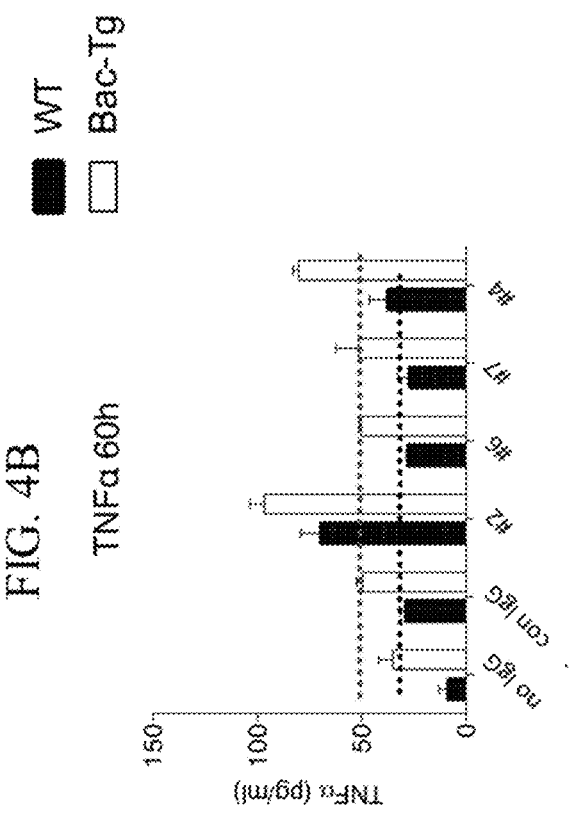
FIG. 4A  FIG. 4B  FIG. 4C  FIG. 4D

SEQUENCE LISTING

<160> NUMBER OF SEQ ID NOS: 12

<210> SEQ ID NO 1
<211> LENGTH: 234
<212> TYPE: PRT
<213> ORGANISM: Homo sapiens

<400> SEQUENCE: 1

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230

<210> SEQ ID NO 2
<211> LENGTH: 150
<212> TYPE: PRT
<213> ORGANISM: Homo sapiens

```
<400> SEQUENCE: 2

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Arg Cys Ser Thr Leu Ser Phe
    130                 135                 140

Ser Trp Leu Val Asp Ser
145                 150

<210> SEQ ID NO 3
<211> LENGTH: 225
<212> TYPE: PRT
<213> ORGANISM: Homo sapiens

<400> SEQUENCE: 3

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Tyr Ser Phe Gln Val Pro Gly Pro
        195                 200                 205
```

```
Leu Val Trp Thr Leu Ser Pro Leu Phe Pro Ser Leu Cys Ala Glu Arg
            210                 215                 220

Met
225

<210> SEQ ID NO 4
<211> LENGTH: 311
<212> TYPE: PRT
<213> ORGANISM: Homo sapiens

<400> SEQUENCE: 4

Met Gly Leu Thr Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
        35                  40                  45

Lys Val Trp Cys Arg Phe Leu Pro Glu Gly Cys Gln Pro Leu Val Ser
    50                  55                  60

Ser Ala Val Asp Arg Arg Ala Pro Ala Gly Arg Arg Thr Phe Leu Thr
65                  70                  75                  80

Asp Leu Gly Gly Gly Leu Leu Gln Val Glu Met Val Thr Leu Gln Glu
                85                  90                  95

Glu Asp Ala Gly Glu Tyr Gly Cys Met Val Asp Gly Ala Arg Gly Pro
            100                 105                 110

Gln Ile Leu His Arg Val Ser Leu Asn Ile Leu Pro Pro Glu Glu Glu
        115                 120                 125

Glu Glu Thr His Lys Ile Gly Ser Leu Ala Glu Asn Ala Phe Ser Asp
    130                 135                 140

Pro Ala Gly Ser Ala Asn Pro Leu Glu Pro Ser Gln Asp Glu Lys Ser
145                 150                 155                 160

Ile Pro Leu Ile Trp Gly Ala Val Leu Leu Val Gly Leu Leu Val Ala
                165                 170                 175

Ala Val Val Leu Phe Ala Val Met Ala Lys Arg Lys Gln Gly Asn Arg
            180                 185                 190

Leu Gly Val Cys Gly Arg Phe Leu Ser Ser Arg Val Ser Gly Met Asn
        195                 200                 205

Pro Ser Ser Val Val His His Val Ser Asp Ser Gly Pro Ala Ala Glu
    210                 215                 220

Leu Pro Leu Asp Val Pro His Ile Arg Leu Asp Ser Pro Ser Phe
225                 230                 235                 240

Asp Asn Thr Thr Tyr Thr Ser Leu Pro Leu Asp Ser Pro Ser Gly Lys
                245                 250                 255

Pro Ser Leu Pro Ala Pro Ser Ser Leu Pro Pro Leu Pro Pro Lys Val
            260                 265                 270

Leu Val Cys Ser Lys Pro Val Thr Tyr Ala Thr Val Ile Phe Pro Gly
        275                 280                 285

Gly Asn Lys Gly Gly Gly Thr Ser Cys Gly Pro Ala Gln Asn Pro Pro
    290                 295                 300

Asn Asn Gln Thr Pro Ser Ser
305                 310

<210> SEQ ID NO 5
<211> LENGTH: 199
<212> TYPE: PRT
<213> ORGANISM: Homo sapiens
```

<400> SEQUENCE: 5

```
Met Gly Leu Thr Leu Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
            35                  40                  45

Lys Val Trp Cys Arg Phe Leu Pro Gly Cys Gln Pro Leu Val Ser
    50                  55                  60

Ser Ala Val Asp Arg Arg Ala Pro Ala Gly Arg Arg Thr Phe Leu Thr
65              70                  75                  80

Asp Leu Gly Gly Gly Leu Leu Gln Val Glu Met Val Thr Leu Gln Glu
                    85                  90                  95

Glu Asp Ala Gly Glu Tyr Gly Cys Met Val Asp Gly Ala Arg Gly Pro
                100                 105                 110

Gln Ile Leu His Arg Val Ser Leu Asn Ile Leu Pro Pro Glu Glu Glu
            115                 120                 125

Glu Glu Thr His Lys Ile Gly Ser Leu Ala Glu Asn Ala Phe Ser Asp
130                 135                 140

Pro Ala Gly Ser Ala Asn Pro Leu Glu Pro Ser Gln Asp Glu Lys Ser
145                 150                 155                 160

Ile Pro Leu Ile Trp Gly Ala Val Leu Leu Val Gly Leu Leu Val Ala
                165                 170                 175

Ala Val Val Leu Phe Ala Val Met Ala Lys Arg Lys Gln Glu Ser Leu
            180                 185                 190

Leu Ser Gly Pro Pro Arg Gln
            195
```

<210> SEQ ID NO 6
<211> LENGTH: 200
<212> TYPE: PRT
<213> ORGANISM: Homo sapiens

<400> SEQUENCE: 6

```
Met Gly Leu Thr Leu Leu Leu Leu Leu Leu Gly Leu Glu Glu Glu
1               5                   10                  15

Glu Glu Glu Thr His Lys Ile Gly Ser Leu Ala Glu Asn Ala Phe Ser
            20                  25                  30

Asp Pro Ala Gly Ser Ala Asn Pro Leu Glu Pro Ser Gln Asp Glu Lys
            35                  40                  45

Ser Ile Pro Leu Ile Trp Gly Ala Val Leu Leu Val Gly Leu Leu Val
    50                  55                  60

Ala Ala Val Val Leu Phe Ala Val Met Ala Lys Arg Lys Gln Gly Asn
65                  70                  75                  80

Arg Leu Gly Val Cys Gly Arg Phe Leu Ser Ser Arg Val Ser Gly Met
                    85                  90                  95

Asn Pro Ser Ser Val Val His His Val Ser Asp Ser Gly Pro Ala Ala
                100                 105                 110

Glu Leu Pro Leu Asp Val Pro His Ile Arg Leu Asp Ser Pro Pro Ser
            115                 120                 125

Phe Asp Asn Thr Thr Tyr Thr Ser Leu Pro Leu Asp Ser Pro Ser Gly
            130                 135                 140

Lys Pro Ser Leu Pro Ala Pro Ser Ser Leu Pro Pro Leu Pro Pro Lys
145                 150                 155                 160
```

```
Val Leu Val Cys Ser Lys Pro Val Thr Tyr Ala Thr Val Ile Phe Pro
                165                 170                 175

Gly Gly Asn Lys Gly Gly Thr Ser Cys Gly Pro Ala Gln Asn Pro
            180                 185                 190

Pro Asn Asn Gln Thr Pro Ser Ser
        195                 200
```

<210> SEQ ID NO 7
<211> LENGTH: 230
<212> TYPE: PRT
<213> ORGANISM: Homo sapiens

<400> SEQUENCE: 7

```
Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230
```

<210> SEQ ID NO 8
<211> LENGTH: 219
<212> TYPE: PRT
<213> ORGANISM: Homo sapiens

<400> SEQUENCE: 8

```
Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45
```

```
Ala Trp Cys Arg Gln Leu Gly Glu Lys Gly Pro Cys Gln Arg Val Val
 50                  55                  60

Ser Thr His Asn Leu Trp Leu Leu Ser Phe Leu Arg Arg Trp Asn Gly
 65                  70                  75                  80

Ser Thr Ala Ile Thr Asp Asp Thr Leu Gly Gly Thr Leu Thr Ile Thr
                 85                  90                  95

Leu Arg Asn Leu Gln Pro His Asp Ala Gly Leu Tyr Gln Cys Gln Ser
                100                 105                 110

Leu His Gly Ser Glu Ala Asp Thr Leu Arg Lys Val Leu Val Glu Val
                115                 120                 125

Leu Ala Asp Pro Leu Asp His Arg Asp Ala Gly Asp Leu Trp Phe Pro
130                 135                 140

Gly Glu Ser Glu Ser Phe Glu Asp Ala His Val Glu His Ser Ile Ser
145                 150                 155                 160

Arg Ala Glu Arg His Val Lys Glu Asp Asp Gly Arg Lys Ser Pro Gly
                165                 170                 175

Glu Val Pro Pro Gly Thr Ser Pro Ala Cys Ile Leu Ala Thr Trp Pro
                180                 185                 190

Pro Gly Leu Leu Val Leu Leu Trp Gln Glu Thr Thr Leu Pro Glu His
                195                 200                 205

Cys Phe Ser Trp Thr Leu Glu Ala Gly Thr Gly
                210                 215

<210> SEQ ID NO 9
<211> LENGTH: 222
<212> TYPE: PRT
<213> ORGANISM: Homo sapiens

<400> SEQUENCE: 9

Met Glu Pro Leu Arg Leu Leu Ile Leu Leu Phe Val Thr Glu Leu Ser
 1               5                  10                  15

Gly Ala His Asn Thr Thr Val Phe Gln Gly Val Ala Gly Gln Ser Leu
                 20                  25                  30

Gln Val Ser Cys Pro Tyr Asp Ser Met Lys His Trp Gly Arg Arg Lys
             35                  40                  45

Ala Trp Cys Arg Gln Leu Gly Glu Lys Gly Pro Cys Gln Arg Val Val
 50                  55                  60

Ser Thr His Asn Leu Trp Leu Leu Ser Phe Leu Arg Arg Trp Asn Gly
 65                  70                  75                  80

Ser Thr Ala Ile Thr Asp Asp Thr Leu Gly Gly Thr Leu Thr Ile Thr
                 85                  90                  95

Leu Arg Asn Leu Gln Pro His Asp Ala Gly Leu Tyr Gln Cys Gln Ser
                100                 105                 110

Leu His Gly Ser Glu Ala Asp Thr Leu Arg Lys Val Leu Val Glu Val
                115                 120                 125

Leu Ala Asp Pro Leu Asp His Arg Asp Ala Gly Asp Leu Trp Phe Pro
130                 135                 140

Gly Glu Ser Glu Ser Phe Glu Asp Ala His Val Glu His Ser Ile Ser
145                 150                 155                 160

Arg Pro Ser Gln Gly Ser His Leu Pro Ser Cys Leu Ser Lys Glu Pro
                165                 170                 175

Leu Gly Arg Arg Asn Pro Leu Pro Thr His Phe His Pro Ser Pro Pro
                180                 185                 190
```

```
Gly Leu His Leu Ser His Gln Asp Ser Ser Gln Arg Pro Leu Gly
        195                 200                 205

Cys Ser Leu Ala Trp Thr Glu Ala Arg Asp Thr Ser Thr Gln
    210                 215                 220

<210> SEQ ID NO 10
<211> LENGTH: 321
<212> TYPE: PRT
<213> ORGANISM: Homo sapiens

<400> SEQUENCE: 10

Met Ala Pro Ala Phe Leu Leu Leu Leu Leu Trp Pro Gln Gly Cys
1               5                   10                  15

Val Ser Gly Pro Ser Ala Asp Ser Val Tyr Thr Lys Val Arg Leu Leu
                20                  25                  30

Glu Gly Glu Thr Leu Ser Val Gln Cys Ser Tyr Lys Gly Tyr Lys Asn
            35                  40                  45

Arg Val Glu Gly Lys Val Trp Cys Lys Ile Arg Lys Lys Lys Cys Glu
    50                  55                  60

Pro Gly Phe Ala Arg Val Trp Val Lys Gly Pro Arg Tyr Leu Leu Gln
65                  70                  75                  80

Asp Asp Ala Gln Ala Lys Val Val Asn Ile Thr Met Val Ala Leu Lys
                85                  90                  95

Leu Gln Asp Ser Gly Arg Tyr Trp Cys Met Arg Asn Thr Ser Gly Ile
            100                 105                 110

Leu Tyr Pro Leu Met Gly Phe Gln Leu Asp Val Ser Pro Ala Pro Gln
        115                 120                 125

Thr Glu Arg Asn Ile Pro Phe Thr His Leu Asp Asn Ile Leu Lys Ser
    130                 135                 140

Gly Thr Val Thr Thr Gly Gln Ala Pro Thr Ser Gly Pro Asp Ala Pro
145                 150                 155                 160

Phe Thr Thr Gly Val Met Val Phe Thr Pro Gly Leu Ile Thr Leu Pro
                165                 170                 175

Arg Leu Leu Ala Ser Thr Arg Pro Ala Ser Lys Thr Gly Tyr Ser Phe
            180                 185                 190

Thr Ala Thr Ser Thr Thr Ser Gln Gly Pro Arg Arg Thr Met Gly Ser
        195                 200                 205

Gln Thr Val Thr Ala Ser Pro Ser Asn Ala Arg Asp Ser Ser Ala Gly
    210                 215                 220

Pro Glu Ser Ile Ser Thr Lys Ser Gly Asp Leu Ser Thr Arg Ser Pro
225                 230                 235                 240

Thr Thr Gly Leu Cys Leu Thr Ser Arg Ser Leu Leu Asn Arg Leu Pro
                245                 250                 255

Ser Met Pro Ser Ile Arg His Gln Asp Val Tyr Ser Thr Val Leu Gly
            260                 265                 270

Val Val Leu Thr Leu Leu Val Leu Met Leu Ile Met Val Tyr Gly Phe
        275                 280                 285

Trp Lys Lys Arg His Met Ala Ser Tyr Ser Met Cys Ser Asp Pro Ser
    290                 295                 300

Thr Arg Asp Pro Pro Gly Arg Pro Glu Pro Tyr Val Glu Val Tyr Leu
305                 310                 315                 320

Ile
```

```
<210> SEQ ID NO 11
<211> LENGTH: 200
<212> TYPE: PRT
<213> ORGANISM: Homo sapiens

<400> SEQUENCE: 11

Met Ala Trp Gly Gly Val His Thr Cys Cys Phe His Leu Cys Cys Cys
1               5                   10                  15

Cys Ser Trp Pro Gln Gly Ala Val Pro Glu Glu Leu His Lys His Pro
            20                  25                  30

Gly Gln Thr Leu Leu Leu Gln Cys Gln Tyr Ser Pro Lys Arg Gly Pro
        35                  40                  45

Tyr Gln Pro Lys Ser Trp Cys Gln Gln Thr Ser Pro Ser Arg Cys Thr
50                  55                  60

Leu Leu Val Thr Ser Ser Lys Pro Trp Thr Ala Val Gln Lys Ser His
65                  70                  75                  80

Tyr Thr Ile Trp Asp Lys Pro Asn Ala Gly Phe Phe Asn Ile Thr Met
                85                  90                  95

Ile Gln Leu Thr Gln Asn Asp Ser Gly Phe Tyr Trp Cys Gly Ile Tyr
            100                 105                 110

Asn Ala Ser Glu Asn Ile Ile Thr Val Leu Arg Asn Ile Ser Leu Val
        115                 120                 125

Val Ser Pro Ala Pro Thr Thr Ser Pro Met Trp Thr Leu Pro Trp Leu
130                 135                 140

Pro Thr Ser Thr Val Leu Ile Thr Ser Pro Glu Gly Thr Ser Gly His
145                 150                 155                 160

Pro Ser Ile Asn Gly Ser Glu Thr Arg Lys Ser Arg Ala Pro Ala Cys
                165                 170                 175

Leu Gly Ser Gly Gly Pro Arg Phe Leu Val Leu Val Leu Cys Gly Leu
            180                 185                 190

Leu Leu Ala Lys Gly Leu Met Leu
        195                 200

<210> SEQ ID NO 12
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2, 3
<223> OTHER INFORMATION: Xaa = Any Amino Acid and up to 2 of them can be
      present or absent
<220> FEATURE:
<221> NAME/KEY: VARIANT
<222> LOCATION: 5, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Leu or Ile
<220> FEATURE:
<221> NAME/KEY: VARIANT
<222> LOCATION: 8, 9, 10, 11, 12, 13, 14, 15
<223> OTHER INFORMATION: Xaa = Any Amino Acid and up to 2 of them can be
      present or absent
<220> FEATURE:
<221> NAME/KEY: VARIANT
<222> LOCATION: 17, 18
<223> OTHER INFORMATION: Xaa = Any Amino Acid
```

```
<220> FEATURE:
<221> NAME/KEY: VARIANT
<222> LOCATION: 19
<223> OTHER INFORMATION: Xaa = Leu or Ile

<400> SEQUENCE: 12

Xaa Xaa Xaa Tyr Xaa Xaa Xaa Xaa Xaa Xaa Xaa Xaa Xaa Xaa Xaa Tyr
1               5                   10                  15

Xaa Xaa Xaa
```

TRANSGENIC MICE EXPRESSING HUMAN TREM PROTEINS AND METHODS OF USE THEREOF

CROSS-REFERENCE TO RELATED APPLICATIONS

This application claims the benefit of U.S. Provisional Application No. 62/597,750, filed Dec. 12, 2017, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022001500SEQLIST.TXT, date recorded: Dec. 12, 2018, size: 23 KB).

FIELD OF THE INVENTION

The present disclosure relates to transgenic non-human animals whose genomes comprise two or more human genes selected from TREM1, TREML1, TREM2, TREML2, and TREML4, and to uses of such transgenic non-human animals.

BACKGROUND

TREM transmembrane glycoproteins belong to the single immunoglobulin variable (IgV) domain receptor family. The genes encoding human and mouse TREMs map to human chromosome 6p21.1 and mouse chromosome 17C3, respectively. The TREM cluster includes genes encoding TREM1, TREM2, TREM4, and TREM5, as well as the TREM-like genes in both human and mouse. Additionally TREM3 and plasmocytoid dendritic cell (pDC)-TREM were identified in mouse. The TREM-like genes, TREML1, TREML2, and TREML4 in humans, and Treml1, Treml2, and Treml4 in mouse, encode TLT-1, TLT-2, and TLT-4 respectively. The two best characterized of these receptors, TREM1 and TREM2, display some sequence homology with other members of the Ig-SF such as activating NK cells receptors (20% identity with NKp44) and act through association with a DAP12-mediated pathway for signaling.

While TREM proteins, including TREM2, are known to be associated with multiple diseases (e.g., Nasu-Hakola disease, Alzheimer's disease, multiple sclerosis, frontotemporal dementia (FTD), etc.), in vivo study of these proteins, and their potential roles in human disease, remains challenging, as no suitable animal model for studying human TREM proteins has been developed. A major limitation in developing animal models useful for the study of in vivo TREM protein function is that key features of the human TREM proteins may not be structurally conserved. Moreover, expression patterns and protein-protein interactions of the human TREM proteins may not be conserved in other mammalian species. Due to the high likelihood of both structural and functional differences in mammalian TREM proteins, current animal models are unsuitable proxies for the in vivo study of the functions and interactions of human TREM proteins, as well as their role in human diseases.

All references cited herein, including patent applications, patent publications, and non-patent literature are herein incorporated by reference in their entirety, as if each individual reference were specifically and individually indicated to be incorporated by reference.

BRIEF SUMMARY

There is a need for suitable animal models useful for the in vivo study of human TREM protein functions, including animal models coordinately expressing multiple human TREM proteins in relevant cell types. Additionally, there is a need for animal models suitable for testing candidate agents targeting human TREM proteins in vivo, and for animal disease models which express some or all of the human TREM genes to study the association of various human TREM proteins and disease (e.g., Alzheimer's disease and cancer). Accordingly, the present disclosure relates, in part, to transgenic non-human animals (e.g., mice) harboring multiple human TREM genes which effectively express human TREM proteins on myeloid cell lineages. These transgenic animals are useful for the investigation and establishment of functional and pathological properties of human TREM genes in vivo, and to the development of therapeutics that target human TREM genes and their products.

Accordingly, certain aspects of the present disclosure relate to a transgenic non-human animal whose genome comprises two or more human genes, wherein the two or more human genes are selected from the group consisting of TREM1, TREML1, TREM2, TREML2, and TREML4, wherein the two or more human genes are expressed in one or more cells of the transgenic non-human animal, and wherein the one or more cells are selected from the group consisting of myeloid cells, microglia, and any combinations thereof. In some embodiments of any of the animals, the transgenic non-human animal is a rodent. In some embodiments, the transgenic non-human animal is a mouse.

In some embodiments of any of the animals, the genome comprises the human genes TREM1, TREML1, and TREM2. In some embodiments, the genome comprises the human genes TREM1, TREML1, TREM2, TREML2, and TREML4. In some embodiments of any of the animals, one or more of the human genes comprise all intronic and exonic sequences of the one or more genes. In some embodiments of any of the animals, one or more of the human genes comprise at least one flanking sequence at the 5' and/or 3' end of the one or more genes. In some embodiments of any of the animals, the flanking sequence is at least 10,000 base pairs in length. In some embodiments, the flanking sequence comprises one or more human transcriptional regulatory elements. In some embodiments, the one or more human transcriptional regulatory elements direct expression of one or more of the human TREM1, TREML1, TREM2, TREML2, and TREML4 genes. In some embodiments, the one or more human transcriptional regulatory elements direct coordinate expression of at least two of the human TREM1, TREML1, TREM2, TREML2, and TREML4 genes.

In some embodiments of any of the animals, the human TREM1 gene encodes a polypeptide at least 95% identical to a sequence selected from the group consisting of SEQ ID NOS: 1-3. In some embodiments of any of the animals, the human TREML1 gene encodes a polypeptide at least 95% identical to a sequence selected from the group consisting of SEQ ID NOS: 4-6. In some embodiments of any of the animals, the human TREM2 gene encodes a polypeptide at least 95% identical to a sequence selected from the group consisting of SEQ ID NOS: 7-9. In some embodiments of any of the animals, the human TREML2 gene encodes a polypeptide at least 95% identical to SEQ ID NO: 10. In some embodiments of any of the animals, the human TREML4 gene encodes a polypeptide at least 95% identical to SEQ ID NO: 11.

In some embodiments of any of the animals, the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments, the microglia are selected from the group consisting of brain microglial, M1 microglia, activated M1 microglia, M2 microglia, and any combination thereof. In some embodiments, expression of the two or more human genes in the one or more cells of the transgenic non-human animal recapitulates the expression pattern of the two or more human genes in a corresponding human cell. In some embodiments, the one or more cells of the transgenic non-human animal are one or more cells selected from the group consisting of myeloid cells, microglia, and any combinations thereof. In some embodiments, the corresponding human cell is a human cell selected from the group consisting of a human myeloid cell, a human microglial cell, and any combinations thereof. In some embodiments, the two or more human genes are co-expressed. In some embodiments, co-expression of the two or more human genes modulates one or more myeloid immune cell functions. In some embodiments, co-expression of the two or more human genes inhibits one or more myeloid immune cell functions. In some embodiments, co-expression of the two or more human genes enhances one or more myeloid immune cell functions. In some embodiments, the one or more myeloid immune cell functions are selected from the group consisting of: (a) phagocytosis; (b) antigen presentation; (c) immune cell recruitment; (d) immune cell maturation, migration, proliferation, differentiation, and/or survival; (e) modulation of adaptive immune cells such as B cells and T cells; (f) expression and/or secretion of one or more cytokines and/or chemokines; (g) tumor infiltration, tumor cell recognition, and/or tumor cell killing; (h) releasing granules (degranulation) or neutrophil extracellular traps (NETs); (i) anti-parasitic activities; (j) bactericidal activities; (k) clearance of cellular debris and/or protein aggregates; and (l) any combinations thereof.

In some embodiments of any of the animals, expression of the two or more human genes humanizes the TREM repertoire on the one or more cells of the transgenic non-human animal. In some embodiments of any of the animals, the mouse comprises a genome comprising one or more non-functional murine genes, wherein the one or more non-functional murine genes are selected from the group consisting of murine TREM1, murine TREML1, murine TREM2, murine TREML2, murine TREML4, and any combinations thereof. In some embodiments of any of the animals, the mouse comprises a genome comprising a non-functional murine TREM1 gene, a non-functional murine TREML1 gene, a non-functional murine TREM2 gene, a non-functional murine TREML2 gene, and a non-functional murine TREML4 gene.

In some embodiments of any of the animals, the transgenic non-human animal is predisposed to develop one or more diseases. In some embodiments of any of the animals, the transgenic non-human animal is treated or interbred to generate one or more animal disease models. In some embodiments, the one or more diseases are selected from the group consisting of neurodegenerative diseases, immune-related diseases, infectious diseases, and proliferative disorders. In some embodiments, the neurodegenerative diseases are one or more diseases selected from the group consisting of dementia, frontotemporal dementia (FTD), Alzheimer's disease, Parkinson's disease, amyotrophic lateral sclerosis (ALS), Huntington's disease, taupathy disease, Nasu-Hakola disease, and multiple sclerosis. In some embodiments, the disease is Nasu-Hakola disease.

Further provided herein are methods of screening candidate agents, wherein the method comprises i) administering one or more candidate agents to a transgenic non-human animal, wherein the genome of the transgenic non-human animal comprises two or more human genes, wherein the two or more human genes are selected from the group consisting of TREM1, TREML1, TREM2, TREML2, and TREML4, wherein the two or more human genes are expressed in one or more cells of the transgenic non-human animal, and wherein the one of more cells selected from the group consisting of myeloid cells, microglia, and any combinations thereof; and ii) determining whether the one or more candidate agents binds to and/or modulates the function and/or activity of at least one of the two or more human genes in the transgenic non-human animal.

Also provided herein are methods of screening candidate agents, wherein the method comprises i) administering one or more candidate agents to a transgenic non-human animal, wherein the genome of the transgenic non-human animal comprises two or more human genes, wherein the two or more human genes are selected from the group consisting of TREM1, TREML1, TREM2, TREML2, and TREML4, wherein the two or more human genes are expressed in one or more cells of the transgenic non-human animal, and wherein the one of more cells selected from the group consisting of myeloid cells, microglia, and any combination thereof; and ii) determining the effect of the one or more candidate agents on one or more activities and/or functions associated with the expression of at least one of the two or more human genes in the transgenic non-human animal.

In some embodiments of any of the methods of screening, the candidate agent modulates one or more activities and/or functions associated with the expression of human TREM1, human TREML1, human TREM2, human TREML2, and/or human TREML4 genes in the transgenic non-human animal. In some embodiments, the candidate agent inhibits one or more activities and/or functions associated with the expression of human TREM1, human TREML1, human TREM2, human TREML2, and/or human TREML4 genes in the transgenic non-human animal. In some embodiments, the candidate agent activates and/or enhances one or more activities and/or functions associated with the expression of human TREM1, human TREML1, human TREM2, human TREML2, and/or human TREML4 genes in the transgenic non-human animal. In some embodiments, the one or more candidate agents are two or more candidate agents. In some embodiments, the two or more candidate agents target two or more of the human genes. In some embodiments, each of the two or more candidate agents targets a human gene selected from the group consisting of TREM1, TREML1, TREM2, TREML2, and TREML4, and wherein each of the two or more candidate agents targets a different human gene.

In some embodiments of any of the methods of screening, the one or more activities and/or functions associated with expression of the two or more human genes are selected from the group consisting of: (a) immune cell suppression;

(b) decreased expression of one or more pro-inflammatory cytokines, optionally wherein the one or more pro-inflammatory cytokines are selected from a group consisting of IFN-a4, IFN-beta, IL-1β, IL-1alpha, TNF-α, IL-6, IL-8, CRP, IL-20 family members, LIF, IFN-gamma, OSM, CNTF, GM-CSF, IL-11, IL-12, IL-17, IL-18, CRP, MCP-1, and MIP-1-beta; (c) decreased expression of one or more pro-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; (d) increased expression of one or more anti-inflammatory cytokines, optionally wherein the one or more anti-inflammatory cytokines are selected from the group consisting of IL4, IL10, IL13, IL35, IL16, TGF-beta, IL1ra, G-CSF, and soluble receptors for TNF, IFN-beta1a, IFN-beta1b, and IL6; (e) increased expression of one or more anti-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; (f) inhibition of extracellular signal-regulated kinase (ERK) phosphorylation; (g) decreasing tyrosine phosphorylation on one or more cellular proteins, optionally, wherein the one or more cellular proteins comprise ZAP-70 and the tyrosine phosphorylation occurs on Tyr-319 of ZAP-70; (h) decreased expression of C—C chemokine receptor 7 (CCR7); (i) inhibition of microglial cell chemotaxis toward CCL19-expressing and CCL21-expressing cells; (j) decreasing T cell proliferation induced by one or more cells selected from the group consisting of dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; (k) inhibition of osteoclast production, decreased rate of osteoclastogenesis, or both; (l) decreasing survival of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (m) decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (n) inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (o) inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (p) inhibiting maturation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; (q) inhibition of one or more types of clearance selected from the group consisting of apoptotic neuron clearance, nerve tissue debris clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; (r) inhibition of phagocytosis of one or more of apoptotic neurons, nerve tissue debris, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; (s) inhibition of tumor cell killing by one or more of microglia, macrophages, neutrophils, NK cells, dendritic cells, bone marrow-derived dendritic cells, neutrophils, T cells, T helper cells, or cytotoxic T cells; (t) inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; (u) inhibition of anti-tumor cell metastasis activity of one or more of microglia, macrophages, neutrophils, NK cells, dendritic cells, bone marrow-derived dendritic cells, neutrophils, T cells, T helper cells, or cytotoxic T cells; (v) inhibition of one or more ITAM motif containing receptors, optionally wherein the one or more ITAM motif containing receptors are selected from the group consisting of TREM1, TREM2, Sirp beta, FcgR, DAP10, and DAP12; (w) inhibition of signaling by one or more pattern recognition receptors (PRRs), optionally wherein the one or more PRRs are selected from the group consisting of receptors that identify pathogen-associated molecular patterns (PAMPs), receptors that identify damage-associated molecular patterns (DAMPs), and any combination thereof; (x) inhibition of one or more receptors comprising the motif D/Ex0-2YxxL/IX6-8YxxL/I (SEQ ID NO: 12); (y) inhibition of signaling by one or more Toll-like receptors; (z) inhibition of the JAK-STAT signaling pathway; (aa) inhibition of nuclear factor kappa-light-chain-enhancer of activated B cells (NFκB); (bb) de-phosphorylation of an ITAM motif containing receptor; (cc) decreased expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; (dd) decreasing expression of one or more ITAM-dependent genes, optionally wherein the one more ITAM-dependent genes are activated by nuclear factor of activated T cells (NFAT) transcription factors; (ee) promoting differentiation of one or more of immunosuppressor dendritic cells, immunosuppressor macrophages, immunosuppressor neutrophils, immunosuppressor NK cells, myeloid derived suppressor cells, tumor-associated macrophages, tumor-associated neutrophils, tumor-associated NK cells, and regulatory T cells; (ff) rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; (gg) increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; (hh) increasing the number of tumor-promoting myeloid/granulocytic immune-suppressive cells in a tumor, in peripheral blood, or other lymphoid organ; (ii) enhancing tumor-promoting activity of myeloid-derived suppressor cells; (jj) increasing expression of tumor-promoting cytokines in a tumor or in peripheral blood, optionally wherein the tumor-promoting cytokines are TGF-beta or IL-10; (kk) increasing tumor infiltration of tumor-promoting FoxP3+ regulatory T lymphocytes; (ll) enhancing tumor-promoting activity of myeloid-derived suppressor cells (MDSC); (mm) decreasing activation of tumor-specific T lymphocytes with tumor killing potential; (nn) decreasing infiltration of tumor-specific NK cells with tumor killing potential; (oo) decreasing the tumor killing potential of NK cells; (pp) decreasing infiltration of tumor-specific B lymphocytes with potential to enhance immune response; (qq) decreasing infiltration of tumor-specific T lymphocytes with tumor killing potential; (rr) increasing tumor volume; (ss) increasing tumor growth rate; (tt) increasing metastasis; (uu) increasing rate of tumor recurrence; (vv) decreasing efficacy of one or more immune-therapies that modulate anti-tumor T cell responses, optionally wherein the one or more immune-therapies are immune-therapies that target one or more target proteins selected from the group consisting of PD1/PDL1, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, and any combination thereof, or cancer vaccines; (ww) inhibition of PLCγ/PKC/calcium mobilization; (xx) inhibition of PI3K/Akt, Ras/MAPK signaling; and (yy) any combinations thereof.

In some embodiments of any of the methods of screening, the transgenic non-human animal suffers from a disease, disorder, and/or injury. In some embodiments of any of the methods of screening, administering the one or more candidate agents reduces or eliminates one or more signs and/or symptoms of the disease, disorder, and/or injury. In some embodiments of any of the methods of screening, the disease, disorder, and/or injury is one or more of autoimmunity, susceptibility to infection, cancer, proliferative disorders, and neurodegenerative disorders. In some embodiments of any of the methods of screening, the disease, disorder, and/or injury is one or more of autoimmunity, susceptibility to infection, cancer, proliferative disorders, and/or neurodegenerative disorders. In some embodiments, the one or more diseases, disorders, and/or injuries is one or more of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential Tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases.

In some embodiments of any of the methods of screening, the effect of the one or more candidate agents is selected from the group consisting of: (a) modulating cell surface levels of one or more polypeptides encoded by the human TREM1, TREML1, TREM2, TREML2, or TREML4 genes; (b) competing for binding with a natural ligand of one or more polypeptides encoded by the human TREM1, TREML1, TREM2, TREML2, or TREML4 genes; (c) modulating T cell proliferation and/or phagocytosis; (d) modulating the survival of macrophages, neutrophils, NK cells, and/or dendritic cells; (e) modulating CCR7 and/or F-actin in myeloid cells and/or microglia; (f) modulating expression of one or more inflammatory cell surface markers on myeloid cells and/or microglia; (g) modulating myeloid-derived suppressor cell (MDSC) proliferation, activation, and/or function; (h) modulating IL-10 secretion from one or more myeloid cells; (i) modulating SYK and/or ERK activation and/or phosphorylation; (j) modulating DAP12 activation and/or phosphorylation; and (k) any combinations thereof.

In some embodiments of any of the methods of screening, the transgenic non-human animal is a rodent. In some embodiments, the transgenic non-human animal is a mouse.

In some embodiments of any of the methods of screening, the genome comprises the human genes TREM1, TREML1, and TREM2. In some embodiments, the genome comprises the human genes TREM1, TREML1, TREM2, TREML2, and TREML4. In some embodiments, one or more of the human genes comprise all intronic and exonic sequences of the one or more genes. In some embodiments, one or more of the human genes comprise at least one flanking sequence at the 5' and/or 3' end of the one or more genes. In some embodiments, the flanking sequence is at least 10,000 base pairs in length. In some embodiments, the flanking sequence comprises one or more human transcriptional regulatory elements. In some embodiments, the one or more human transcriptional regulatory elements directs expression of one or more of the human TREM1, TREML1, TREM2, TREML2, and TREML4 genes. In some embodiments, the one or more human transcriptional regulatory elements directs coordinate expression of at least two of the human TREM1, TREML1, TREM2, TREML2, and TREML4 genes.

In some embodiments of any of the methods of screening, the human TREM1 gene encodes a polypeptide at least 95% identical to a sequence selected from the group consisting of SEQ ID NOS: 1-3. In some embodiments of any of the methods of screening, the human TREML1 gene encodes a polypeptide at least 95% identical to a sequence selected from the group consisting of SEQ ID NOS: 4-6. In some embodiments of any of the methods of screening, the human TREM2 gene encodes a polypeptide at least 95% identical to a sequence selected from the group consisting of SEQ ID NOS: 7-9. In some embodiments of any of the methods of screening, the human TREML2 gene encodes a polypeptide at least 95% identical to SEQ ID NO: 10. In some embodiments of any of the methods of screening, the human TREML4 gene encodes a polypeptide at least 95% identical to SEQ ID NO: 11.

In some embodiments of any of the methods of screening, the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments, the microglia are selected from the group consisting of brain microglial, M1 microglia, activated M1 microglia, M2 microglia, and any combination thereof. In some embodiments, expression of the two or more human genes in the one or more cells of the transgenic non-human animal recapitulates the expression pattern of the two or more human genes in a corresponding human cell. In some embodiments, he one or more cells of the transgenic non-human animal are one or more cells selected from the group consisting of myeloid cells, microglia, and any combinations thereof. In some embodiments, the corresponding human cell is a human cell selected from the group consisting of a human myeloid cell, a human microglial cell, and any combinations thereof. In some embodiments, the two or more human genes are co-expressed. In some embodiments, co-expression of the two or more human genes modulates one or more myeloid immune cell functions. In some embodiments, co-expression of the two or more human genes inhibits one or more myeloid immune cell functions. In some embodiments, co-expression of the two or more human genes enhances one or more myeloid immune cell functions.

In some embodiments of any of the methods of screening, the one or more myeloid immune cell functions are selected from the group consisting of: (a) phagocytosis; (b) antigen presentation; (c) immune cell recruitment; (d) immune cell maturation, migration, proliferation, differentiation, and/or survival; (e) modulation of adaptive immune cells such as B cells and T cells; (f) expression and/or secretion of one or more cytokines and/or chemokines; (g) tumor infiltration, tumor cell recognition, and/or tumor cell killing; (h) releasing granules (degranulation) or neutrophil extracellular traps (NETs); (i) anti-parasitic activities; (j) bactericidal activities; (k) clearance of cellular debris and/or protein aggregates; and (l) any combination thereof.

In some embodiments of any of the methods of screening, expression of the two or more human genes humanizes the TREM repertoire on the one or more cells of the transgenic non-human animal. In some embodiments, the mouse comprises a genome comprising one or more non-functional murine genes, wherein the one or more non-functional murine genes are selected from the group consisting of murine TREM1, murine TREML1, murine TREM2, murine TREML2, murine TREML4, and any combinations thereof. In some embodiments, the mouse comprises a genome comprising a non-functional murine TREM1 gene, a non-functional murine TREML1 gene, a non-functional murine TREM2 gene, a non-functional murine TREML2 gene, and a non-functional murine TREML4 gene.

Provided herein are also methods for recapitulating a human TREM immune system in a non-human animal, the method comprising generating a transgenic non-human animal whose genome comprises two or more human genes, wherein the two or more human genes are selected from the group consisting of TREM1, TREML1, TREM2, TREML2, and TREML4, wherein the two or more human genes are coordinately expressed in one or more cells of the transgenic non-human animal, and wherein the one of more cells are selected from the group consisting of myeloid cells, microglia, and any combinations thereof.

In some embodiments of any of the methods, the transgenic non-human animal is a rodent. In some embodiments, the transgenic non-human animal is a mouse. In some embodiments, the genome comprises the human genes TREM1, TREML1, and TREM2. In some embodiments, the genome comprises the human genes TREM1, TREML1, TREM2, TREML2, and TREML4. In some embodiments, one or more of the human genes comprise all intronic and exonic sequences of the one or more genes. In some embodiments, one or more of the human genes comprise at least one flanking sequence at the 5' and/or 3' end of the one or more genes. In some embodiments, the flanking sequence is at least 10,000 base pairs in length. In some embodiments, the flanking sequence comprises one or more human transcriptional regulatory elements. In some embodiments, the one or more human transcriptional regulatory elements directs expression of one or more of human TREM1, TREML1, TREM2, TREML2, and TREML4 genes. In some embodiments, the one or more human transcriptional regulatory elements directs coordinate expression of at least two of the human TREM1, TREML1, TREM2, TREML2, and TREML4 genes. In some embodiments, the human TREM1 gene encodes a polypeptide at least 95% identical to a sequence selected from the group consisting of SEQ ID NOS: 1-3. In some embodiments, the human TREML1 gene encodes a polypeptide at least 95% identical to a sequence selected from the group consisting of SEQ ID NOS: 4-6. In some embodiments, the human TREM2 gene encodes a polypeptide at least 95% identical to a sequence selected from the group consisting of SEQ ID NOS: 7-9. In some embodiments, the human TREML2 gene encodes a polypeptide at least 95% identical to SEQ ID NO: 10. In some embodiments, the human TREML4 gene encodes a polypeptide at least 95% identical to SEQ ID NO: 11.

In some embodiments of any of the methods, the myeloid cells are selected from the group consisting of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments, the microglia are selected from the group consisting of brain microglial, M1 microglia, activated M1 microglia, M2 microglia, and any combination thereof. In some embodiments, coordinate expression of the two or more human genes modulates one or more myeloid immune cell functions. In some embodiments, expression of the two or more human genes inhibits one or more myeloid immune cell functions. In some embodiments, coordinate expression of the two or more human genes enhances one or more myeloid immune cell functions.

In some embodiments of any of the methods, the one or more myeloid immune cell functions are selected from the group consisting of: (a) phagocytosis; (b) antigen presentation; (c) immune cell recruitment; (d) immune cell maturation, migration, proliferation, differentiation, and/or survival; (e) modulation of adaptive immune cells such as B cells and T cells; (f) expression and/or secretion of one or more cytokines and/or chemokines; (g) tumor infiltration, tumor cell recognition, and/or tumor cell killing; (h) releasing granules (degranulation) or neutrophil extracellular traps (NETs); (i) anti-parasitic activities; (j) bactericidal activities; (k) clearance of cellular debris and/or protein aggregates; and (l) any combinations thereof.

In some embodiments of any of the methods, coordinate expression of the two or more human genes humanizes the TREM repertoire on the one or more cells of the transgenic non-human animal. In some embodiments, the mouse comprises a genome that does not encode at least one murine gene, wherein the murine gene is selected from the group consisting of murine TREM1, murine TREML1, murine TREM2, murine TREML2 and murine TREML4. In some embodiments, the mouse comprises a genome comprising one or more non-functional murine genes, wherein the one or more non-functional murine genes are selected from the group consisting of murine TREM1, TREML1, murine TREM2, murine TREML2, murine TREML4, and any combinations thereof.

Provided herein are also methods of generating a non-human animal disease model with a human TREM repertoire, the method comprising introducing one or more genetic determinants of a disease into the genome of the non-human animal described herein. In some embodiments, the one or more genetic determinants are introduced into the genome of the non-human animal by mating. In some embodiments, the one or more genetic determinants are introduced into the genome of the non-human animal by mating with a disease model non-human animal. In some embodiments, the one or more genetic determinants are introduced into the genome of the non-human animal by genetic manipulation. In some embodiments, the disease is selected from the group consisting of cancer, proliferative disorders, infectious diseases, and neurodegenerative disorders such as Alzheimer's disease. In some embodiments, the genetic determinant is a polynucleotide encoding a polypeptide comprising one or more mutations, wherein the polypeptide is selected from the group consisting of amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43 (TDP-43), RNA-binding protein FUS, huntingtin (HTT), translation endoplasmic reticulum ATPase (VCP), microtubule-associated protein tau (MAPT), progranulin, protein C9orf72, charged multivesicular body protein 2b (CHMP2B), TYRO protein tyrosine kinase-binding protein (TYROBP), and any combinations thereof.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

The patent or application file contains at least one drawing executed in color. Copies of this patent or patent application publication with color drawings will be provided by the office upon request and payment of the necessary fee.

FIGS. 4A-4D show protein levels of inflammatory cytokines CCL2 and TNFα secreted in response to incubation of wild-type and CTD-3222A20 transgenic (Bac-Tg) peritoneal macrophages cultured in vitro with anti-TREM2 antibodies (anti-TREM2 antibody #2, anti-TREM2 antibody #6, anti-TREM2 antibody #7, and anti-TREM2 antibody #4), as well as control antibodies. FIG. 4A shows protein levels of CCL2 secreted after 24 hours of incubation with the indicated antibodies. FIG. 4B shows protein levels of CCL2 secreted after 60 hours of incubation with the indicated antibodies. FIG. 4C shows protein levels of TNFα secreted after 24 hours of incubation with the indicated antibodies.

FIG. 4D shows protein levels of TNFα secreted after 60 hours of incubation with the indicated antibodies.

FIG. 8A shows DAP12 phosphorylation as determined by western blot analysis in wild-type (WT-1) and CTD-3222A20 transgenic (Bac-Tg1) mouse macrophages after incubation with anti-TREM2 antibodies (anti-TREM2 antibody #2 and anti-TREM2 antibody #4) or IgG control antibody (MOPC21). FIG. 8B shows DAP12 phosphorylation as determined by western blot analysis in wild-type (WT-2) and CTD-3222A20 transgenic (Bac-2) mouse macrophages after incubation with anti-TREM2 antibodies (anti-TREM2 antibody #6 as murine IgG1, anti-TREM2 antibody #6 as murine IgG2a, anti-TREM2 antibody #2 and anti-TREM2 antibody #4) or IgG control antibody (MOPC21).

FIG. 9A shows the viability of wild-type and CTD-3222A20 transgenic (BAC-TG) bone marrow-derived macrophages after incubation with plate-bound anti-TREM2 antibodies (anti-TREM2 antibody #6, anti-TREM2 antibody #7, anti-TREM2 antibody #4, anti-TREM2 antibody #5, and anti-TREM2 antibody #2).

FIG. 9B shows the viability of wild-type and CTD-3222A20 transgenic (BAC-TG) bone marrow-derived macrophages after incubation with soluble anti-TREM2 antibodies (anti-TREM2 antibody #6, anti-TREM2 antibody #7, anti-TREM2 antibody #4, anti-TREM2 antibody #5, and anti-TREM2 antibody #2).

FIG. 9C shows the viability of primary human dendritic cells (hDCs) after incubation with soluble anti-TREM2 antibodies (anti-TREM2 antibody #6, anti-TREM2 antibody #7, anti-TREM2 antibody #4, anti-TREM2 antibody #5, and anti-TREM2 antibody #2).

FIG. 12A shows the levels of soluble TREM2 in the plasma of two CTD-3222A20 transgenic mouse lines (101 and 257). FIG. 12B shows the levels of soluble human and mouse TREM2 in the plasma of wild-type and CTD-3222A20 transgenic (BAC) mice.

FIG. 13A shows CD11b positive white blood cells from TREM transgenic or wild-type B6 mice stained by FACS with antibodies against human TREML2 (hTLT2-PE). FIG. 13B shows CD11b positive white blood cells from TREM transgenic or wild-type B6 mice stained by FACS with antibodies against human TREM1.

DETAILED DESCRIPTION

Figure 1:
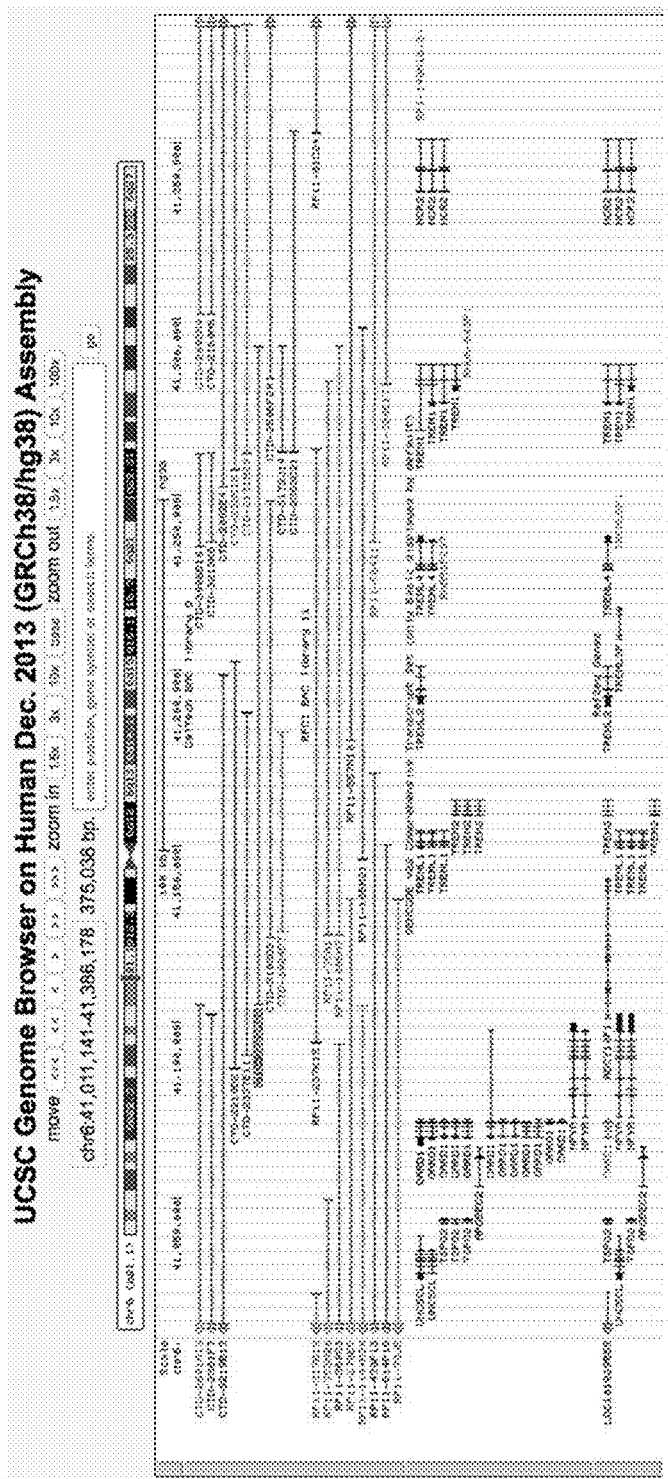
FIG. 1 shows a UCSC genome browser map of the genes, including TREM1, TREML1, TREM2, TREML2, and TREML4, on a region of human Chromosome 6 that are included in the bacterial artificial chromosome (BAC) CTD-3222A20, as labelled.

The present disclosure relates to transgenic non-human animals whose genomes comprise two or more human genes selected from the group consisting of TREM1, TREML1, TREM2, TREML2, and TREML4; to methods of screening candidate agents that bind to and/or modulate the function and/or activity of at least one of the human genes in the transgenic non-human animals; to methods of screening candidate agents to determine their effect on one or more activities and/or functions associated with expression of at least one of the human genes in the transgenic non-human animals; to methods of recapitulating a human TREM immune system in a non-human animal; and to methods of generating a non-human animal disease model comprising a human TREM repertoire.

The following description sets forth exemplary methods, parameters, and the like. It should be recognized, however, that such description is not intended as a limitation on the scope of the present disclosure but is instead provided as a description of exemplary embodiments.

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, a "subject" or an "individual" refers to any animal, including non-human primates, domestic and farm animals, and zoo, sports, or pet animals, such as dogs, horses, cats, cows, as well as animals used in research, such as mice and rats.

As used herein, the term "animal" or "non-human animal" includes all vertebrate and invertebrate animals, except humans. Examples of animals include, but are not limited to, domesticated animals (e.g., cows, sheep, cats, dogs, and horses), primates (e.g., non-human primates such as monkeys), rabbits, and rodents (e.g., mice and rats). In some embodiments, the animal is a mouse. Additionally, the term refers to an individual animal in all stages of developments, including embryonic and fetal stages. As used herein, the term "transgenic animal" or "transgenic non-human animal" refers to an animal containing one or more cells bearing genetic information (e.g., DNA) received, directly or indirectly, by deliberate genetic manipulation at a subcellular level, such as by microinjection or infection with recombinant virus. This introduced DNA molecule mar be integrated within a chromosome, or it may be extra-chromosomally replicating DNA.

As used herein, the term "germ cell-line transgenic animal" refers to a transgenic animal in which the genetic information was introduced into a germ line cell, thereby conferring the ability to transfer the information to offspring. If such offspring in fact possess some or all of that information, then they too are transgenic animals.

As used herein, the term "wild-type" refers to a polynucleotide, polypeptide, and/or animal (e.g., a mouse or rat) when isolated from a naturally occurring source. A wild-type polynucleotide, polypeptide, and/or animal (e.g., a mouse or rat) is that which is most frequently observed in a population and is thus arbitrarily designated the "normal" or "wild-type" form of that polynucleotide, polypeptide, and/or animal. In contrast, the term "modified" or "mutant" refers to a polynucleotide, polypeptide, and/or animal (e.g., a mouse or rat) that displays modifications in sequence and/or functional properties (e.g., altered characteristics) when compared to the wild-type polynucleotide, polypeptide, and/or animal (e.g., a mouse or rat).

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability to elicit a desired response in the individual. A therapeutically effective amount is also one in which any toxic or detrimental effects are outweighed by the therapeutically beneficial effects.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, the terms "coordinately expressed" and "coordinate expression" refers to the co-regulated expression of two or more polynucleotides.

As used herein, the terms "polypeptide," "protein," and "peptide" are used interchangeably and may refer to a polymer of two or more amino acids.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "candidate agent" refers to a molecule that modulated (e.g., activates or inhibits) one or more TREM activities and/or functions. In some embodiments, the term "candidate agent refers to a molecule that reduces (including significantly), decreases, blocks, inhibits, or interferes with a TREM (mammalian, such as a human TREM) biological activity in vitro, in situ, and/or in vivo. In some embodiments, the term "candidate agent refers to a molecule that induces (including significantly), increases, or enhances a TREM (mammalian, such as a human TREM) biological activity in vitro, in situ, and/or in vivo. The term "agent" implies no specific mechanism of biological action whatsoever, and expressly includes and encompasses all possible pharmacological, physiological, and biochemical interactions with a TREM whether direct or indirect, and whether interacting with a TREM, one or more of its ligands, or through another mechanism, and its consequences which can be achieved by a variety of different, and chemically divergent, compositions. Exemplary agents include, without limitation, an antibody that specifically binds to a TREM (e.g., an agonist or antagonist antibody), a soluble TREM receptor protein, a soluble TREM –Fc fusion protein (e.g., TREM immunoadhesins), a soluble TREM receptor that binds to a TREM ligand, a TREM –Fc fusion protein (e.g., TREM immunoadhesin) that binds to a TREM ligand, an anti-sense molecule directed to a polynucleotide encoding a TREM, a short interfering RNA ("siRNA") molecule directed to a polynucleotide encoding a TREM, a TREM inhibitory compound, a TREM activating compound, an RNA or DNA aptamer that binds to a TREM, a TREM structural analog, and/or small molecule. In some embodiments, a TREM inhibitor (e.g., an antibody) binds (physically interacts with) an agent that decreases cellular levels of a TREM, inhibits interaction between a TREM and one or more TREM ligands, or both, binds to a TREM ligand, and/or inhibits (reduces) TREM synthesis or production. In some embodiments, a TREM activator (e.g., an antibody) binds (physically interacts with) an agent that increases cellular levels of a TREM, enhances interaction between a TREM and one or more TREM ligands, or both, binds to a TREM ligand, and/or activates (enhances) TREM synthesis or production. In other embodiments, an agent of the present disclosure binds a TREM and prevents its binding to one or more of its ligands. In other embodiments, an agent of the present disclosure binds a TREM and enhances its binding to one or more of its ligands. In still other embodiments, an agent of the present disclosure reduces or eliminates expression (i.e., transcription or translation) of a TREM. In still other embodiments, an agent of the present disclosure increases or enhances expression (i.e., transcription or translation) of a TREM.

As used herein, the term "agent that binds or interacts with a TREM" refers to a molecule that either directly or indirectly interacts with a TREM protein. The term "agent" implies no specific mechanism of biological action whatsoever, and expressly includes and encompasses all possible pharmacological, physiological, and biochemical interactions with a TREM whether direct or indirect, and whether interacting with a TREM or through another mechanism, and its consequences which can be achieved by a variety of different, and chemically divergent, compositions.

As used herein, the term "RNA interference" or "RNAi" refers generally to a process in which a double-stranded RNA molecule or a short hairpin RNA molecule reducing or inhibiting the expression of a nucleic acid sequence with which the double-stranded or short hairpin RNA molecule shares substantial or total homology. The term "short interfering RNA" or "siRNA" or "RNAi agent" refers to an RNA sequence that elicits RNA interference. See Kreutzer et al., WO 00/44895; Zernicka-Goetz et al., WO 01/36646; Fire, WO 99/32619; Mello and Fire, WO 01/29058. As used herein, siRNA molecules include RNA molecules encompassing chemically modified nucleotides and non-nucleotides. The term "ddRNAi agent" refers to a DNA-directed RNAi agent that is transcribed from an exogenous vector. The terms "short hairpin RNA" or "shRNA" refer to an RNA structure having a duplex region and a loop region. In certain embodiments, ddRNAi agents are expressed initially as shRNAs.

As used herein, the term "aptamer" refers to a heterologous oligonucleotide capable of binding tightly and specifically to a desired molecular target, such as, for example, common metabolic cofactors (e.g., Coenzyme A, S-adenosyl methionine, and the like), proteins (e.g., complement protein C5, antibodies, and the like), or conserved structural elements in nucleic acid molecules (e.g., structures important for binding of transcription factors and the like). Aptamers typically comprise DNA or RNA nucleotide sequences ranging from about 10 to about 100 nucleotides in length, from about 10 to about 75 nucleotides in length, from about 10 to about 50 nucleotides in length, from about 10 to about 35 nucleotides in length, and from about 10 to about 25 nucleotides in length. Synthetic DNA or RNA oligonucleotides can be made using standard solid phase phosphoramidite methods and equipment, such as by using a 3900 High Throughput DNA Synthesizer™, available from Applied Biosystems (Foster City, Calif.). Aptamers frequently incorporate derivatives or analogs of the commonly occurring nucleotides found in DNA and RNA (e.g., A, G, C, and T/U), including backbone or linkage modifications (e.g., peptide nucleic acid (PNA) or phosphothioate linkages) to increase resistance to nucleases, binding avidity, or to otherwise alter their pharmacokinetic properties. Exemplary modifications are set forth in U.S. Pat. Nos. 6,455,308; 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; and in WIPO publications WO 00/56746 and WO 01/14398. Methods for synthesizing oligonucleotides comprising such analogs or derivatives are disclosed, for example, in the patent publications cited above, and in U.S. Pat. Nos. 6,455,308; 5,614, 622; 5,739,314; 5,955,599; 5,962,674; 6,117,992; and in WO 00/75372.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to a "gene" is a reference to from one to many genes.

It is understood that aspect and embodiments of the present disclosure described herein include "comprising," "consisting," and "consisting essentially of" aspects and embodiments.

Transgenic Non-Human Animals

Certain aspects of the present disclosure relate to transgenic non-human animals whose genomes comprise two or more human genes selected from TREM1, TREML1, TREM2, TREML2, and TREML4. In some embodiments, the two or more human genes are expressed (e.g., co-expressed) in one or more cells of the transgenic non-human animal. In some embodiments, the two or more human genes are coordinately expressed in one or more cells of the transgenic animal. In some embodiments, expression (e.g., co-expression, coordinate expression) of the two or more human genes in the transgenic non-human animal recapitulates the expression pattern of the two or more human genes in a corresponding human cell. In some embodiments, expression (e.g., co-expression, coordinate expression) of the two or more human genes humanizes the TREM repertoire on the one or more cells of the transgenic non-human animal. In some embodiments, the one or more cells of the transgenic non-human animal are one or more of myeloid cells (e.g., macrophages, dendritic cells, osteoclasts, microglia, monocytes, Langerhans cells of skin, and Kupffer cells, and any combinations thereof).

In some embodiments, the two or more human genes are expressed (e.g., co-expressed) in one or more myeloid cells of the transgenic non-human animal. In some embodiments, the two or more human genes are coordinately expressed in one or more myeloid cells of the transgenic non-human animal. In some embodiments, expression (e.g., co-expression, coordinate expression) of the two or more human genes in one or more myeloid cells of the transgenic non-human animal recapitulates the expression pattern of the two or more human genes in a corresponding human myeloid cell. In some embodiments, the one or more myeloid cells are one or more of myeloid-derived suppressor cells, granulocyte-like myeloid-derived suppressor cells, monocyte-like myeloid-derived suppressor cells, monocytes, macrophages, bone marrow-derived macrophages, M1 macrophages, activated M1 macrophages, M2 macrophages, neutrophils, M1 neutrophils, activated M1 neutrophils, M2 neutrophils, basophils, eosinophils, erythrocytes, dendritic cells, bone marrow-derived dendritic cells, megakaryocytes, and any combination thereof. In some embodiments, expression (e.g., co-expression, coordinate expression) of the two or more human genes on one or more myeloid cells humanizes the TREM repertoire on the one or more myeloid cells.

In some embodiments, the two or more human genes are expressed (e.g., co-expressed) in one or more microglial cells of the transgenic non-human animal. In some embodiments, the two or more human genes are coordinately expressed in one or more microglial cells of the transgenic non-human animal. In some embodiments, expression (e.g., co-expression, coordinate expression) of the two or more human genes in one or more microglial cells of the transgenic non-human animal recapitulates the expression pattern of the two or more human genes in a corresponding human microglial cell. In some embodiments, the one or more microglial cells are one or more of brain microglial cells, M1 microglial cells, activated M1 microglial cells, M2 microglial cells, and any combination thereof. In some embodiments, expression (e.g., co-expression, coordinate expression) of the two or more human genes on one or more microglial cells humanizes the TREM repertoire on the one or more microglial cells.

In some embodiments, expression (e.g., co-expression, coordinate expression) of the two or more human genes in the transgenic non-human animals suppresses one or more myeloid immune cell functions in the transgenic non-human animal. In some embodiments, the one or more myeloid immune cell functions are one or more of phagocytosis; antigen presentation; immune cell recruitment, maturation, migration, proliferation, differentiation, and/or immune cell survival; modulation of adaptive immune cells (e.g., B cells and/or T cells); expression and/or secretion of one or more cytokines and/or chemokines (e.g., IL-1beta, IL-6, IL-8, IL-10, IL-11, IL-12, IL-12p70, IL-17, IL-18, IL-20 family members, IL-33, CRP, LIF, MCP-1, TNFalpha, IFN-α4, IFN-beta, IFN-gamma, OSM, CNTF, GM-CSF, TGF beta, TGF-beta members of the chemokine protein families, TNG, etc.); tumor infiltration, tumor cell recognition, and/or tumor cell killing; releasing granules (degranulation) and/or neutrophil extracellular traps (NETs); anti-parasitic activities; bactericidal activities; clearance of cellular debris and/or protein aggregates; and any combinations thereof.

In some embodiments, expression (e.g., co-expression, coordinate expression) of the two or more human genes in the transgenic non-human animals suppresses one or more myeloid immune cell functions by about 5%, about 10%, about 15%, about 20%, about 25%, about 30%, about 35%, about 40%, about 45%, about 50%, about 55%, about 60%, about 70%, about 75%, about 80%, about 85%, about 90%, about 95%, or about 99% relative to a control non-human animal (e.g., an animal not expressing the two or more human genes). In some embodiments, expression (e.g., co-expression, coordinate expression) of the two or more human genes in the transgenic non-human animals suppresses one or more myeloid immune cell functions by about 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 10 fold, about 100 fold or about 1000 fold relative to a control non-human animal (e.g., an animal not expressing the two or more human genes).

In some embodiments, expression (e.g., co-expression, coordinate expression) of the two or more human genes in the transgenic non-human animals enhances/activates one or more myeloid immune cell functions in the transgenic non-human animal. In some embodiments, the one or more myeloid immune cell functions are one or more of phagocytosis; antigen presentation; immune cell recruitment, maturation, migration, proliferation, differentiation, and/or immune cell survival; modulation of adaptive immune cells (e.g., B cells and/or T cells); expression and/or secretion of one or more cytokines and/or chemokines (e.g., IL-1beta, IL-6, IL-8, IL-10, IL-11, IL-12, IL-12p70, IL-17, IL-18, IL-20 family members, IL-33, CRP, LIF, MCP-1, TNFalpha, IFN-α4, IFN-beta, IFN-gamma, OSM, CNTF, GM-CSF, TGF beta, TGF-beta members of the chemokine protein families, TNG, etc.); tumor infiltration, tumor cell recognition, and/or tumor cell killing; releasing granules (degranulation) and/or neutrophil extracellular traps (NETs); anti-parasitic activities; bactericidal activities; clearance of cellular debris and/or protein aggregates; and any combinations thereof.

In some embodiments, expression (e.g., co-expression, coordinate expression) of the two or more human genes in the transgenic non-human animals enhances/activates one or more myeloid immune cell functions by about 5%, about 10%, about 15%, about 20%, about 25%, about 30%, about 35%, about 40%, about 45%, about 50%, about 55%, about 60%, about 70%, about 75%, about 80%, about 85%, about 90%, about 95%, or about 99% relative to a control non-human animal (e.g., an animal not expressing the two or more human genes). In some embodiments, expression (e.g., co-expression, coordinate expression) of the two or more human genes in the transgenic non-human animals enhances/activates one or more myeloid immune cell functions by about 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 10 fold, about 100 fold or about 1000 fold relative to a control non-human animal (e.g., an animal not expressing the two or more human genes).

Transgenic non-human animals of the present disclosure may be any non-human animal known in the art. Examples of non-human animals may include, without limitation, laboratory animals (e.g., mice, rats, hamsters, gerbils, guinea pigs, etc.), livestock (e.g., horses, cattle, pigs, sheep, goats, ducks, geese, chickens, etc.), non-human primates (e.g., apes, chimpanzees, orangutans, monkeys, etc.), fish, amphibians (e.g., frogs, salamanders, etc.), reptiles (e.g., snakes, lizards, etc.), and other animals (e.g., foxes, weasels, rabbits, mink, beavers, ermines, otters, sable, seals, coyotes, chinchillas, deer, muskrats, possums, etc.).

In some embodiments, the transgenic non-human animal is a rodent (e.g., a mouse, a rat, a hamster, a gerbil, or a guinea pig). Hamster strains useful for generating transgenic hamsters may include, but are not limited to, Syrian hamsters, Chinese hamsters, European hamsters, and Djungarian hamsters. Rat strains useful for generating transgenic rats may include, but are not limited to, Sprague Dawley® rats, Lewis rats, Fischer 344 rats, Long Evans rats, CD-IGS rats, and Wistar rats. In some embodiments, the transgenic non-human animal is a mouse. Mouse strains useful for generating transgenic mice may include, but are not limited to, CD-1® Nude mice, CD-1 mice, NU/NU mice, BALB/C Nude mice, NIH-III mice, SCID™ mice, outbred SCID™ mice, SCID Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice, and congenic mice. In some embodiments, mice useful for generating transgenic mice may further include, but are not limited to, hybrids of any of the aforementioned mouse strains, $F_1$ hybrids of any of the aforementioned mouse strains, $F_2$ hybrids of any of the aforementioned mouse strains, and outbred mice of any of the aforementioned mouse strains.

In some embodiments, the transgenic non-human animals of the present disclosure are chimeric transgenic non-human animals. In some embodiments, the transgenic non-human animals of the present disclosure are transgenic non-human animals with germ cells and somatic cells containing one or more (e.g., one or more, two or more, three or more, four or more, etc.) nucleotide sequences encoding two or more human genes selected from TREM1, TREML1, TREM2, TREML2, and TREML4. In some embodiments, the one or more nucleotides sequences are stably integrated into the genome of the transgenic non-human animals. In some embodiments, the one or more nucleotides are bacterial artificial chromosomes stably integrated into the genome of the transgenic non-human animal. In some embodiments, the one or more nucleotide sequences are extrachromosomal. In some embodiments, the extrachromosomal nucleotide sequence is provided as a minichromosome, a yeast artificial chromosome, or a bacterial artificial chromosome.

In some embodiments, the genomes of the transgenic non-human animals of the present disclosure comprise any of 1, 2, 3, 4, 5, 6, 7, 8, 9, 10, 11, 12, 13, 14, 15 or more copies of the two or more human genes selected from TREM1, TREML1, TREM2, TREML2, and TREML4. In some embodiments, the copy number of the two or more human genes is the same in the genome of the transgenic non-human animal (e.g., the same number of copies of a first and second human gene, the same number of copies of a first, second, and third human gene, etc.). In some embodiments, the copy number of the two or more human genes is different in the genome of the transgenic non-human animal (e.g., a different number of copies of a first and second human gene, a different number of copies of a first, second, and third human gene, etc.). In some embodiments, the genome of the transgenic non-human animal comprises three or more human genes, and the copy number of at least two of the human genes is the same (e.g., the same number of copies of the first and second human gene, and a different number of copies of the third human gene; the same number of copies of the first and third human gene, and a different number of copies of the second human gene, etc.).

In some embodiments, a transgenic non-human animal of the present disclosure is pre-disposed to develop one or more diseases, disorders, and/or injuries. In some embodiments, the one or more diseases, disorders, and/or injuries is one or more of autoimmunity, susceptibility to infection, cancer, proliferative disorders, and/or neurodegenerative disorders. In some embodiments, the one or more diseases, disorders, and/or injuries is one or more of dementia, frontotemporal dementia (FTD), Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential Tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases.

In some embodiments, the transgenic non-human animal is treated to generate one or more animal disease models (e.g., a transgenic non-human animal being implanted with a syngeneic tumor such as melanoma). In some embodiments, the transgenic non-human animal is interbred to generate one or more animal diseases models. In some embodiments, the transgenic non-human animal is bred with a disease model non-human animal. In some embodiments, the disease model non-human animal is a model of cancer (e.g., melanoma, acute myeloid leukemia, etc.), proliferative disorders, immune-related disease, infectious diseases (e.g., bacterial infections), and/or neurodegenerative diseases/disorders (e.g., Alzheimer's disease). In some embodiments, the neurodegenerative diseases/disorders are one or more of dementia, frontotemporal dementia (FTD), Alzheimer's disease, Nasu-Hakola disease, Parkinson's disease, amyotrophic lateral sclerosis (ALS), Huntington's disease, taupathy disease, and multiple sclerosis. In some embodiments, the disease model non-human animal is an Alzheimer's disease model non-human animal. In some embodiments, the genome of the disease model non-human animal comprises a polynucleotide comprising one or more mutations. In some embodiments, the one or more mutations are one or more inactivating mutations. Examples of inactivating mutations may include, but are not limited to, deletions, insertions, point mutations, and rearrangements. In some embodiments, the genome of the disease model non-human animal comprises a polynucleotide encoding a polypeptide comprising one or more mutations. In some embodiments, the polypeptide comprising one or more mutations is one or more of the polypeptides amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43 (TARDBP), RNA-binding protein FUS, huntingtin (HTT), translation endoplasmic reticulum ATPase (VCP), microtubule-associated protein tau (MAPT), progranulin, protein C9orf72, charged multivesicular body protein 2b (CHMP2B), Triggering receptor expressed on myeloid cells 2 (TREM2), TYRO protein tyrosine kinase-binding protein (TYROBP), and clinical mutant forms thereof.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the Progranulin gene.

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

Taupathy Disease

Taupathy diseases, or Tauopathies, are a class of neurodegenerative disease caused by aggregation of the microtubule-associated protein tau within the brain. Alzheimer's disease (AD) is the most well-known taupathy disease, and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

Animal models have been developed to model various aspects of dementia, FTD, AD, and Taupathy diseases, including, for example, the accumulation of protein aggregation (e.g., plaques and neurofibrillary tangles) leading to lesions in the brain, the spreading of key histopathological markers (e.g., amyloid β plaques and neurofibrillary tangles) that lead to the definition of the Braak stages, and the formation of distinct clinical features (e.g., neuronal/synapse loss at specific predilection sites, early memory deficits, parkinsonism, memory loss in advanced stages) of FTD, AD, and Taupathy diseases. Examples of animal models useful for modeling one or more signs or symptoms of AD and/or FTD and/or Taupathy diseases may include, without limitation, the mouse strains PDAPP, J20, APP23, Tg2576, JNPL3, pR5, and 5XFAD, and the rat strains SHR72 and SHR318) (See e.g., Götz, J. and Ittner, L. M. (2008) Nat. Rev. Nerurosci. 9:352-44; Koson, P. et al. (2008) Eur. J. Neurosci. 28(2): 239-46; and Götz, J. and Götz, N. N. (2009) ASN Neuro. 1(4)).

Nasu-Hakola Disease

Nasu-Hakola disease (NHD), which may alternatively be referred to as polycystic lipomembranous osteodysplasia with sclerosing leukoencephalopathy (PLOSL), is a rare inherited leukodystrophy characterized by progressive presenile dementia associated with recurrent bone fractures due to polycystic osseous lesions of the lower and upper extremities. NHD disease course is generally divided into four stages: latent, osseous, early neurologic, and late neurologic. After a normal development during childhood (latent stage), NHD starts manifesting during adolescence or young adulthood (typical age of onset 20-30 years) with pain in the hands, wrists, ankles, and feet. Patients then start suffering from recurrent bone fractures due to polycystic osseous and osteoporotic lesions in the limb bones (osseous stage). During the third or fourth decade of life (early neurologic stage), patients present with pronounced personality changes (e.g., euphoria, lack of concentration, loss of judgment, and social inhibitions) characteristic of a frontal lobe syndrome. Patients also typically suffer from progressive memory disturbances. Epileptic seizures are also frequently observed. Finally (late neurologic stage), patients progress to a profound dementia, are unable to speak and move, and usually die by the age of 50.

Animal models have been developed to model various aspects of Nasu-Hakola disease, including, for example, increased bone mass (osteopetrosis), reduction of myelin (hypomyelinosis) accentuated in the thalamus, synaptic degeneration, impaired prepulse inhibition, and aberrant electrophysiological profiles in the thalami. Examples of animal models useful for modeling one or more signs or symptoms of Nasu-Hakola disease may include, without limitation, TYROBP$^{-/-}$ mice (See e.g., Kaifu, T. et al. (2003) *J Clin. Invest.* 111(3): 323-32).

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

Animal models have been developed to model various aspects of Parkinson's disease, including, for example, fragmented and dysfunctional mitochondria, altered mitophagy, ubiquitin proteasome dysfunction, altered reactive oxygen species production and calcium handling, alterations in motor function and behavior, and sensitivities to complex I toxins. Examples of animal models useful for modeling one or more signs or symptoms of Parkinson's disease may include, without limitation, toxin-based models (e.g., MPTP mice, MPTP monkeys, 6-OHDA rats, Rotenone, paraquat/maneb, MET/MDMA, etc.), genetic mutation models (e.g., mutations in α-synuclein, LRKK2, PINK1, PARKIN, DJ-1, ATP13A2, etc.), α-synuclein AAV virus injection model, α-synuclein preformed fibril injection model (See e.g., Luk, K C et al., *Science* 2012 Nov. 16; 338(6109): 949-953), and other models (SHH, Nurr1, Engrailed1, Pitx3, C-rel-NFKB, MitoPark, Atg7, VMAT2, etc.) (See e.g., Blesa, J. and Przedborski, J. (2014) *Front. Neuroanat.* 8: 155).

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin plays a role in ALS (Schymick, J C et al., (2007) J Neurol Neurosurg Psychiatry; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

Animal models have been developed to model various aspects of ALS, including, for example, axonal and mitochondrial dysfunction, progressive neuromuscular dysfunction, gliosis, and motor neuron loss. Examples of animal models useful for modeling one or more signs or symptoms of ALS may include, without limitation, genetic mutation models (e.g., mutations in SOD1, TDP-43, FUS, VCP, etc.), and the mouse models SOD1$^{G37R}$, SOD1$^{H46R}$, SOD1$^{G93A}$, TDP-43$^{WT}$, TDP-43$^{G348C}$, and FUS$^{R521C}$ (See e.g., Philips, T. and Rothstein, J. (2016) *Curr. Protoc. Pharmacol.* 69: 1-21).

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

Animal models have been developed to model various aspects of Huntington's disease, including, for example, production and aggregation of huntingtin protein in striatal neurons as well as neurons in other regions (such as the cortex, thalamus, hypothalamus, and substantia nigra pars compacta), involuntary hyperkinetic (choreaform) movements of the arms, legs, and/or face, and severe cognitive changes. Examples of animal models useful for modeling one or more signs or symptoms of ALS may include, without limitation, toxin-based models (e.g., quinolinic acid, 3-nitroproprionic acid, etc.), genetic mutation models (e.g., mutations in mouse, rat, or primate HTT, etc.), and the mouse models R6/2, R6/1, N171-82Q, and YAC (See e.g., Ramaswamy, S. et al. (2007) *ILAR J.* 48(4): 356-73).

Human Genes

Certain aspects of the present disclosure relate to transgenic non-human animals whose genomes comprise two or more of the human TREM1, TREML1, TREM2, TREML2, and TREML4 genes.

Human TREM1 Gene

In some embodiments, the genome of a transgenic non-human animal of the present disclosure comprises a human TREM1 gene. In some embodiments, the genome of the transgenic non-human animal comprises an inactivating mutation in the endogenous TREM1 gene. In some embodiments, the transgenic non-human animal comprises a non-functional endogenous TREM1 gene. In some embodiments, the genome of the transgenic non-human animal comprises a human TREM1 gene and lacks an endogenous TREM1 gene. In some embodiments, the genome of the transgenic non-human animal comprises a human TREM1 gene and a non-functional endogenous TREM1 gene. In some embodiments, the transgenic non-human animal is a mouse. In some embodiments, the genome of the mouse comprises an inactivating mutation in the endogenous murine TREM1 gene. In some embodiments, the genome of the mouse comprises a non-functional murine TREM1 gene. In some embodiments, the genome of the mouse comprises a human TREM1 gene and lacks an endogenous murine TREM1 gene. In some embodiments, the genome of the mouse comprises a human TREM1 gene and a non-functional murine TREM1 gene.

In some embodiments, the human TREM1 gene comprises all intronic and exonic sequences of the TREM1 gene encoded on chromosome 6 in the human genome. An exemplary polynucleotide comprising all intronic and exonic sequences of the TREM1 gene encoded on chromosome 6 in the human genome is NG_029525.2 RefSeqGene and/or NC_000006.12 (41267385 . . . 41286745, complement) Reference GRCh38.p7 Primary Assembly.

In some embodiments, the human TREM1 gene comprises a flanking sequence at the 5' end of the coding sequence for the humanTREM1 polypeptide. In some embodiments, the human TREM1 gene comprises a flanking sequence at the 3' end of the coding sequence for the human TREM1 polypeptide. In some embodiments, the human TREM1 gene comprises a flanking sequence at the 5' end and 3' end of the coding sequence for the human TREM1 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human TREM1 gene in one or more cells of the transgenic non-human animal. In some embodiments, the one or more human transcriptional regulatory elements direct expression of the human TREM1 gene and one or more additional genes in one or more cells of the transgenic non-human animal. In some embodiments, the one or more additional genes are one or more (e.g., one or more, two or more, three or more, or all four) of the human TREML1, TREM2, TREML2, and TREML4 genes. In some embodiments, the one or more human transcriptional regulatory elements direct coordinate expression of the human TREM1 gene and the one or more additional genes in one or more cells of the transgenic non-human animal. In some embodiments, the one or more cells of the transgenic non-human animal are one or more myeloid cells (e.g., macrophages, dendritic cells, osteoclasts, microglia, monocytes, Langerhans cells of skin, Kupffer cells, and any combinations thereof).

TREM1 is variously referred to as triggering receptor expressed on myeloid cells 1, triggering receptor expressed on monocytes1, and CD354.

An exemplary amino acid sequence of human TREM1 is SEQ ID NO: 1. In some embodiments, a human TREM1 gene of the present disclosure encodes a polypeptide comprising the sequence of SEQ ID NO: 1. In some embodiments, a human TREM1 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 1.

In some embodiments, a human TREM1 gene of the present disclosure encodes an N-terminal truncation, a C-terminal truncation, or a fragment of a polypeptide comprising the sequence of SEQ ID NO: 1. N-terminal truncations, C-terminal truncations, or fragments may comprise at least 10, at least 25, at least 50, at least 75, at least 100, at least 125, at least 150, at least 175, at least 200, at least 225, but fewer than 234, consecutive amino acids of SEQ ID NO: 1.

In some embodiments, a human TREM1 gene of the present disclosure encodes a polypeptide comprising the sequence of SEQ ID NO: 2. In some embodiments, a human TREM1 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 2.

In some embodiments, a human TREM1 gene of the present disclosure encodes an N-terminal truncation, a C-terminal truncation, or a fragment of a polypeptide comprising the sequence of SEQ ID NO: 2. N-terminal truncations, C-terminal truncations, or fragments may comprise at least 10, at least 25, at least 50, at least 75, at least 100, at least 125, but fewer than 150, consecutive amino acids of SEQ ID NO: 2.

In some embodiments, a human TREM1 gene of the present disclosure encodes a polypeptide comprising the sequence of SEQ ID NO: 3. In some embodiments, a human TREM1 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 3.

In some embodiments, a human TREM1 gene of the present disclosure encodes an N-terminal truncation, a C-terminal truncation, or a fragment of a polypeptide comprising the sequence of SEQ ID NO: 3. N-terminal truncations, C-terminal truncations, or fragments may comprise at least 10, at least 25, at least 50, at least 75, at least 100, at least 125, at least 150, at least 175, at least 200, but fewer than 225, consecutive amino acids of SEQ ID NO: 3.

In some embodiments, the human TREM1 gene encodes a polypeptide comprising one or more (e.g., one or more, two or more, three or more, or all four) mutations selected from: a threonine to serine mutation at a position corresponding to position 25 of SEQ ID NO: 1; an arginine to serine mutation at a position corresponding to position 97 of SEQ ID NO: 1; a lysine to threonine mutation at a position corresponding to position 135 of SEQ ID NO: 1; and a phenylalanine to leucine mutation at a position corresponding to position 214 of SEQ ID NO: 1.

Human TREML1 Gene

In some embodiments, the genome of a transgenic non-human animal of the present disclosure comprises a human TREML1 gene. In some embodiments, the genome of the transgenic non-human animal comprises an inactivating mutation in the endogenous TREML1 gene. In some embodiments, the genome of the transgenic non-human animal comprises a non-functional endogenous TREML1 gene. In some embodiments, the genome of the transgenic non-human animal comprises a human TREML1 gene and lacks an endogenous TREML1 gene. In some embodiments, the genome of the transgenic non-human animal comprises a human TREML1 gene and a non-functional endogenous TREML1 gene. In some embodiments, the transgenic non-human animal is a mouse. In some embodiments, the genome of the mouse comprises an inactivating mutation in the endogenous murine TREML1 gene. In some embodiments, the genome of the mouse comprises a non-functional murine TREML1 gene. In some embodiments, the genome of the mouse comprises a human TREML1 gene and lacks an endogenous murine TREML1 gene. In some embodiments, the genome of the mouse comprises a human TREML1 gene and a non-functional murine TREML1 gene.

In some embodiments, the human TREML1 gene comprises all intronic and exonic sequences of the TREML1 gene encoded on chromosome 6 in the human genome. An exemplary polynucleotide comprising all intronic and exonic sequences of the TREML1 gene encoded on chromosome 6 in the human genome is NC_000006.12 (41149097 . . . 41158450, complement) Reference GRCh38.p7 Primary Assembly.

In some embodiments, the human TREML1 gene comprises a flanking sequence at the 5' end of the coding sequence for the human TREML1 polypeptide. In some embodiments, the human TREML1 gene comprises a flanking sequence at the 3' end of the coding sequence for the human TREML1 polypeptide. In some embodiments, the human TREML1 gene comprises a flanking sequence at the 5' end and 3' end of the coding sequence for the human TREML1 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human TREML1 gene in one or more cells of the transgenic non-human animal. In some embodiments, the one or more human transcriptional regulatory elements direct expression of the human TREML1 gene and one or more additional genes in one or more cells of the transgenic non-human animal. In some embodiments, the one or more additional genes are one or more (e.g., one or more, two or more, three or more, or all four) of the human TREM1, TREM2, TREML2, and TREML4 genes. In some embodiments, the one or more human transcriptional regulatory elements direct coordinate expression of the human TREML1 gene and the one or more additional genes in one or more cells of the transgenic non-human animal. In some embodiments, the one or more cells of the transgenic non-human animal are one or more myeloid cells (e.g., macrophages, dendritic cells, osteoclasts, microglia, monocytes, Langerhans cells of skin, Kupffer cells, and any combinations thereof).

TREML1 is variously referred to as triggering receptor expressed on myeloid cells-like protein 1, Trem-like transcript 1 protein, TLT1, and TLT-1.

An exemplary amino acid sequence of human TREML1 is SEQ ID NO: 4. In some embodiments, a human TREML1 gene of the present disclosure encodes a polypeptide comprising the sequence of SEQ ID NO: 4. In some embodiments, a human TREML1 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 4.

In some embodiments, a human TREML1 gene of the present disclosure encodes an N-terminal truncation, a C-terminal truncation, or a fragment of a polypeptide comprising the sequence of SEQ ID NO: 4. N-terminal truncations, C-terminal truncations, or fragments may comprise at least 10, at least 25, at least 50, at least 75, at least 100, at least 125, at least 150, at least 175, at least 200, at least 225, at least 250, at least 275, at least 300, but fewer than 311, consecutive amino acids of SEQ ID NO: 4.

In some embodiments, a human TREML1 gene of the present disclosure encodes a polypeptide comprising the sequence of SEQ ID NO: 5. In some embodiments, a human TREML1 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 5.

In some embodiments, a human TREML1 gene of the present disclosure encodes an N-terminal truncation, a C-terminal truncation, or a fragment of a polypeptide comprising the sequence of SEQ ID NO: 5. N-terminal truncations, C-terminal truncations, or fragments may comprise at least 10, at least 25, at least 50, at least 75, at least 100, at least 125, at least 150, at least 175, but fewer than 199, consecutive amino acids of SEQ ID NO: 5.

In some embodiments, a human TREML1 gene of the present disclosure encodes a polypeptide comprising the sequence of SEQ ID NO: 6. In some embodiments, a human TREML1 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 6.

In some embodiments, a human TREML1 gene of the present disclosure encodes an N-terminal truncation, a C-terminal truncation, or a fragment of a polypeptide comprising the sequence of SEQ ID NO: 6. N-terminal truncations, C-terminal truncations, or fragments may comprise at least 10, at least 25, at least 50, at least 75, at least 100, at least 125, at least 150, at least 175, but fewer than 200, consecutive amino acids of SEQ ID NO: 6.

In some embodiments, the human TREML1 gene encodes a polypeptide comprising one or more (e.g., one or more, or two) mutations selected from: a leucine to valine mutation at a position corresponding to position 6 of SEQ ID NO: 4; and a histidine to proline mutation at a position corresponding to position 231 of SEQ ID NO: 4.

Human TREM2 Gene

In some embodiments, the genome of a transgenic non-human animal of the present disclosure comprises a human TREM2 gene. In some embodiments, the genome of the transgenic non-human animal comprises an inactivating mutation in the endogenous TREM2 gene. In some embodiments, the genome of the transgenic non-human animal comprises a non-functional endogenous TREM2 gene. In some embodiments, the genome of the transgenic non-human animal comprises a human TREM2 gene and lacks an endogenous TREM2 gene. In some embodiments, the genome of the transgenic non-human animal comprises a human TREM2 gene and a non-functional endogenous TREM2 gene. In some embodiments, the transgenic non-human animal is a mouse. In some embodiments, the genome of the mouse comprises an inactivating mutation in the endogenous murine TREM2 gene. In some embodiments, the genome of the mouse comprises a non-functional murine TREM2 gene. In some embodiments, the genome of the mouse comprises a human TREM2 gene and lacks an endogenous murine TREM2 gene. In some embodiments, the genome of the mouse comprises a human TREM2 gene and a non-functional murine TREM2 gene.

In some embodiments, the human TREM2 gene comprises all intronic and exonic sequences of the TREM2 gene encoded on chromosome 6 in the human genome. An exemplary polynucleotide comprising all intronic and exonic sequences of the TREM2 gene encoded on chromosome 6 in the human genome is NC_000006.12 (41158506 . . . 41163200, complement) Reference GRCh38.p7 Primary Assembly and/or NG_011561.1 RefSeqGene.

In some embodiments, the human TREM2 gene comprises a flanking sequence at the 5' end of the coding sequence for the human TREM2 polypeptide. In some embodiments, the human TREM2 gene comprises a flanking sequence at the 3' end of the coding sequence for the human TREM2 polypeptide. In some embodiments, the human TREM2 gene comprises a flanking sequence at the 5' end and 3' end of the coding sequence for the human TREM2 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human TREM2 gene in one or more cells of the transgenic non-human animal. In some embodiments, the one or more human transcriptional regulatory elements direct expression of the human TREM2 gene and one or more additional genes in one or more cells of the transgenic non-human animal. In some embodiments, the one or more additional genes are one or more (e.g., one or more, two or more, three or more, or all four) of the human TREM1, TREML1, TREML2, and TREML4 genes. In some embodiments, the one or more human transcriptional regulatory elements direct coordinate expression of the human TREM2 gene and the one or more additional genes in one or more cells of the transgenic non-human animal. In some embodiments, the one or more cells of the transgenic non-human animal are one or more myeloid cells (e.g., macrophages, dendritic cells, osteoclasts, microglia, monocytes, Langerhans cells of skin, Kupffer cells, and any combinations thereof).

TREM2 is variously referred to as TREM-2, TREM2a, TREM2b, TREM2c, triggering receptor expressed on myeloid cells-2a, and triggering receptor expressed on monocytes-2.

An exemplary amino acid sequence of human TREM2 is SEQ ID NO: 7. Human TREM2 proteins contain several domains, including without limitation, a signal peptide located at amino acid residues 1-18 of SEQ ID NO: 7. Human TREM2 contains an extracellular immunoglobulin-like variable-type (IgV) domain located at amino residues 29-112 of SEQ ID NO: 7; additional extracellular sequences located at amino residues 113-174 of SEQ ID NO: 7; a transmembrane domain located at amino residues 175-195 of SEQ ID NO: 7; and an intracellular domain located at amino residues 196-230 of SEQ ID NO: 7.

In some embodiments, a human TREM2 gene of the present disclosure encodes a polypeptide comprising the sequence of SEQ ID NO: 7. In some embodiments, a human TREM2 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 7.

In some embodiments, a human TREM2 gene of the present disclosure encodes an N-terminal truncation, a C-terminal truncation, or a fragment of a polypeptide comprising the sequence of SEQ ID NO: 7. N-terminal truncations, C-terminal truncations, or fragments may comprise at least 10, at least 25, at least 50, at least 75, at least 100, at least 125, at least 150, at least 175, at least 200, at least 225, but fewer than 230, consecutive amino acids of SEQ ID NO: 7.

In some embodiments, a human TREM2 gene of the present disclosure encodes a polypeptide comprising the sequence of SEQ ID NO: 8. In some embodiments, a human TREM2 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 8.

In some embodiments, a human TREM2 gene of the present disclosure encodes an N-terminal truncation, a C-terminal truncation, or a fragment of a polypeptide comprising the sequence of SEQ ID NO: 8. N-terminal truncations, C-terminal truncations, or fragments may comprise at least 10, at least 25, at least 50, at least 75, at least 100, at least 125, at least 150, at least 175, at least 200, but fewer than 219, consecutive amino acids of SEQ ID NO: 8.

In some embodiments, a human TREM2 gene of the present disclosure encodes a polypeptide comprising the sequence of SEQ ID NO: 9. In some embodiments, a human TREM2 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 9.

In some embodiments, a human TREM2 gene of the present disclosure encodes an N-terminal truncation, a C-terminal truncation, or a fragment of a polypeptide comprising the sequence of SEQ ID NO: 9. N-terminal truncations, C-terminal truncations, or fragments may comprise at least 10, at least 25, at least 50, at least 75, at least 100, at least 125, at least 150, at least 175, at least 200, but fewer than 222, consecutive amino acids of SEQ ID NO: 9.

In some embodiments, the human TREM2 gene encodes a polypeptide comprising one or more (e.g., one or more, two or more, three or more, four or more, five or more, six or more, or seven) mutations selected from: an arginine to histidine mutation at a position corresponding to position 47 of SEQ ID NO: 7; a threonine to arginine mutation at a position corresponding to position 96 of SEQ ID NO: 7; a threonine to lysine mutation at a position corresponding to position 96 of SEQ ID NO: 7; an aspartate to glycine mutation at a position corresponding to position 134 of SEQ ID NO: 7; a histidine to tyrosine mutation at a position corresponding to position 157 of SEQ ID NO: 7; a lysine to asparagine mutation at a position corresponding to position 186 of SEQ ID NO: 7; and a leucine to proline mutation at a position corresponding to position 211 of SEQ ID NO: 7.

Human TREML2 Gene

In some embodiments, the genome of a transgenic non-human animal of the present disclosure comprises a human TREML2 gene. In some embodiments, the genome of the transgenic non-human animal comprises an inactivating mutation in the endogenous TREML2 gene. In some embodiments, the genome of the transgenic non-human animal comprises a non-functional endogenous TREML2 gene. In some embodiments, the genome of the transgenic non-human animal comprises a human TREML2 gene and lacks an endogenous TREML2 gene. In some embodiments, the genome of the transgenic non-human animal comprises a human TREML2 gene and a non-functional endogenous TREML2 gene. In some embodiments, the transgenic non-human animal is a mouse. In some embodiments, the genome of the mouse comprises an inactivating mutation in the endogenous murine TREML2 gene. In some embodiments, the genome of the mouse comprises a non-functional murine TREML2 gene. In some embodiments, the genome of the mouse comprises a human TREML2 gene and lacks an endogenous murine TREML2 gene. In some embodiments, the genome of the mouse comprises a human TREML2 gene and a non-functional murine TREML2 gene.

In some embodiments, the human TREML2 gene comprises all intronic and exonic sequences of the TREML2 gene encoded on chromosome 6 in the human genome. An exemplary polynucleotide comprising all intronic and exonic sequences of the TREML2 gene encoded on chromosome 6 in the human genome is NC_000006.12 (41189749 . . . 41201233, complement) Reference GRCh38.p7 Primary Assembly.

In some embodiments, the human TREML2 gene comprises a flanking sequence at the 5' end of the coding sequence for the human TREML2 polypeptide. In some embodiments, the human TREML2 gene comprises a flanking sequence at the 3' end of the coding sequence for the human TREML2 polypeptide. In some embodiments, the human TREML2 gene comprises a flanking sequence at the 5' end and 3' end of the coding sequence for the human TREML2 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human TREML2 gene in one or more cells of the transgenic non-human animal. In some embodiments, the one or more human transcriptional regulatory elements direct expression of the human TREML2 gene and one or more additional genes in one or more cells of the transgenic non-human animal. In some embodiments, the one or more additional genes are one or more (e.g., one or more, two or more, three or more, or all four) of the human TREM1, TREML1, TREM2, and TREML4 genes. In some embodiments, the one or more human transcriptional regulatory elements direct coordinate expression of the human TREML2 gene and the one or more additional genes in one or more cells of the transgenic non-human animal. In some embodiments, the one or more cells of the transgenic non-human animal are one or more myeloid cells (e.g., macrophages, dendritic cells, osteoclasts, microglia, monocytes, Langerhans cells of skin, Kupffer cells, and any combinations thereof).

TREML2 is variously referred to as triggering receptor expressed on myeloid cells like protein 2, Trem-like transcript 2 protein, TLT2, TLT-2, C6orf76, and dJ238023.1

An exemplary amino acid sequence of human TREML2 is SEQ ID NO: 10. In some embodiments, a human TREML2 gene of the present disclosure encodes a polypeptide comprising the sequence of SEQ ID NO: 10. In some embodiments, a human TREML2 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 10.

In some embodiments, a human TREML2 gene of the present disclosure encodes an N-terminal truncation, a C-terminal truncation, or a fragment of a polypeptide comprising the sequence of SEQ ID NO: 10. N-terminal truncations, C-terminal truncations, or fragments may comprise at least 10, at least 25, at least 50, at least 75, at least 100, at least 125, at least 150, at least 175, at least 200, at least 225, at least 250, at least 275, at least 300, but fewer than 321, consecutive amino acids of SEQ ID NO: 10.

In some embodiments, the human TREML2 gene encodes a polypeptide comprising one or more (e.g., one or more, two or more, three or more, four or more, five or more, six or more, seven or more, or eight) mutations selected from: a glycine to cysteine mutation at a position corresponding to position 19 of SEQ ID NO: 10; an aspartate to glycine mutation at a position corresponding to position 23 of SEQ ID NO: 10; a valine to alanine mutation at a position corresponding to position 25 of SEQ ID NO: 10; a valine to methionine mutation at a position corresponding to position 50 of SEQ ID NO: 10; an arginine to lysine mutation at a position corresponding to position 59 of SEQ ID NO: 10; a threonine to serine mutation at a position corresponding to position 129 of SEQ ID NO: 10; a serine to glycine mutation at a position corresponding to position 144 of SEQ ID NO: 10; and a valine to isoleucine mutation at a position corresponding to position 285 of SEQ ID NO: 10.

Human TREML4 Gene

In some embodiments, the genome of a transgenic non-human animal of the present disclosure comprises a human TREML4 gene. In some embodiments, the genome of the transgenic non-human animal comprises an inactivating mutation in the endogenous TREML4 gene. In some embodiments, the genome of the transgenic non-human animal comprises a non-functional endogenous TREML4 gene. In some embodiments, the genome of the transgenic non-human animal comprises a human TREML4 gene and lacks an endogenous TREML4 gene. In some embodiments, the genome of the transgenic non-human animal comprises a human TREML4 gene and a non-functional endogenous TREML4 gene. In some embodiments, the transgenic non-human animal is a mouse. In some embodiments, the genome of the mouse comprises an inactivating mutation in the endogenous murine TREML4 gene. In some embodiments, the genome of the mouse comprises a non-functional murine TREML4 gene. In some embodiments, the genome of the mouse comprises a human TREML4 gene and lacks an endogenous murine TREML4 gene. In some embodiments, the genome of the mouse comprises a human TREML4 gene and a non-functional murine TREML4 gene.

In some embodiments, the human TREML4 gene comprises all intronic and exonic sequences of the TREML4 gene encoded on chromosome 6 in the human genome. An exemplary polynucleotide comprising all intronic and exonic sequences of the TREML4 gene encoded on chromosome 6 in the human genome is NC_000006.12 (41228292 . . . 41239386, complement) Reference GRCh38.p7 Primary Assembly.

In some embodiments, the human TREML4 gene comprises a flanking sequence at the 5' end of the coding sequence for the human TREML4 polypeptide. In some embodiments, the human TREML4 gene comprises a flanking sequence at the 3' end of the coding sequence for the human TREML4 polypeptide. In some embodiments, the human TREML4 gene comprises a flanking sequence at the 5' end and 3' end of the coding sequence for the human TREML4 polypeptide. In some embodiments, the flanking sequence is at least about 10,000, at least about 15,000, at least about 20,000, at least about 25,000, at least about 30,000, at least about 35,000, at least about 40,000, at least about 45,000, or at least about 50,000 base pairs in length. In some embodiments, the flanking sequence is at least about 10,000 base pairs in length.

In some embodiments, the flanking sequence comprises one or more (e.g., one or more, two or more, three or more, four or more, five or more, etc.) human transcriptional regulatory elements. In some embodiments, the one or more human transcriptional regulatory elements direct expression of the human TREML4 gene in one or more cells of the transgenic non-human animal. In some embodiments, the one or more human transcriptional regulatory elements direct expression of the human TREML4 gene and one or more additional genes in one or more cells of the transgenic non-human animal. In some embodiments, the one or more additional genes are one or more (e.g., one or more, two or more, three or more, or all four) of the human TREM1, TREML1, TREM2, and TREML2 genes. In some embodiments, the one or more human transcriptional regulatory elements direct coordinate expression of the human TREML4 gene and the one or more additional genes in one or more cells of the transgenic non-human animal. In some embodiments, the one or more cells of the transgenic non-human animal are one or more myeloid cells (e.g., macrophages, dendritic cells, osteoclasts, microglia, monocytes, Langerhans cells of skin, Kupffer cells, and any combinations thereof).

TREML4 is variously referred to as triggering receptor expressed on myeloid cells-like protein 4, Trem-like transcript 4 protein, TLT4, TLT-4.

An exemplary amino acid sequence of human TREML4 is SEQ ID NO: 11. In some embodiments, a human TREML4 gene of the present disclosure encodes a polypeptide comprising the sequence of SEQ ID NO: 11. In some embodiments, a human TREML4 gene of the present disclosure encodes a polypeptide having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or 100% identity to the sequence of SEQ ID NO: 11.

In some embodiments, a human TREML4 gene of the present disclosure encodes an N-terminal truncation, a C-terminal truncation, or a fragment of a polypeptide comprising the sequence of SEQ ID NO: 11. N-terminal truncations, C-terminal truncations, or fragments may comprise at least 10, at least 25, at least 50, at least 75, at least 100, at least 125, at least 150, at least 175, but fewer than 200, consecutive amino acids of SEQ ID NO: 11.

In some embodiments, the human TREML4 gene encodes a polypeptide comprising one or more (e.g., one or more, two or more, or three) mutations selected from: a tryptophan to arginine mutation at a position corresponding to position 73 of SEQ ID NO: 11; a threonine to lysine mutation at a position corresponding to position 146 of SEQ ID NO: 11; and a threonine to isoleucine mutation at a position corresponding to position 168 of SEQ ID NO: 11.

Gene Combinations

In some embodiments, the genome of a transgenic non-human animal of the present disclosure comprises two or more, three or more, four or more, or all five of the human TREM1, TREML1, TREM2, TREML2, and TREML4 genes.

In some embodiments, the genome of transgenic non-human animal comprises one or more polynucleotides encoding two or more human genes. In some embodiments, the two or more human genes are encoded on separate polynucleotides. In some embodiments, the two or more human genes are encoded on a single polynucleotide. In some embodiments, the one or more polynucleotides are bacterial artificial chromosomes (BACs).

In some embodiments, the genome of the transgenic non-human animal comprises two of the human TREM1, TREML1, TREM2, TREML2, and TREML4 genes. In some embodiments, the genome of the transgenic non-human animal comprises the human TREM1 and TREML1 genes; the human TREM1 and TREM2 genes; the human TREM1 and TREML2 genes; the human TREM1 and TREML4 genes; the human TREML1 and TREM2 genes; the human TREML1 and TREML2 genes, the human TREML1 and TREML4 genes; the human TREM2 and TREML2 genes; the human TREM2 and TREML4 genes; or the human TREML2 and TREML4 genes. In some embodiments, the two human genes are encoded on one or more BACs. In some embodiments, the two human genes are encoded on a single BAC.

In some embodiments, the genome of the transgenic non-human animal comprises three of the human TREM1, TREML1, TREM2, TREML2, and TREML4 genes. In some embodiments, the genome of the transgenic non-human animal comprises the human TREM1, TREML1, and TREM2 genes; the human TREM1, TREML1, and TREML2 genes; the human TREM1, TREML1, and TREML4 genes; the human TREM1, TREM2, and TREML2 genes; the human TREM1, TREM2, and TREML4 genes; the human TREM1, TREML2, and TREML4 genes; the human TREML1, TREM2, and TREML2 genes; the human TREML1, TREM2, and TREML4 genes; the human TREML1, TREML2, and TREML4 genes; and the human TREM2, TREML2, and TREML4 genes. In some embodiments, the three human genes are encoded on one or more BACs. In some embodiments, the three human genes are encoded on a single BAC.

In some embodiments, the genome of the transgenic non-human animal comprises four of the human TREM1, TREML1, TREM2, TREML2, and TREML4 genes. In some embodiments, the genome of the transgenic non-human animal comprises the human TREM1, TREML1, TREM2, and TREML2 genes; the human TREM1, TREML1, TREM2, and TREML4 genes; the human TREM1, TREML1, TREML2, and TREML4 genes; the human TREM1, TREM2, TREML2, and TREML4 genes; and the human TREML1, TREM2, TREML2, and TREML4 genes. In some embodiments, the four human genes are encoded on one or more BACs. In some embodiments, the four human genes are encoded on two BACs. In some embodiments, the four human genes are encoded on a single BAC.

In some embodiments, the genome of the transgenic non-human animal comprises the human TREM1, TREML1, TREM2, TREML2, and TREML4 genes. In some embodiments, the five human genes are encoded on one or more BACs. In some embodiments, the five human genes are encoded on a single BAC.

In some embodiments, the transgenic non-human animal is a rodent (e.g., a mouse or rat). In some embodiments, the transgenic non-human animal is a mouse. In some embodiments, the genome of the transgenic mouse comprises one or more (e.g., one or more, two or more, three or more, etc.) non-functional murine genes. In some embodiments, the one or more non-functional murine genes are one or more of the murine TREM1 gene, the murine TREML1 gene, the murine TREM2 gene, the murine TREML2 gene, the murine TREML4 gene, and any combinations thereof. In some embodiments, the genome of the transgenic mouse comprises a non-functional murine TREM1 gene, a non-functional murine TREML1 gene, a non-functional murine TREM2 gene, a non-functional murine TREML2 gene, and a non-functional murineTREML4 gene.

Methods

Certain aspects of the present disclosure relate to methods of screening candidate agents that bind to and/or modulate the function and/or activity of at least one of the human genes in the transgenic non-human animals; to methods of screening candidate agents to determine their effect on one or more activities and/or functions associated with expression of at least one of the human genes in the transgenic non-human animals; to methods of recapitulating a human TREM immune system in a non-human animal; and to methods of generating a non-human animal disease model comprising a human TREM repertoire.

Transgenic non-human animals of the present disclosure may be generated by any method known in the art. In some embodiments, the method comprises introducing one or more polynucleotides encoding two or more of the human TREM1, TREML1, TREM2, TREML2, and TREML4 genes into one or more cells of an animal (e.g., by pronuclear injection of purified polynucleotides into the zygote of an animal) to generate a founder transgenic non-human animal.

In some embodiments, the one or more polynucleotides are one or more bacterial artificial chromosomes (BACs). Once founder transgenic non-human animals are produced whose genome comprises two or more of the human TREM1, TREML1, TREM2, TREML2, and TREML4 genes, the founder animals may be bred, inbred, outbred, or crossbred to produce progeny (colonies) of the particular non-human animal. Examples of such breeding strategies may include, but are not limited to, outbreeding of the founder animals with more than one integration site in order to establish separate lines; inbreeding of separate lines in order to produce compound transgenic that express the transgenes at higher levels due to the effects of additive expression of each transgene; crossing of heterozygous transgenic animals to produce transgenic animals homozygous for a given integration site in order to both augment expression and eliminate the need for screening of animals by DNA analysis; crossing of separate homozygous lines to produce compound heterozygous or homozygous lines; and breeding animals to different inbred genetic backgrounds so as to examine effects of modifying alleles on expression of the transgenes and the physiological effects of expression.

Transgenic non-human animals are produced by introducing one or more transgenes into the germline of the transgenic animal. Methods of introducing DNA into cells are generally available and well-known in the art, and different methods of introducing transgenes may be used (See e.g., Hogan et al. *Manipulating the Mouse Embryo: A Laboratory Manual* Cold Spring Harbor Laboratory, 2$^{nd}$ edition, Cold Spring Harbor Laboratory (1994); U.S. Pat. Nos. 5,602,229; 5,175,384; 6,066,778; and 6,037,521). Technology used in developing transgenic animals include pronuclear microinjection (See e.g., Gordon, J. W. (1980) *PNAS* 77,7380-7384; U.S. Pat. No. 4,873,191), homologous recombination (targeted transgenesis by transferring embryonic stem cells into blastocysts; Thompson et al. (1989) *Cell* 56: 313-321), RNA interference (RNAi)/CRISPR-Cas/TALENs for silencing of specific gene function, retrovirus gene transfer into germ lines (See e.g., Van der Putten et al. (1985) *PNAS* 82: 6148-6152), electroporation of embryos (See e.g., Lo. (1983) *Mol. Cell. Biol.* 3: 1803-1814), and sperm-mediated gene transfer (See e.g., Lavitrano et al. (1989) *Cell* 57: 717-723).

Generally, the zygote is the best target for microinjection. In mice, for example, the male pronucleus reaches the size of approximately 20 μm in diameter, which allows reproducible injection of 1-2 pL of DNA solution. The use of zygotes as a target for gene transfer has a major advantage because, in most cases, the injected DNA will be incorporated into the host genome before the first cleavage. Consequently, nearly all cells of the transgenic non-human animal will carry the incorporated transgene(s). Generally, this will result in the efficient transmission of the transgene to offspring of the founder since 50% of the germ cells will harbor the transgene. The pronuclear microinjection method of producing a transgenic animal results in the introduction of linear DNA sequences into the chromosomes of the fertilized eggs. Bacterial artificial chromosome (BAC) containing the genes of interest, or an alternative plasmid construct containing the genes of interest, is injected into pronuclei (i.e., fertilized eggs at a pronuclear state). The manipulated pronuclei are subsequently injected into the uterus of a pseudopregnant female. Mice generated using this method can have on or multiple copies of the transgenes, which can be assayed by any method known in the art (e.g., by southern blot technology).

The transgenic non-human animals of the present disclosure may also be generated by introducing one or more targeting vectors into embryonic stem (ES) cells. ES cells may be obtained by culturing pre-implantation embryos in vitro under appropriate conditions (See e.g., Evans et al. (1981) *Nature* 292: 154-6; Bradley et al. (1984) *Nature* 309: 255-8; Gossler et al. (1986) *PNAS* 83: 9065-9; Robertson et al. (1986) *Nature* 322: 445-8). Transgenes may be efficiently introduced into ES cells by DNA transfection using a variety of methods known in the art, including, without limitation, electroporation, calcium phosphate co-precipitation, protoplast or spheroplast fusion, lipofection, polymer-based transfections, and DEAE-dextran-mediated transfection. Transgenes may also be introduced into ES cells by retrovirus-mediated transduction of by micro-injection. Such transfected ES cells may thereafter colonize an embryo following their introduction into the blastocoel of a blastocyst-stage embryo and contribute to the germ line of the resulting chimeric animals (See e.g., Jaenisch, (1988) *Science* 240: 1468-74). Prior to the introduction of transfected ES cells in the blastocoel, the transfected ES cells may be subjected to various selection protocols to enrich for ES cells that have integrated the transgenes if the transgenes provide a means for such a selection. Alternatively, PCR amplification may be used to screen for ES cells that have integrated the transgenes. This technique obviates the need for growth of the transfected ES cells under appropriate selective conditions prior to transfer in to the blastocoel.

Retroviral infection may also be used to introduce transgenes into a non-human animal. Examples of suitable retroviruses may include, but are not limited to, human immunodeficiency virus (HIV), murine Moloney leukemia virus (MoMuLV), murine Moloney sarcoma virus (MSV), Harvey sarcoma virus (HaSV), spleen necrosis virus (SNV), Rous sarcoma virus (RSV) and Friend virus (See also, WO95/02697). The developing non-human embryo may be cultured in vitro to the blastocyst stage. During this time, blastomeres may be targets for retroviral infection. Efficient infection of the blastomeres may be obtained by enzymatic treatment to remove the zona pellucida. The viral vector system used to introduce the transgenes is typically a replication-defective retrovirus carrying the transgenes. Transfection is easily and efficiently obtained by culturing the blastomeres on a monolayer of virus-producing cells. Alternatively, infection can be performed at a later stage. Virus or virus-producing cells may be injected into the blastocoel. Most of the founder animals will be mosaic for the transgenes since incorporation occurs only in a subset of the cells which formed the transgenic non-human animal. Furthermore, the founder animal may contain retroviral insertion of the transgenes at a variety of positions in the genome; these generally segregate in the offspring. In addition, it is also possible to introduce transgenes into the germ line by intrauterine retroviral infection of the midgestation embryo.

Viral vectors may be used to produce a transgenic animal. In some embodiments, the viral vectors are replication-defective viral vectors (i.e., they are unable to replicate autonomously in the target cell). Generally, the genome of the replication defective viral vectors which are used lack at least one region which is necessary for the replication of the virus in the infected cell. These regions may either be eliminated (in whole or in part) or be rendered non-functional by any technique known in the art. These may include, for example, the total removal, substitution, partial deletion, or addition of one or more bases to an essential (for replication) region. Such techniques may be performed in vitro or in situ, using the techniques of genetic manipulation or by treatment with one or more mutagenic agents. In some embodiments, the replication-defective virus retain the sequences of its genome which are necessary for encapsidating the viral particles. Methods of producing viral vectors comprising one or more transgenes are known in the art.

Methods of Screening Candidate Agents

Certain aspects of the present disclosure relate to methods of screening candidate agents in any of the transgenic non-human animals described herein.

In some embodiments, the method comprises administering one or more candidate agents to a transgenic non-human animal of the present disclosure, and determining whether the one or more candidate agents bind to and/or modulates the function and/or activity of at least one of the two or more human TREM1, TREML1, TREM2, TREML2, and TREML4 genes in the transgenic non-human animal.

In some embodiments, the method comprises administering one or more candidate agents to a transgenic non-human animal of the present disclosure, and determining the effect of the one or more candidate agents on one or more activities and/or functions associated with expression of at least one of the two or more human genes in the transgenic non-human animal. In some embodiments, the one or more candidate agents activates/enhances one or more activities and/or functions associated with expression of two or more (e.g., two or more, three or more, four or more) of the human TREM1, TREML1, TREM2, TREML2, and TREML4 genes in the transgenic non-human animal. In some embodiments, the one or more candidate agents inhibits one or more activities and/or functions associated with expression of two or more (e.g., two or more, three or more, four or more) of the human TREM1, TREML1, TREM2, TREML2, and TREML4 genes in the transgenic non-human animal.

In some embodiments, the one or more candidate agents are any of one or more, two or more, three or more, four or more, five or more, six or more, seven or more, eight or more, nine or more, or 10 or more candidate agents. In some embodiments, the one or more candidate agents are administered once to the transgenic non-human animal. In some embodiments, the one or more candidate agents are administered two or more (e.g., two or more, three or more, four or more, five or more, six or more, seven or more, eight or more, nine or more, or ten or more) times to the transgenic non-human animal. In some embodiments, the one or more candidate agents are administered at the same dose two or more times in the transgenic non-human animal. In some embodiments, the one or more candidate agents are administered at two or more different doses two or more times in the transgenic non-human animal.

In some embodiments, the one or more candidate agents are two or more candidate agents. In some embodiments, the two or more candidate agents are administered at the same time to the transgenic non-human animal. In some embodiments, the two or more candidate agents are administered sequentially to the transgenic non-human animal. In some embodiments, the two or more candidate agents target one or more of the human TREM1, TREML1, TREM2, TREML2, and TREML4 genes. In some embodiments, the two or more candidate agents target the same human gene (e.g., a first and second candidate agent target a single human gene; a first, second, and third candidate agent target a single human gene, etc.) In some embodiments, the two or more candidate agents target two or more of the human genes (e.g., the first candidate agent targets a first human gene, the second candidate agent targets a second human gene; the first candidate agent targets a first human gene, the second candidate agent targets a second human gene, the third candidate agent targets a third human gene, etc.). In some embodiments, the one or more candidate agents are three or more candidates agents, and at least two of the three or more candidate agents target the same human gene (e.g., a first and second candidate agent target a first human gene, a third candidate agent targets a second human gene, etc.).

Examples of candidate agents may include, but are not limited to, compounds that specifically inhibit TREM synthesis and/or release, antisense molecules directed to one or more TREMs, short interfering RNA (siRNA) molecules directed to one or more polynucleotides encoding one or more TREMs, antibodies (e.g., monospecific antibodies, bispecific antibodies) that bind to one or more TREMs, soluble TREM receptors (e.g., soluble TREM receptors that bind one or more TREM ligands), TREM-Fc fusion proteins, TREM immunoadhesins, compounds that specifically inhibit one or more TREM activities such as small molecule inhibitors and/or peptide inhibitors, compounds that specifically inhibit one or more TREMs from binding to one or more ligands, TREM structural analogs, RNA or DNA aptamers that binds one or more TREMs, compounds that inhibit the synthesis of one or more TREM ligands (e.g., sialic acid-containing glycans present on proteins or other molecules), compounds that promote TREM ligand degradation, and compounds that directly degrade one or more TREM ligands. In some embodiments, the one or more candidate agents are one or more antibodies.

Examples of candidate agents may also include, but are not limited to, compounds that specifically activate/enhance TREM synthesis and/or release, antibodies (e.g., monospecific antibodies, bispecific antibodies) that bind to one or more TREMs, soluble TREM receptors (e.g., soluble TREM receptors that bind one or more TREM ligands), TREM immunoadhesins, compounds that specifically activate/enhance one or more TREM activities such as small molecule activators and/or peptide agonists, compounds that specifically activate/enhance one or more TREMs binding to one or more ligands, TREM structural analogs, RNA or DNA aptamers that binds one or more TREMs, compounds that activate/enhance the synthesis of one or more TREM ligands (e.g., sialic acid-containing glycans present on proteins or other molecules), and compounds that inhibit TREM ligand degradation. In some embodiments, the one or more candidate agents are one or more antibodies.

In some embodiments, the effect of the one or more candidate agents is one or more of increasing or reducing cell surface levels of one or more polypeptides encoded by the human TREM1, TREML1, TREM2, TREML2 and TREML4 genes; enhancing or competing for binding with a natural ligand of one or more polypeptides encoded by the human TREM1, TREML1, TREM2, TREML2 and TREML4 genes; increasing or reducing expression of one or more anti-inflammatory mediators (e.g., cytokines) selected from the group consisting of IL-12p70, IL-6, and IL-10; increasing or reducing expression of one or more pro-inflammatory mediators selected from the group consisting of IFN-a4, IFN-b, IL-6, IL-12 p70, IL-1β, TNF, TNF-α, IL-10, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, and IL-18; increasing or reducing the expression of TNF-α, IL-6, or both; increasing or reducing extracellular signal-regulated kinase (ERK) phosphorylation; increasing or reducing expression of C—C chemokine receptor 7 (CCR7); induction or inhibition of microglial cell chemotaxis toward CCL19 and CCL21 expressing cells; increasing, normalizing or reducing the ability of bone marrow-derived dendritic cells to induce antigen-specific T-cell proliferation; induction or inhibition of osteoclast production, increasing or reducing rate of osteoclastogenesis, or both; increasing or reducing the survival and/or function of one or more of dendritic cells, macrophages, microglial cells, M1 macrophages and/or microglial cells, activated M1 macrophages and/or microglial cells, M2 macrophages and/or microglial cells, monocytes, osteoclasts, Langerhans cells of skin, and Kupffer cells; induction or inhibition of one or more types of clearance selected from the group consisting of apoptotic neuron clearance, nerve tissue debris clearance, non-nerve tissue debris clearance, bacteria or other foreign body clearance, disease-causing protein clearance, disease-causing peptide clearance, and disease-causing nucleic acid clearance; induction or inhibition of phagocytosis of one or more of apoptotic neurons, nerve tissue debris, non-nerve tissue debris, bacteria, other foreign bodies, disease-causing proteins, disease-causing peptides, or disease-causing nucleic acids. In certain embodiments, disease-causing proteins include, without limitation, amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides. In certain embodiments, disease-causing nucleic acids include, without limitation, antisense GGCCCC (G2C4) repeat-expansion RNA.

In some embodiments, the effect of the one or more candidate agents is one or more of normalization or inhibition of TREM2/DAP12-dependent gene expression; recruitment or inhibiting recruitment of Syk, ZAP70, or both to the TREM2/DAP12 complex; increasing or reducing Syk phosphorylation; increasing or reducing the expression of CD83 and/or CD86 on dendritic cells, macrophages, monocytes, and/or microglia; increasing or reducing the secretion of one or more inflammatory cytokines selected from the group consisting of TNF-α, IL-10, IL-6, MCP-1, IFN-α4, IFN-b, IL-1β, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, and IL-18; increasing or reducing expression of one or more inflammatory receptors; increasing or reducing phagocytosis by macrophages, dendritic cells, monocytes, and/or microglia under conditions of reduced levels of MCSF; increasing or reducing phagocytosis by macrophages, dendritic cells, monocytes, and/or microglia in the presence of normal levels of MCSF; increasing or reducing the activity of one or more TREM2-dependent genes; increasing or reducing the activity of one or more nuclear factor of activated T-cells (NFAT) transcription factors, and any combination thereof.

In some embodiments, the one or more candidate agents modulates one or more activities and/or functions associated with expression of two or more (e.g., two or more, three or more) of the human TREM1, TREML1, TREM2, TREML2 and TREML4 genes in the transgenic non-human animal. In some embodiments, the one or more candidate agents activates/enhances one or more activities and/or functions associated with expression of two or more (e.g., two or more, three or more) of the human TREM1, TREML1, TREM2, TREML2 and TREML4 genes in the transgenic non-human animal. In some embodiments, the one or more candidate agents inhibits one or more activities and/or functions associated with expression of two or more (e.g., two or more, three or more) of the human TREM1, TREML1, TREM2, TREML2 and TREML4 genes in the transgenic non-human animal. In some embodiments, the one or more activities and/or functions are one or more of immune cell suppression; decreased expression of one or more pro-inflammatory cytokines, optionally wherein the one or more pro-inflammatory cytokines are selected from a group consisting IFN-α4, IFN-beta, IL-1β, IL-1alpha, TNF-α, IL-6, IL-8, CRP, IL-20 family members, LIF, IFN-gamma, OSM, CNTF, GM-CSF, IL-11, IL-12, IL-17, IL-18, CRP, MCP-1, and MIP-1-beta; decreased expression of one or more pro-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; increased expression of one or more anti-inflammatory cytokines, optionally wherein the one or more anti-inflammatory cytokines are selected from the group consisting of IL4, IL10, IL13, IL35, IL16, TGF-beta, IL1ra, G-CSF, and soluble receptors for TNF, IFN-beta1a, IFN-beta1b, and IL6; increased expression of one or more anti-inflammatory cytokines in one or more cells selected from the group consisting of macrophages, neutrophils, NK cells, dendritic cells, bone marrow-derived dendritic cells, monocytes, osteoclasts, T cells, T helper cells, cytotoxic T cells, granulocytes, and microglial cells; inhibition of extracellular signal-regulated kinase (ERK) phosphorylation; decreasing tyrosine phosphorylation on one or more cellular proteins, optionally, wherein the one or more cellular proteins comprise ZAP-70 and the tyrosine phosphorylation occurs on Tyr-319 of ZAP-70; decreased expression of C—C chemokine receptor 7 (CCR7); inhibition of microglial cell chemotaxis toward CCL19-expressing and CCL21-expressing cells; decreasing T cell proliferation induced by one or more cells selected from the group consisting of dendritic cells, bone marrow-derived dendritic cells, monocytes, microglia, M1 microglia, activated M1 microglia, M2 microglia, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, and M2 NK cells; inhibition of osteoclast production, decreased rate of osteoclastogenesis, or both; decreasing survival of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; decreasing proliferation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting migration of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting one or more functions of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibiting maturation of one or more cells selected from the group consisting of dendritic cells, bone marrow-derived dendritic cells, macrophages, neutrophils, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, neutrophils, microglia, M1 microglia, activated M1 microglia, and M2 microglia; inhibition of one or more types of clearance selected from the group consisting of apoptotic neuron clearance, nerve tissue debris clearance, non-nerve tissue debris clearance, bacteria clearance, other foreign body clearance, disease-causing protein clearance, disease-causing peptide clearance, and tumor cell clearance; optionally wherein the disease-causing protein is selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides and the tumor cell is from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer; inhibition of phagocytosis of one or more of apoptotic neurons, nerve tissue debris, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells are from a cancer selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; inhibition of tumor cell killing by one or more of microglia, macrophages, neutrophils, NK cells, dendritic cells, bone marrow-derived dendritic cells, neutrophils, T cells, T helper cells, or cytotoxic T cells; inhibiting anti-tumor cell proliferation activity of one or more of microglia, macrophages, neutrophils, NK cells, dendritic cells, bone marrow-derived dendritic cells, neutrophils, T cells, T helper cells, or cytotoxic T cells; inhibition of anti-tumor cell metastasis activity of one or more of microglia, macrophages, neutrophils, NK cells, dendritic cells, bone marrow-derived dendritic cells, neutrophils, T cells, T helper cells, or cytotoxic T cells; inhibition of one or more ITAM motif containing receptors, optionally wherein the one or more ITAM motif containing receptors are selected from the group consisting of TREM1, TREM2, Sirp beta, FcgR, DAP10, and DAP12; inhibition of signaling by one or more pattern recognition receptors (PRRs), optionally wherein the one or more PRRs are selected from the group consisting of receptors that identify pathogen-associated molecular patterns (PAMPs), receptors that identify damage-associated molecular patterns (DAMPs), and any combination thereof; inhibition of one or more receptors comprising the motif D/Ex0-2YxxL/IX6-8YxxL/I (SEQ ID NO: 12); inhibition of signaling by one or more Toll-like receptors; inhibition of the JAK-STAT signaling pathway; inhibition of nuclear factor kappa-light-chain-enhancer of activated B cells (NFκB); de-phosphorylation of an ITAM motif containing receptor; decreased expression of one or more inflammatory receptors, optionally wherein the one or more inflammatory receptors comprise CD86 and the one or more inflammatory receptors are expressed on one or more of microglia, macrophages, neutrophils, NK cells, dendritic cells, bone marrow-derived dendritic cells, neutrophils, T cells, T helper cells, or cytotoxic T cells; decreasing expression of one or more ITAM-dependent genes, optionally wherein the one more ITAM-dependent genes are activated by nuclear factor of activated T cells (NFAT) transcription factors; promoting differentiation of one or more of immunosuppressor dendritic cells, immunosuppressor macrophages, immunosuppressor neutrophils, immunosuppressor NK cells, myeloid derived suppressor cells, tumor-associated macrophages, tumor-associated neutrophils, tumor-associated NK cells, and regulatory T cells; rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells into tumors; increasing the number of tumor-promoting myeloid/granulocytic immune-suppressive cells in a tumor, in peripheral blood, or other lymphoid organ; enhancing tumor-promoting activity of myeloid-derived suppressor cells; increasing expression of tumor-promoting cytokines in a tumor or in peripheral blood, optionally wherein the tumor-promoting cytokines are TGF-beta or IL-10; increasing tumor infiltration of tumor-promoting FoxP3+ regulatory T lymphocytes; enhancing tumor-promoting activity of myeloid-derived suppressor cells (MDSC); decreasing activation of tumor-specific T lymphocytes with tumor killing potential; decreasing infiltration of tumor-specific NK cells with tumor killing potential; decreasing the tumor killing potential of NK cells; decreasing infiltration of tumor-specific B lymphocytes with potential to enhance immune response; decreasing infiltration of tumor-specific T lymphocytes with tumor killing potential; increasing tumor volume; increasing tumor growth rate; increasing metastasis; increasing rate of tumor recurrence; decreasing efficacy of one or more immune-therapies that modulate anti-tumor T cell responses, optionally wherein the one or more immune-therapies are immune-therapies that target one or more target proteins selected from the group consisting of PD1/PDL1, CTLA4, CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, DR-5, and any combination thereof, or cancer vaccines; inhibition of PLCγ/PKC/calcium mobilization; inhibition of PI3K/Akt, Ras/MAPK signaling; and any combination thereof.

In some embodiments, the transgenic non-human animal suffers from a disease, disorder, and/or injury. In some embodiments, administering the one or more candidate agents reduced or eliminates one or more signs and/or symptoms of the disease, disorder, and/or injury. In some embodiments, the disease, disorder, and/or injury is one or more of autoimmunity, susceptibility to infection, cancer, proliferative disorders, and/or neurodegenerative disorders.

In some embodiments, the one or more diseases, disorders, and/or injuries is one or more of dementia, frontotemporal dementia (FTD), Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential Tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases.

Methods of Recapitulating a Human TREM Immune System

Certain aspects of the present disclosure relate to a method of recapitulating a human TREM immune system in a non-human animal. In some embodiments, the method comprises generating a transgenic non-human animal whose genome comprises two or more of the human TREM1, TREML1, TREM2, TREML2 and TREML4 genes. In some embodiments, the two or more human genes are coordinately expressed in one or more cells of the transgenic non-human animal. In some embodiments, the one or more cells of the transgenic non-human animal are one or more myeloid cells (e.g., macrophages, dendritic cells, osteoclasts, microglia, monocytes, Langerhans cells of skin, and Kupffer cells, and any combinations thereof). In some embodiments, the transgenic non-human animal comprising a recapitulated human TREM immune system is any of the transgenic non-human animals described herein. Methods of generating transgenic non-human animals are known in the art (e.g., by any of the methods described herein).

Without wishing to be bound by theory, it is thought that recapitulating a human TREM immune system in a non-human animal comprises the coordinate expression of multiple (i.e., two or more) human TREM genes in the non-human animal that mimics the cell-type specificity (e.g., myeloid lineages: monocytes, macrophages, dendritic cells, microglia, etc.) and gene expression (e.g., expression levels, cellular localization of the proteins at the cell surface, etc.) observed in the corresponding human cells. Furthermore, without wishing to be bound by theory, it is thought that coordinate expression of multiple human TREM proteins in non-human animals would allow these proteins to form heteromers (e.g., heterodimers, etc.) in the myeloid cells of the non-human animals, and that the myeloid cells expressing the human TREM genes would respond to the ligands of the human TREM proteins equivalently to human cells with respect to signaling, as well as the suppressive/activating functions of the human TREM proteins, thus recapitulating the human Trem immune system in a non-human animal.

Methods of Generating Non-Human Animal Disease Models with a Human TREM Repertoire Certain aspects of the present disclosure relate to methods of generating non-human disease models comprising a human TREM repertoire. In some embodiments, the method comprises introducing one or more genetic determinants of a disease into the genome of any of the transgenic non-human animals described herein.

In some embodiments, the disease is one or more of cancer (e.g., melanoma, acute myeloid leukemia, etc.), proliferative disorders, infectious diseases (e.g., bacterial infections), and/or neurodegenerative diseases. In some embodiments, the neurodegenerative diseases are one or more of dementia, frontotemporal dementia (FTD), Alzheimer's disease, Nasu-Hakola disease, Parkinson's disease, amyotrophic lateral sclerosis (ALS), Huntington's disease, taupathy disease, and/or multiple sclerosis. In some embodiments, the disease is Alzheimer's disease. In some embodiments, the proliferative disease is cancer.

In some embodiments, the one or more genetic determinants are introduced into the genome of the transgenic non-human animal by genetic manipulation. Methods of genetically manipulating animals are known in the art, including, for example, by the introduction of plasmids/cosmids, knock in/knock out technology, through the use of transposons/retrotransposons, the use of viruses (e.g., adenovirus, adeno-associated virus, herpes virus, Rous sarcoma virus, HIV, etc.), the use of the CRISPR/Cas system, the use of TALENs, the use of Zinc finger nucleases, etc.

In some embodiments, the one or more genetic determinants are introduced into the genome of the transgenic non-human animal by mating. In some embodiments, the transgenic non-human animal is mated with an animal that is heterozygous or homozygous for the one or more genetic determinants. In some embodiments, progeny from this mating are screened to identify animals comprising the one or more genetic determinants as well as two or more of the human TREM1, TREML1, TREM2, TREML2 and TREML4 genes. Methods of screening animals to identify animals comprising the one or more genetic determinants and the two or more human genes are known in the art (e.g., by PCR analysis, southern blot analysis, western blot analysis, FACS analysis, etc.).

In some embodiments, the one or more genetic determinants are one or more polynucleotides comprising a mutation. In some embodiments, the one or more mutations are one or more inactivating mutations. Examples of inactivating mutations may include, but are not limited to, deletions, insertions, point mutations, and rearrangements. In some embodiments, the one or more genetic determinants are one or more polynucleotides encoding one or more polypeptides comprising a mutation. In some embodiments, the one or more polypeptides comprising a mutation are one or more of amyloid precursor protein (APP), presenilin 1 (PS1), presenilin 2 (PS2), alpha-synuclein, serine/threonine-protein kinase PINK1, parkin, leucine-rich repeat serine/threonine protein kinase 2 (LRRK2), protein deglycase (DJ-1), probable cation-transporting ATPase 13A2 (ATP13A2), superoxide dismutase (SOD1), TAR DNA-binding protein 43 (TARDBP), RNA-binding protein FUS, translation endoplasmic reticulum ATPase (VCP), microtubule-associated protein tau, progranulin, protein C9orf72, charged multivesicular body protein 2b (CHMP2B), TYRO protein tyrosine kinase-binding protein (TYROBP), and any combinations thereof. In some embodiments, the polypeptide comprising a mutation is amyloid precursor protein (APP).

The present disclosure will be more fully understood by reference to the following Examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this disclosure and scope of the appended claims.

EXAMPLES

Example 1: Generation of Transgenic Mice Harboring Human TREM Genes

The purpose of the following example was to generate transgenic mice that coordinately express multiple human TREM family genes. The genomes of the mice were engineered to contain multiple human TREM transgenes under the control of their native human gene regulatory elements by introducing into the mouse genome Bacterial Artificial Chromosomes (BACs) encompassing the human locus containing the indicated TREM genes and their regulatory network. Without wishing to be bound by theory, it was believed that such mice would express the TREM genes in a human pattern of gene expression, the expressed protein would function appropriately, and the transgenic mice would allow for the development of therapeutics targeting human proteins.

Methodologies

Identifying BACs of Interest:

Bacterial Artificial Chromosomes (BACs) harboring the human TREM genes TREM1, TREML1, TREM2, TREML2, and TREML4 with all intronic and exonic sequences were identified using the UCSC genome browser and the CloneDB from NCBI. BAC clones were further selected to identify those clones harboring a minimum of at least 10 kilobases of 5' and 3' flanking sequences in addition to the indicated TREM genes to maximize the likelihood of identifying BAC clones that include the relevant human gene regulatory sequences in addition to human TREM1, TREML1, TREM2, TREML2, and TREML4.

Isolating and Purifying the BAC Clones:

BAC clones meeting all of the selection requirements were obtained from Invitrogen/Life Technologies/Fisher Scientific as bacterial stab cultures. The cultures were grown, and BAC DNA was isolated and purified using standard techniques. Agarose gel electrophoresis after restriction digestion was used to confirm size and intactness of the inserts.

Generating Transgenic Animals:

Mice harboring BAC clones of interest were generated by injecting the purified BAC DNA into mouse C57BL6/j zygotes by standard pronuclear injection techniques. Zygotes were returned to females, and the resulting pups were genotyped for the presence of the transgenes. Founder animals harboring the transgenes were then bred to non-transgenic animals, and progeny were screened for expression of the transgenes using standard techniques.

FACS Analysis:

Mice carrying the human TREM2 transgenes were analyzed by FACS analysis using standard techniques for expression of TREM1, TREM2 and TREML2. Briefly, peripheral blood was obtained from 4-8 week old transgenic animals; monocytes were isolated using standard techniques and were subjected to multi-color flow cytometry panel staining. Cells were incubated with the cell viability dye and indicated antibodies for 30 minutes on ice, washed twice with cold FACS buffer, and fixed with 4% PFA. The stained and fixed cells were then applied to a BD FACS CANTO II cytometer, data were acquired, and the resulting data was analyzed with the FlowJo software.

For experiments testing the expression of human TREM1, TREM2, and TREML2, monocytes were stained with a cell viability dye and the following anti-TREM2 antibodies with the following characteristics: #1, #6 and #7 bind to both human and murine TREM2; #2 and #3 are murine TREM2 specific and #4 and #5 are human specific TREM2 antibodies. The TREM-26 clone (Biolegend) was used to label human TREM2 and human TREML2 was labeled with anti-Tlt2 MIH60 (Biolegend).

Results

To obtain mice coordinately expressing multiple human TREM genes, Bacterial Artificial Chromosomes (BACs) harboring human TREM genes with sufficient flanking sequences were identified using the UCSC genome browser and the CloneDB from NCBI. BAC clone CTD-3222A20 was identified that was predicted to contain the coding sequences for the human genes TREM2, TREML2, TREM1, TREML1, and TREML4.

A map of the human region of interest encompassed by CTD-3222A20 is shown in FIG. 1 (from the UCSC genome browser). The chromosomal DNA within CTD-3222A20 spanned 187,519 nucleotides of the human genome, covering nucleotide positions 41,104,901-41,292,419 on human chromosome 6, based on the hg38 build of the UCSC genome browser (the human TREM genes are found within a cluster on chromosome 6). Clone CTD-3222A20 was tested via restriction digest/gel electrophoresis, the intactness and expected size of the human DNA insert was confirmed. Sequences of the ends of the BAC clone were confirmed. Sequences within the TREM1 and TREM2 genes were confirmed by PCR amplification and Sanger sequencing.

Transgenic mice harboring CTD-3222A20 were generated by pronuclear injection of the BAC DNA into C57BL6/j zygotes. The resulting pups were genotyped to identify founder animals harboring the human transgenes. These founder animals were then bred to non-transgenic animals and the progeny were analyzed by FACS analysis to monitor human TREM1, TREM2, and TREML2 protein expression.

Taken together, this data suggested that transgenic animals were successfully generated that both carried human genes from the TREM family and were capable of coordinately expressing genes from this family.

Example 2: Analysis of TREM2 Expression on Peritoneal Macrophages Isolated from the TREM Transgenic Mice Methodologies Isolation of Peritoneal Cavity Cells:

Peritoneal cavity cells were isolated from two wild-type mice (WT-1 and WT-2) and two TREM transgenic mice (Bac-1 and Bac-2) using standard techniques. Briefly, 5 mL of 3% (w/v) Brewer thioglycollate medium was injected into the peritoneal cavity of each mouse. After allowing inflammatory response to proceed for four days, peritoneal cavity cells were isolated and subjected to multi-color flow cytometry panel staining.

FACS Analysis:

Isolated peritoneal cavity cells were incubated with a cell viability dye (Aqua dye) and the indicated antibodies for 30 minutes on ice, washed twice with cold FACS buffer, and fixed with 4% PFA. The following antibodies were used: anti-mouse CD11b, anti-mouse F4/80, TREM2 antibodies anti-TREM2 antibody #1, anti-TREM2 antibody #2, anti-TREM2 antibody #3, anti-TREM2 antibody #4, and anti-TREM2 antibody #5, anti-TREM2 antibody #6, anti-TREM2 antibody #7. The stained and fixed cells were then applied to a BD FACS CANTO II cytometer, data were acquired, and the resulting data was analyzed with FlowJo software.

Results

Figure 2:
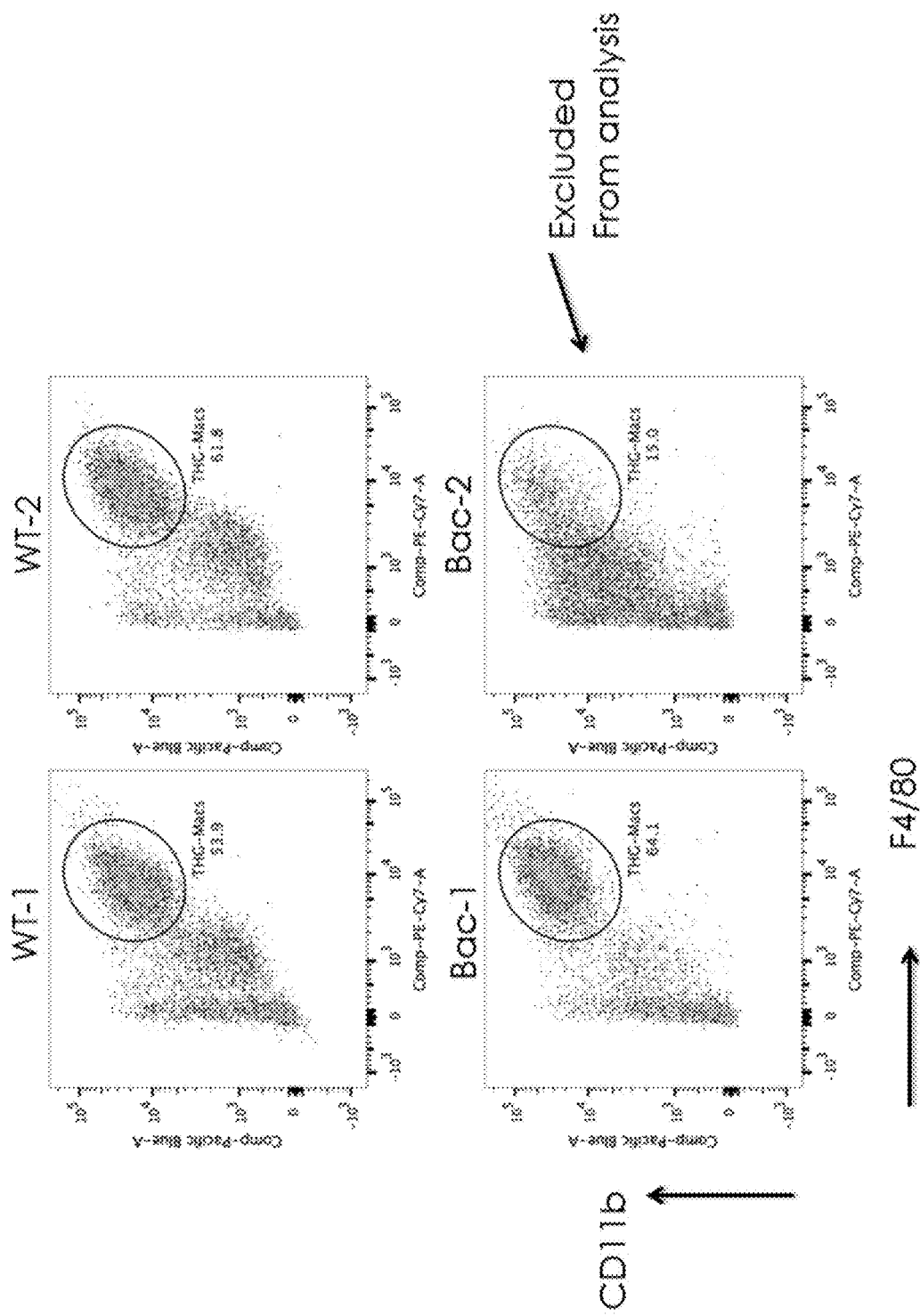
FIG. 2 shows results of FACS analysis demonstrating the expression pattern of CD11b and F4/80 on peritoneal cavity cells from both wild-type (WT-1, WT-2) and CTD-3222A20 transgenic (Bac-1, Bac-2) mice. Numbers indicate the percentage of peritoneal cavity cells sorted as macrophages.

FIG. 2 depicts FACS analysis plots with the expression of F4/80 on the X axis and the expression of CD11b on the Y axis. The percentages of CD11b-positive and F4/80-positive macrophages (highlighted by the circles) isolated from WT-1 and WT-2 mice were 53.9% and 61.8%, respectively. In the Bac-1 transgenic mouse, 64.1% of the isolated peritoneal cavity cells were CD11b-positive and F4/80-positive macrophages. Surprisingly, a low percentage of macrophages (15.0%) were detected in the other transgenic mouse, Bac-2. This suggests that there is no global change in the percentage of peripheral macrophages due to overexpression of the human TREM genes.

Figure 3:
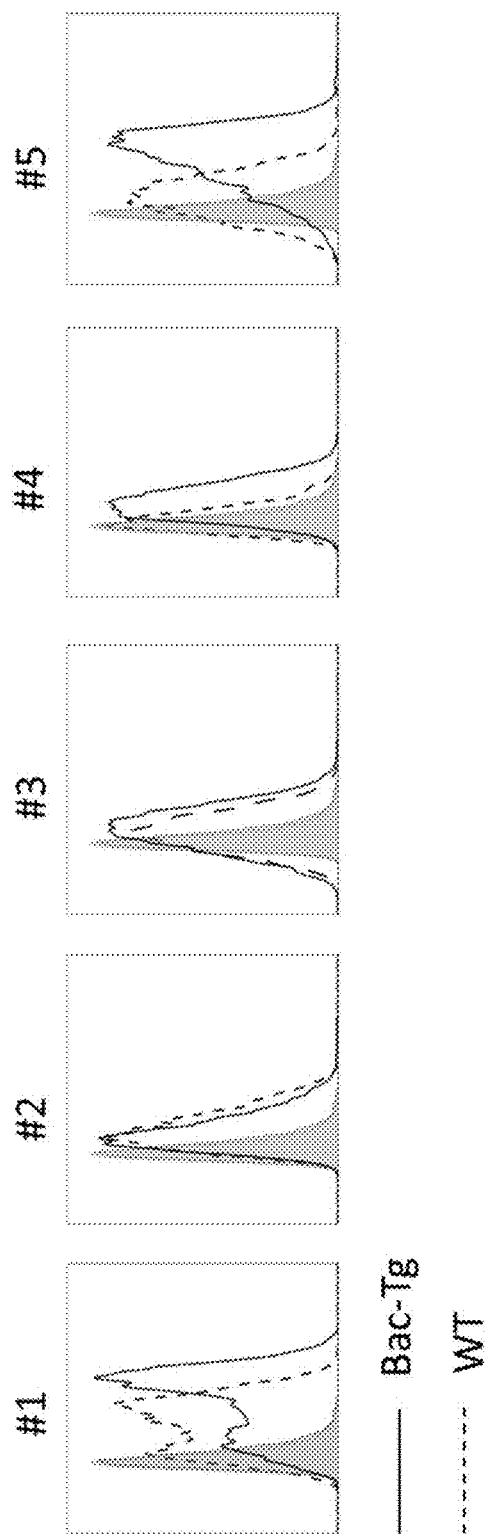
FIG. 3 shows FACS histograms demonstrating binding of anti-TREM2 antibodies (anti-TREM2 antibody #1, anti-TREM2 antibody #2, anti-TREM2 antibody #3, anti-TREM2 antibody #4, and anti-TREM2 antibody #5) to peritoneal macrophages isolated from wild-type and CTD-3222A20 transgenic (Bac) mice. Grey shaded and black outlined histograms indicate TREM2 staining on wild-type macrophages, and red shaded histograms indicate TREM2 staining on macrophages from CTD-3222A20 transgenic mice. Antibodies #2 and #3 bind murine TREM2, antibody #1 binds both murine and human TREM2, antibodies #4 and #5 bind only human TREM2.

FIG. 3 depicts FACS analysis plots indicating the level of TREM2 expression detected with different TREM2 antibodies. Expression of TREM2 was observed on peritoneal macrophages from TREM transgenic mice as indicated by positive TREM2 antibody staining (red shaded area). Macrophages from the wild-type mouse stained positive for TREM2 expression with TREM2 antibodies anti-TREM2 antibody #1, anti-TREM2 antibody #2, anti-TREM2 antibody #3, which are either murine TREM2 specific or human murine crossreactive. This suggests that both WT and TREM BAC Tg mice do express murine TREM2 on the cell surface. Macrophages from the TREM transgenic mouse stained positive for TREM2 expression with TREM2 antibodies anti-TREM2 antibody #1 and anti-TREM2 antibody #5, which are either human murine cross-reactive (antibody #1) or human TREM2 specific (antibody #5) (FIG. 3). Taken together, these results demonstrate that macrophages isolated from TREM transgenic mouse express detectable levels of human TREM2, while maintaining expression of murine TREM2.

Figures 13A, 13B:
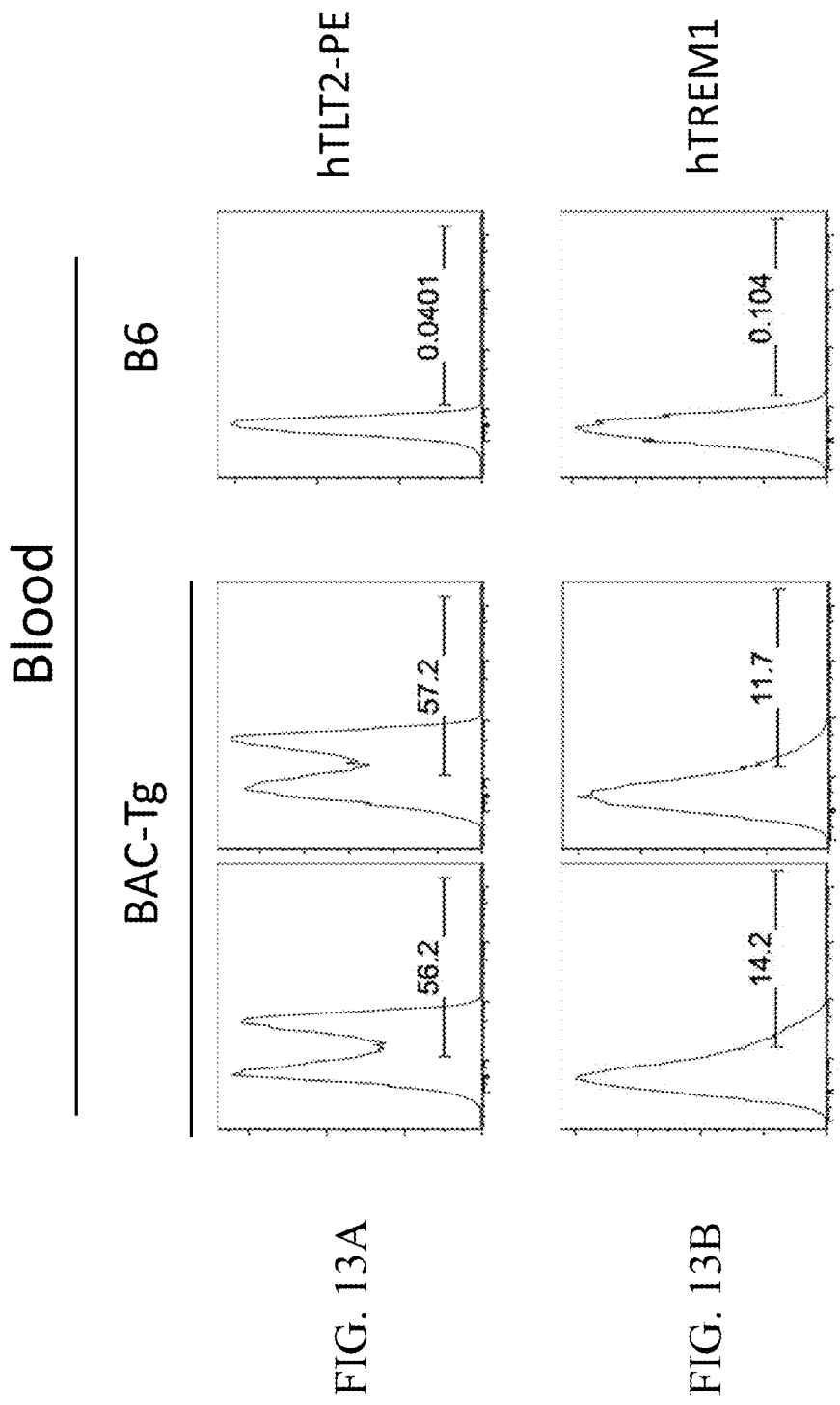
FIGS. 13A-13B show that TREM transgenic (BAC) mice express TREML2 and TREM1.

FIGS. 13A and 13B show that human TREM bac transgenic mice also express human TREML2 and human TREM1 in CD11b positive cells isolated from peripheral blood samples. These results indicate that the bac transgenic mice expresses TREM1, TREM2 and TREML2.

Example 3: TREM2 Antibodies Induce Cytokine Production by Peritoneal Macrophages from TREM Transgenic Mice Methodologies
Isolation of Peritoneal Macrophages:
Peritoneal cavity cells were isolated from two wild-type mice (WT-1 and WT-2) and two TREM transgenic mice (Bac-1 and Bac-2) as described in Example 2 above.
CCL2 and TNFα Production Analysis:
Conditioned media was harvested 24 hours or 60 hours after plating of peritoneal macrophages treated with anti-TREM2 antibodies or MOPC21 control antibody. Cytokines CCL2 and TNFα were measured using a CBE bead cytokine kit (BD Biosciences), according to manufacturer's instructions.
Results
FIGS. 4A-4B depict the levels of CCL2 produced after treatment with the indicated anti-TREM2 and control antibodies for 24 and 60 hours, respectively. Treatment with the anti-TREM2 antibody anti-TREM2 antibody #2 for both 24 and 60 hours increased CCL2 production from both wild-type macrophages and macrophages isolated from a TREM transgenic mouse.
FIGS. 4C-4E depict the levels of TNFα produced after treatment with the indicated anti-TREM2 and control antibodies for 24 and 60 hours, respectively. Without antibody stimulation, TNFα secretion is higher in the TREM Bac Tg mice compared to wildtype controls. Incubation with the anti-TREM2 antibody anti-TREM2 antibody #2 for 24 hours and 60 hours induced a further increase in TNFα production in both wild-type macrophages and macrophages from the TREM transgenic mouse. Surprisingly, anti-TREM2 antibodies #6, #7, and #4 all induced TNFα production at the 24 hour time point in macrophages from the TREM transgenic mouse, while TNFα levels remained elevated for 60 hours after treatment with the #2 and #4 antibodies. Since antibody #4 does not cross-react to murine TREM2, these data suggest that activation of human TREM2 by a TREM2-specific antibody in the Bac Tg mice can stimulate TNFα secretion.

Taken together, these results indicate that anti-TREM2 antibodies are capable of inducing the production of cytokines, such as CCL2 and TNFα, in peritoneal macrophages isolated from TREM transgenic mice, suggesting that human TREM2 in the Bac Tg mice can bind to murine Dap12 and induce expression of cytokines.

Figure 5:
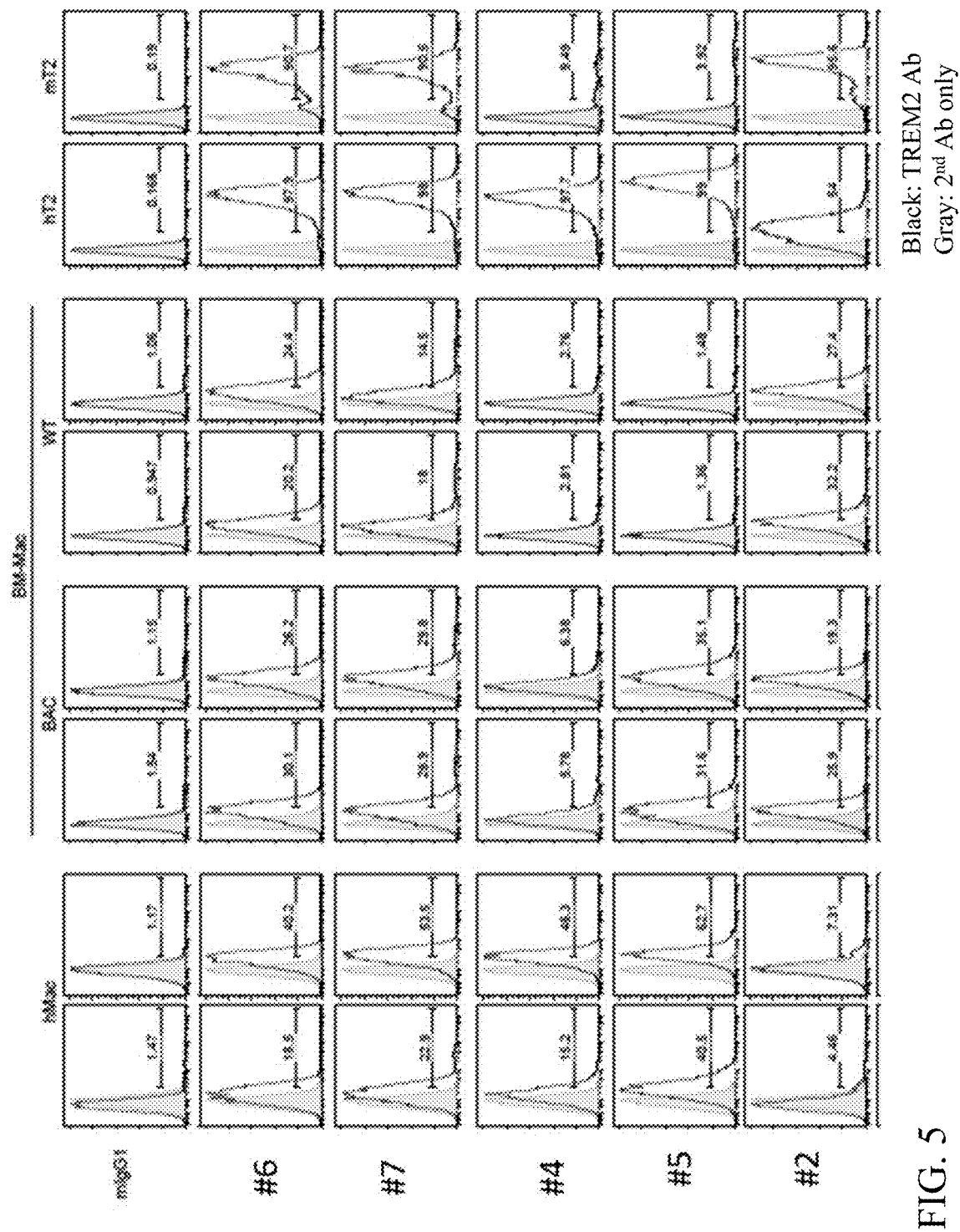
FIG. 5 shows FACS histograms demonstrating binding of anti-TREM2 antibodies (anti-TREM2 antibody #6, anti-TREM2 antibody #7, anti-TREM2 antibody #4, anti-TREM2 antibody #5, anti-TREM2 antibody #2) and control antibody (mIgG1) to primary human macrophages (hMac), bone marrow-derived macrophages (BM-Macs) from wild-type and CTD-3222A20 transgenic (BAC) mice, and hT2 and mT2 cell lines that express mouse and/or human TREM2. Shaded histograms represent negative controls using secondary antibody alone, and black outlined histograms represent TREM2 staining. Numbers indicate the percentage of cells identified as being TREM2-positive.

Example 4: Characterization of TREM2 Antibody Binding to TREM2 Expressed on Cells from TREM Transgenic Mice Methodologies
hMac:
Murine bone marrow precursor cells from TREM2-KO and TREM2-WT were obtained by flushing tibial and femoral marrow cells with cold PBS containing 2% FBS. Red blood cells were lysed using ACK lysing buffer, washed twice with 2% FBS/PBS and resuspended in complete media (RPMI, 10% FBS, Pen/Strep, L-glutamine, non-essential amino acid) with 50 ng/ml murine M-CSF (m-MCSF) to differentiate macrophages for 6 days.
BMDMs (BM-Macs):
Bone marrow-derived macrophages (BMDMs or BM-Macs) were generated in vitro using standard techniques. Briefly, total bone marrow from wild-type mice (WT) and TREM transgenic mice (BAC) were cultured in DMEM supplemented with 10% bovine calf serum, 5% horse serum, and 6 ng/mL recombinant human CSF-1 (R&D Systems). Cells were cultured for 5-6 days, and adherent cells were detached with 1 mM EDTA in PBS.
hT2 and msT2 Cell Lines:
The cell line BW5147.G.1.4 (ATCC® TIB48™), derived from mouse thymus lymphoma T lymphocytes, was infected with a virus carrying human or mouse TREM2 together with human or mouse DAP12, respectively, on a Puromycin selectable plasmid. Puromycin was used for positive selection and human TREM2 expression was validated using FACS.
hDC:
Human monocytes were isolated from whole blood using RosetteSep Human monocyte enrichment cocktail (Stemcell technologies) and Ficoll centrifugation per manufacturer protocols. After lysing red blood cells with ACK lysing buffer, monocytes were resuspended in complete media (RPMI, 10% FBS, Pen/Strep, L-glutamine, HEPES, non-essential amino acid, Sodium pyruvate) with 100 ng/ml human GM-CSF (hu-GMCSF) and human IL-4 (hu-IL-4) to differentiate dendritic cells for 6 days.
BMDCs:
Bone marrow-derived dendritic cells (BMDCs) were generated in vitro using standard techniques. Briefly, total bone marrow from wild-type mice (WT) and TREM transgenic mice (BAC) were cultured in DMEM supplemented with 10% bovine calf serum, 5% horse serum, and 6 ng/mL GM-CSF (R&D Systems). Cells were cultured for 5-6 days, and adherent cells were detached with 1 mM EDTA in PBS.
Results
The ability of TREM2 antibodies to bind TREM2 expressed on human macrophages, BM-Macs from wild-type and TREM transgenic mice, as well as hT2 and mT2 cell lines was determined (FIG. 5).

Anti-TREM2 antibodies anti-TREM2 antibody #6, anti-TREM2 antibody #7, anti-TREM2 antibody #4, and anti-TREM2 antibody #5 showed higher levels of binding to bone marrow-derived macrophages isolated from the TREM transgenic mice than bone marrow-derived macrophages isolated from wild-type mice. All these antibodies bind to human TREM2 as shown on the second to right column in FIG. 5. Antibody anti-TREM2 antibody #2 bound to macrophages from wild-type mice to a similar extent as to macrophages from the TREM transgenic mice. Anti-TREM2 antibody #2 only binds to murine TREM2, as indicated in the last column of FIG. 5.

Figure 6:
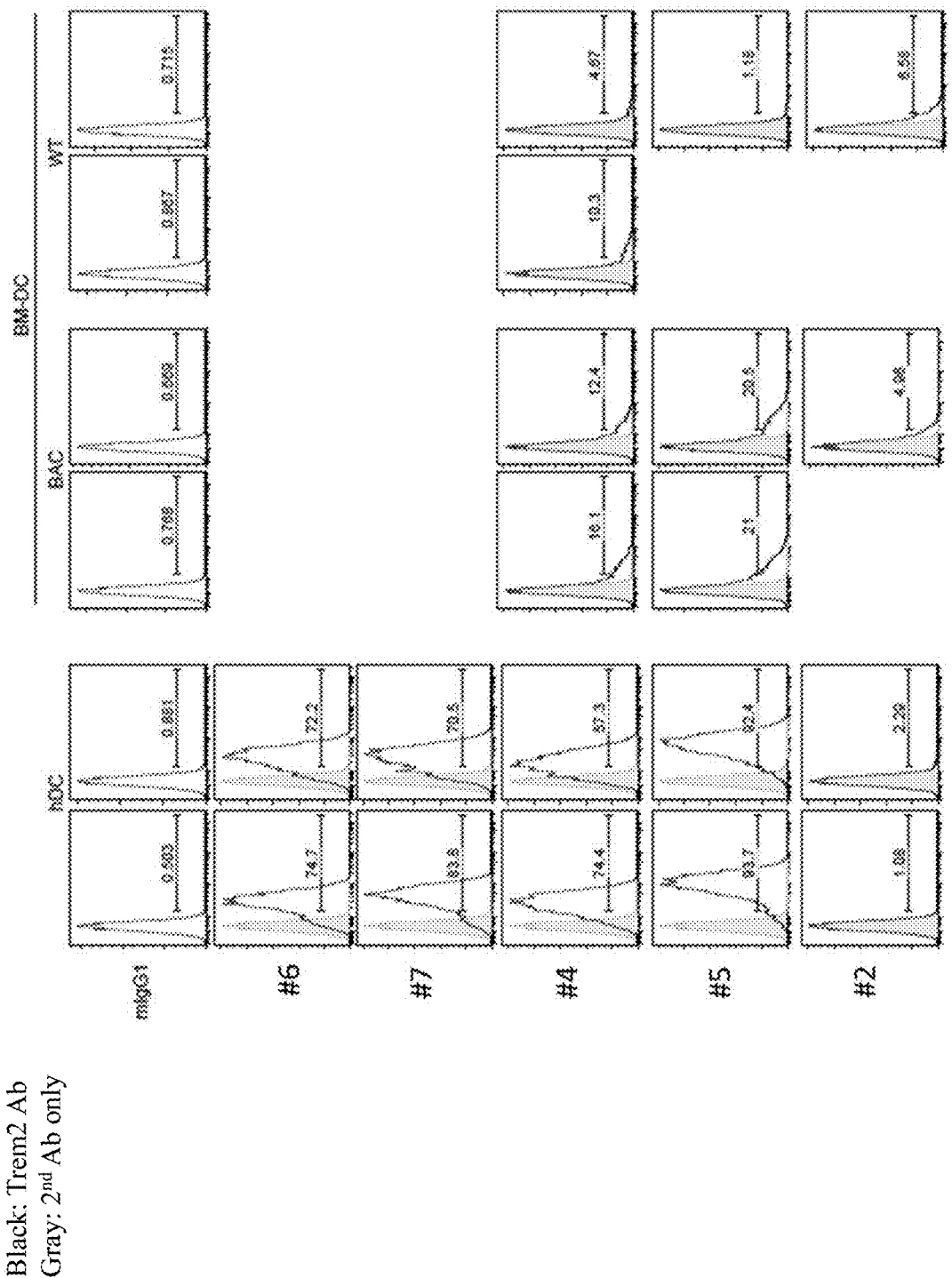
FIG. 6 shows FACS histograms demonstrating binding of anti-TREM2 antibodies (anti-TREM2 antibody #6, anti-TREM2 antibody #7, anti-TREM2 antibody #4, anti-TREM2 antibody #5, and anti-TREM2 antibody #2) and control antibody (mIgG1) to primary human dendritic cells (hDC), as well as bone marrow-derived dendritic cells (BM-DCs) isolated from wild-type and CTD-3222A20 transgenic (BAC) mice. Shaded histograms represent negative controls using secondary antibody alone. Black outlined histograms represent TREM2 staining. Numbers indicate the percentage of cells identified as being TREM2-positive.

Similarly, the ability of TREM2 antibodies to bind TREM2 expressed on primary human dendritic cells (hDC), as well as on bone marrow-derived dendritic cells isolated from wild-type and TREM transgenic mice were tested (FIG. 6). Antibody anti-TREM2 antibody #2 bound to BMDCs from both the wild-type and TREM transgenic mice at low levels (with a slightly higher affinity for the dendritic cells from wild-type mice). Antibodies anti-TREM2 antibody #4 and anti-TREM2 antibody #5 demonstrated preferential binding to BMDCs isolated from the TREM transgenic mice (expressing human TREM2), as compared to wild-type BMDCs. This is in line with them being specific for human TREM2 and not cross-reacting with murine TREM2.

Taken together, these results indicate that human TREM2 was successfully expressed on bone marrow-derived macrophages and dendritic cells from the TREM transgenic mice, and a subset of TREM2 antibodies, such as antibodies anti-TREM2 antibody #4 and anti-TREM2 antibody #5, were capable of binding human TREM2 expressed on mouse cells.

Example 5: TREM2 Antibodies Induce DAP12 Phosphorylation in Macrophages from TREM Transgenic Mice TREM2 was originally cloned as a cDNA encoding a TREM1 homologue (Bouchon, A. et al., (2001) *J. Exp. Med.* 194(8): p. 1111-22). The cytoplasmic tail of TREM2 lacks signaling motifs and is thought to signal through the signaling adaptor molecule DAP12/TRYROBP. Several recent studies have explored the intracellular signaling events induced by the activation of the TREM2/DAP12 pathway. For example, TREM2 is thought to activate signaling pathways involved in cell survival (e.g., protein kinase B-Akt), cell activation and differentiation (e.g., Syk, Erk1/2, PLC-γ, etc.), and in the control of the actin cytoskeleton (e.g., Syk, Vav, etc.) (Peng, Q et al., Sci Signal. 3(122): p. ra38; and Whittaker, G C et al., J Biol Chem. 285(5): p. 2976-85). After ligation of TREM2, the ITAM tyrosines in DAP12 are phosphorylated by SRC-family kinases leading to the recruitment and activation of the Syk kinase and/or ZAP70 kinase. In the mouse, Syk may be the predominant kinase involved, whereas in humans both Syk and ZAP70 appear to couple efficiently with such ITAM-containing subunits, binding them through their tandem SH2 domains.

Methodologies
BMDMs:
Bone marrow-derived macrophages (BMDMs) were generated as described in Example 2 above.

Antibody Stimulation and Co-Immunoprecipitation:
Before stimulation with antibodies, BMDMs derived from wild-type mice, TREM2 knockout mice (TREM2−/−), and TREM transgenic mice (Bac-Tg1 and Bac-2) were starved for 4 hours in 1% serum RPMI. 15×10$^6$ cells were incubated on ice for 15 minutes with anti-TREM2 or IgG1 isotype control antibodies. Cells were washed and incubated at 37° C. for the indicated period of time in the presence of goat anti-human IgG. After stimulation, cells were lysed with lysis buffer (1% v/v NP-40%, 50 Mm Tris-HCl (pH 8.0), 150 mM NaCl, 1 mM EDTA, 1.5 mM MgCl$_2$, 10% glycerol, plus protease and phosphatase inhibitors), followed by centrifugation at 16,000 g for 10 min at 4° C. to remove insoluble materials. Cell lysate was immunoprecipitated with a second TREM2 antibody (R&D Systems). Precipitated proteins were fractionated by SDS-PAGE, transferred to PVDF membranes, and probed with anti-phosphotyrosine antibody (4G10, Millipore). The membrane was stripped and reprobed with anti-DAP12 antibody (Cells Signaling, D7G1X).

Figure 7:
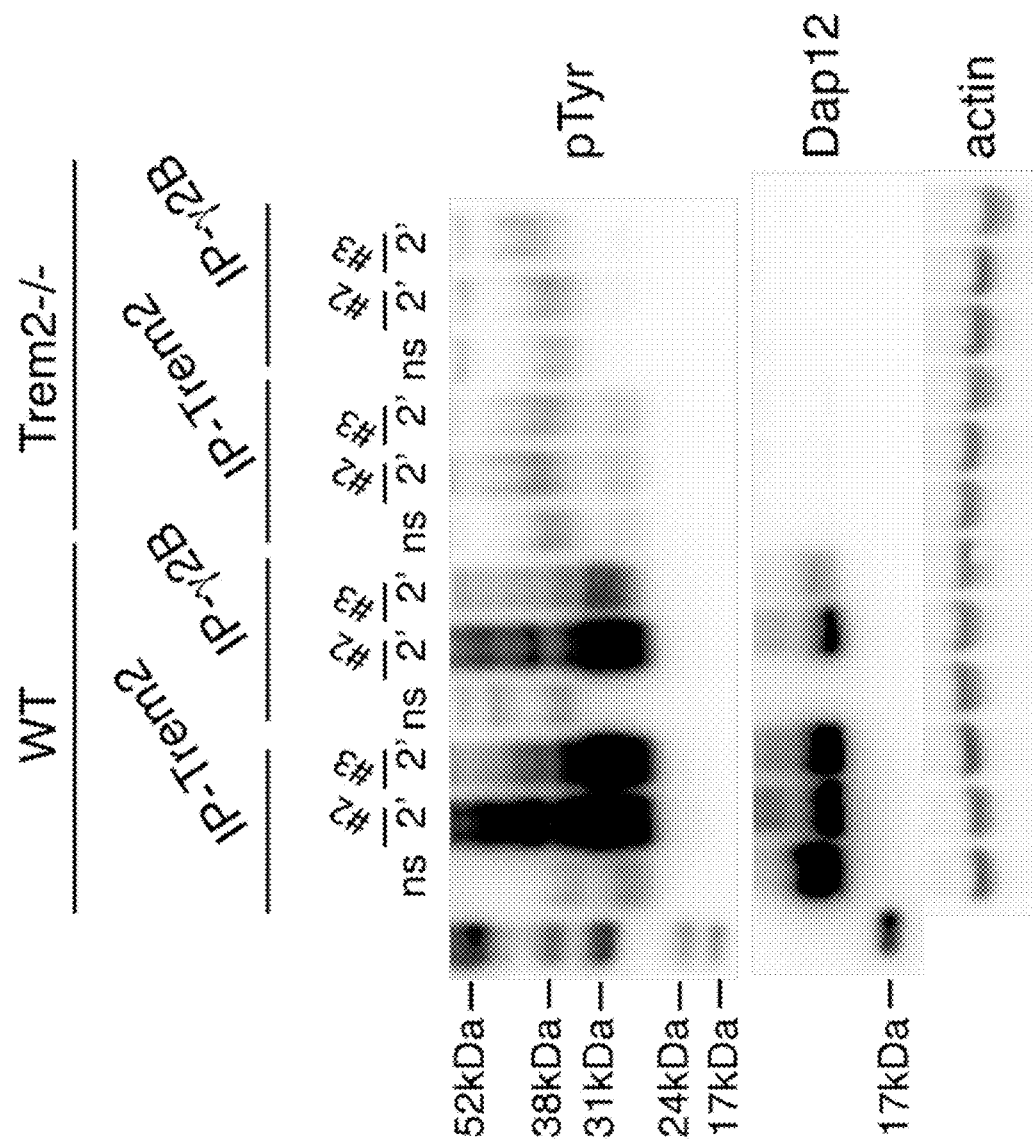
FIG. 7 shows DAP12 phosphorylation as determined by western blot analysis in wild-type and TREM2 deficient (TREM2−/−) mouse macrophages after incubation with anti-TREM2 antibodies (anti-TREM2 antibody #2 and anti-TREM2 antibody #3).

Results
The effects of anti-TREM2 antibodies, and the interplay between TREM2 and Dap12, were tested. DAP12 was found to co-precipitate with TREM2 in macrophages isolated from wild-type mice and incubated with anti-TREM2 antibodies (FIG. 7). Furthermore, DAP12 was found to be phosphorylated in wild-type macrophages incubated with the anti-TREM2 antibodies anti-TREM2 antibody #2 and anti-TREM2 antibody #3. A lower level of phosphorylated DAP12 co-precipitated with a control antibody γ2B. Conversely, no DAP12 co-precipitation or phosphorylation was observed in TREM2−/− macrophages incubated with antibodies anti-TREM2 antibody #2 and anti-TREM2 antibody #3 (FIG. 7). These results demonstrate that TREM2-associated DAP12 is phosphorylated when macrophages are incubated with anti-TREM2 antibodies, suggesting that TREM2-specific antibodies can activate TREM2 signaling in murine macrophages.

Consistent with the above results, DAP12 was observed to be phosphorylated, and co-precipitated with TREM2, in macrophages isolated from wild-type mice (WT-1 and WT-2) incubated with the anti-TREM2 antibody #2. Treatment with the IgG1 control antibody (MOPC21) and anti-TREM2 antibody #4 did not induce phosphorylation of DAP12 in cells from wild-type mice. Surprisingly, anti-TREM2 antibody anti-TREM2 antibody #4 was able to induce DAP12 phosphorylation in macrophages isolated from two different TREM transgenic mice (Bac-Tg1 and Bac-2).

Figures 8A, 8B:
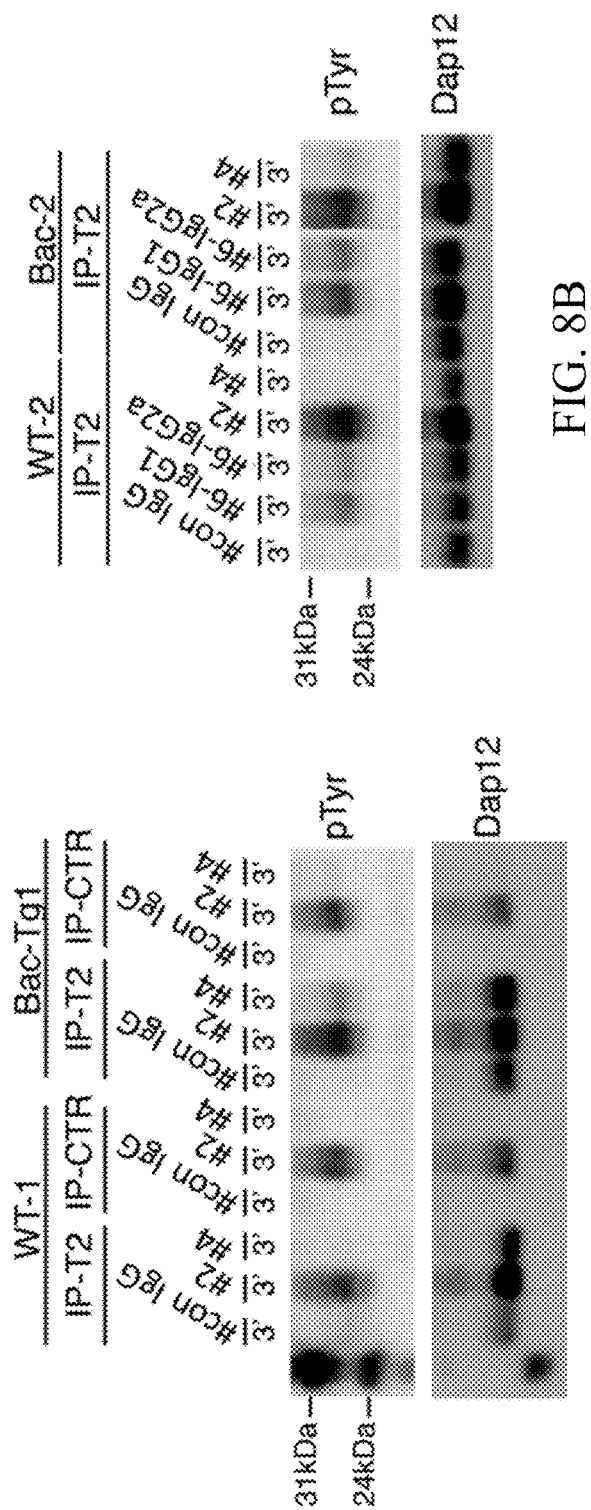
FIGS. 8A-8B show DAP12 phosphorylation in mouse macrophages incubated with anti-TREM2 or control antibodies.

Two additional TREM2 antibodies, anti-TREM2 antibody #6-IgG1, anti-TREM2 antibody #6-IgG2a, were tested (FIG. 8B). Surprisingly, both antibodies were able to induce DAP12 phosphorylation in wild-type macrophages (WT-2), as well as macrophages from the TREM transgenic mouse (Bac-2). This is in line with antibody #6 binding to both human and murine TREM2 as shown in FIG. 5.

Taken together, these results demonstrate that TREM2 antibodies such as anti-TREM2 antibody #2, anti-TREM2 antibody #4, anti-TREM2 antibody #6-IgG1, and anti-TREM2 antibody #6-IgG2a are able to induce DAP12 phosphorylation in macrophages derived from the TREM transgenic mice.

Example 6: Cell Viability Analysis of BMDMs Derived from TREM Transgenic Mice Upon TREM2 Antibody Stimulation Methodologies
Cell Viability Assay:
Anti-TREM2 antibodies were coated on a 96 well plate (10 μg/mL in PBS) at 4° C. overnight, and the wells were subsequently washed three times with PBS the following day. Day 5 BMDMs were plated into the wells and cultured for 2 days in the presence of 10 ng/mL mM-CSF.

Alternatively, to test the soluble format of TREM2 antibodies, Day 5 BMDMs or human dendritic cells (hDC) were plated in a 96 well plate. TREM2 antibodies were coated on plates in PBS or added solubly at 10 µg/mL in full media, and BMDMs or human dendritic cells were cultured for 2 days in the presence of 20 ng/mL mM-CSF. Cell viability was measured using CellTiter-Glo® Luminescent Cell Viability Assay (Promega, Madison, Wis.). The results were normalized to the respective isotype control groups.

Results

Figures 9A, 9B:
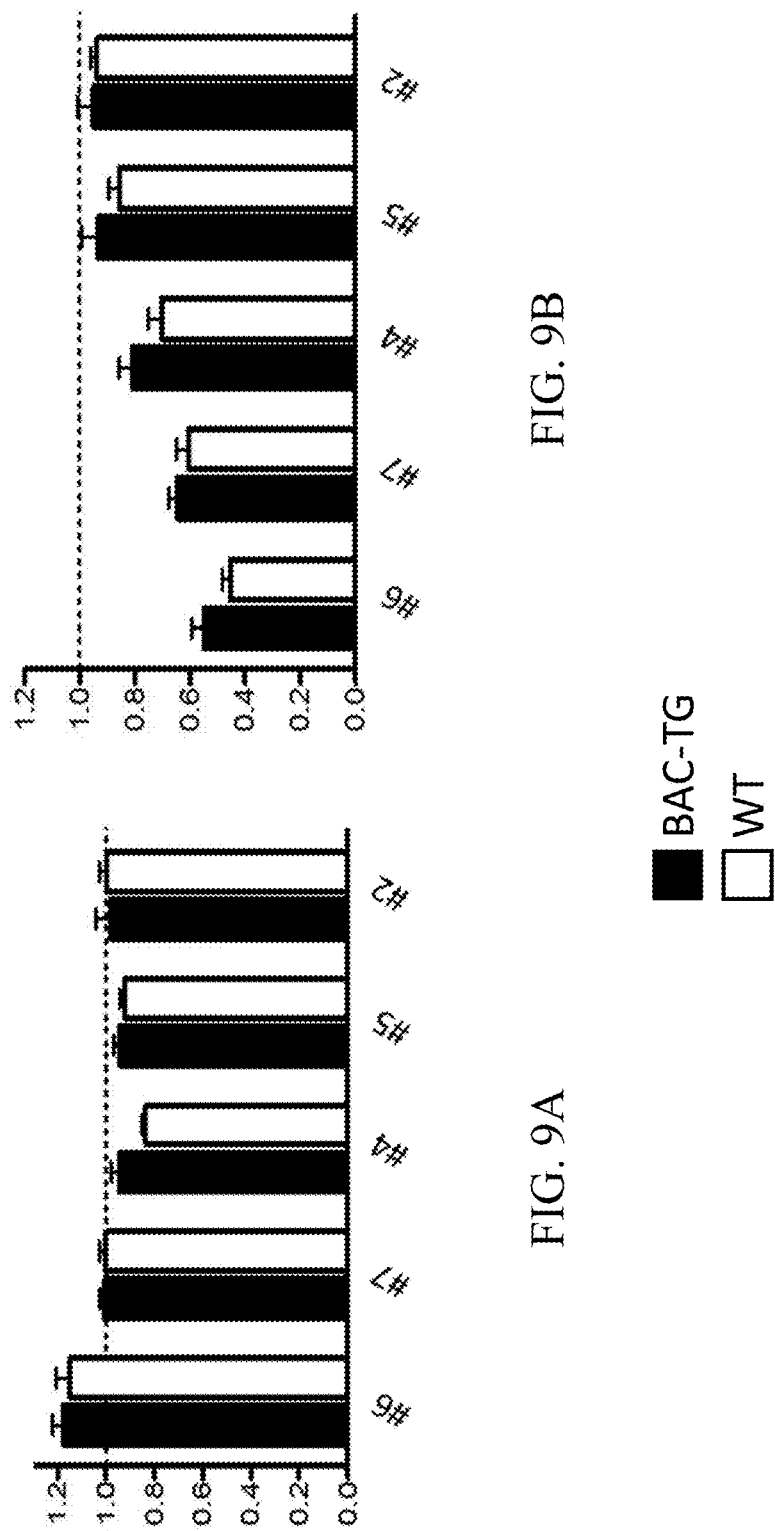
FIGS. 9A-9C show viability of the indicated cells after incubation with anti-TREM2 antibodies.
Figure 9C:
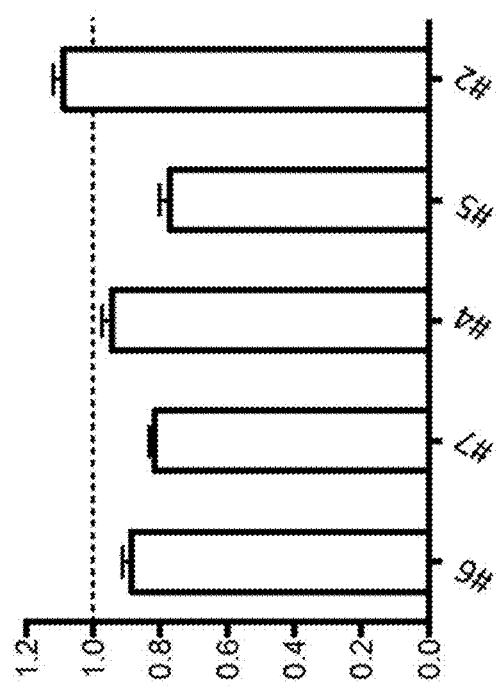

As shown in FIG. 9A, the plate-bound format of the anti-TREM2 antibodies #7 and #2 did not alter the viability of BMDMs isolated from wild-type or TREM transgenic mice (relative to the isotype control). Plate-bound anti-TREM2 antibody anti-TREM2 antibody #6 increased the viability of bone marrow-derived macrophages from wild-type and TREM transgenic mice relative to isotype control antibody (FIG. 9A, left lanes). Plate-bound anti-TREM2 antibodies anti-TREM2 antibody #4 and anti-TREM2 antibody #5 reduced the viability of BMDMs isolated from the TREM transgenic mice to approximately 0.9 and 0.8, respectively. Surprisingly, the soluble formats of anti-TREM2 antibodies anti-TREM2 antibody #6, anti-TREM2 antibody #7, and anti-TREM2 antibody #4 reduced the viability of both wild-type and TREM transgenic BMDMs (FIG. 9B). Soluble anti-TREM2 antibodies anti-TREM2 antibody #5 and anti-TREM2 antibody #2 did not appear to alter the viability of wild-type BMDMs, but slightly reduced the viability of BMDMs from the TREM transgenic mice (FIG. 9B). Additionally, soluble anti-TREM2 antibodies anti-TREM2 antibody #6, anti-TREM2 antibody #7, and anti-TREM2 antibody #5 also reduced the viability of human dendritic cells (FIG. 9C).

Figure 10:
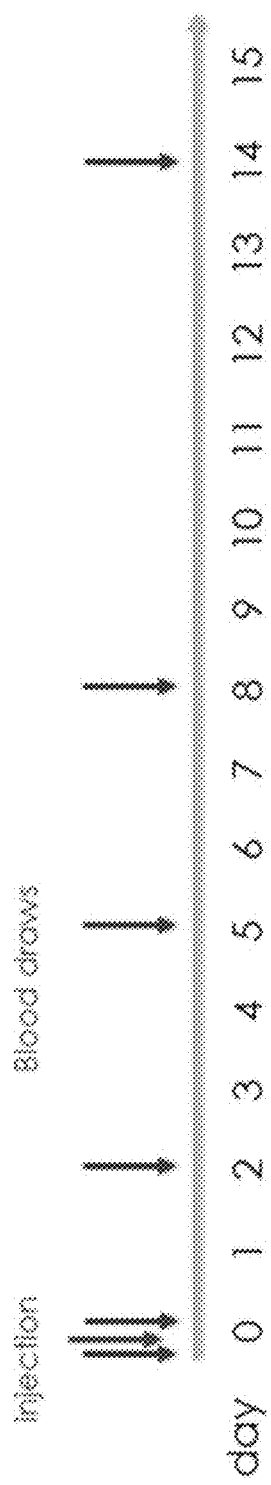
FIG. 10 shows the experimental design for analyzing the half-life of the anti-TREM2 antibodies anti-TREM2 antibody #6 and anti-TREM2 antibody #4 in vivo.

Example 7: Characterization of the Half-Life of TREM2 Antibodies in TREM Transgenic Mice Methodologies In Vivo Antibody Half-Life Assay:

As depicted in FIG. 10, anti-TREM2 antibody #6 and anti-TREM2 antibody #4, and the IgG1 control antibody, were injected into three groups of mice on day 0. Blood was obtained from each mouse on day 0, 2, 5, 8, and 14. Mice from two different Bac lines (#101, #257) were treated. The plasma IgG level in each blood sample was measured by ELISA assay according to standard techniques.

Results

Figure 11:
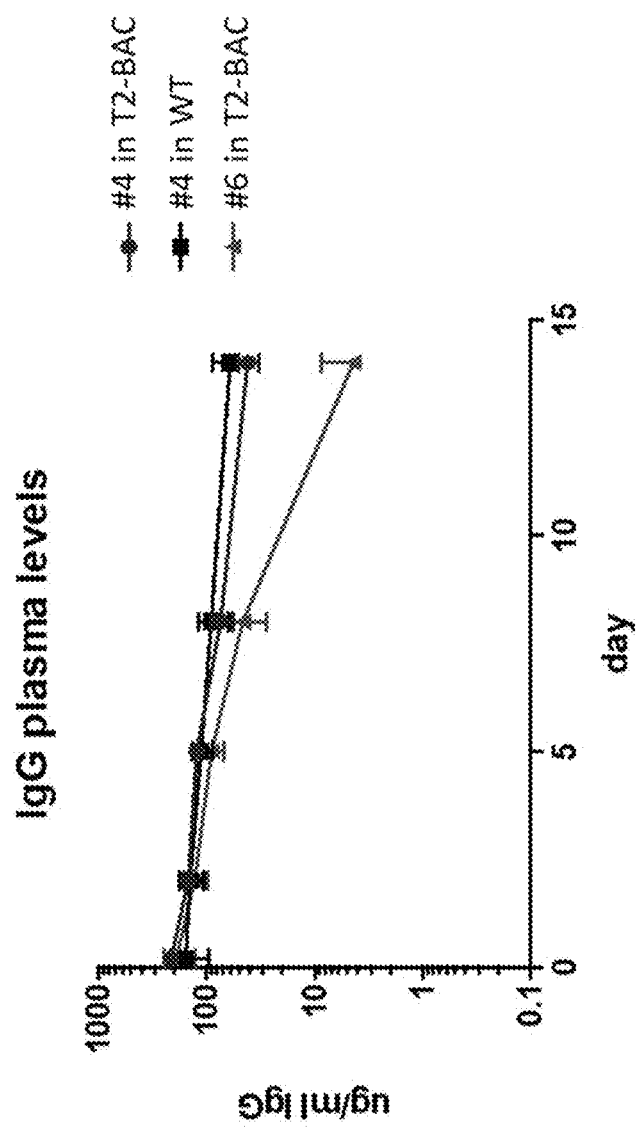
FIG. 11 shows the IgG plasma levels of anti-TREM2 antibodies anti-TREM2 antibody #6 and anti-TREM2 antibody #4 after injection into wild-type and CTD-3222A20 transgenic (BAC) mice.

As shown in Table 1 below, the in vivo half-life of the anti-TREM2 antibody anti-TREM2 antibody #4 in the TREM transgenic mice was 6.00 days, the half-life of anti-TREM2 antibody #4 in wild-type mice was 10.02 days, and the half-life of anti-TREM2 antibody #6 in the TREM transgenic mice was 2.59 days (FIG. 11). As shown in Table 1 and depicted in FIG. 11, the plasma level of the anti-TREM2 antibody #4 was consistently higher than the level of the anti-TREM2 antibody #6 in the TREM transgenic mice. The half-life of anti-TREM2 antibody #4 was slightly higher in the wild-type vs. TREM transgenic mice. Without wishing to be bound by theory, these results may be attributed to target-mediated degradation of anti-TREM2 antibody #4 in the presence of human TREM2 that is expressed in the transgenic mice.

TABLE 1 in vivo half-life of TREM2 antibodies anti-TREM2 antibody #6 and anti-TREM2 antibody #4

| mg/kg | Antibody anti-TREM2 antibody #4 in CTD-3222A20 transgenic mice | | | Antibody anti-TREM2 antibody #4 in wild-type mice | | | Antibody ADI anti-TREM2 antibody #6 in CTD-3222A20 transgenic mice | | |
|---|---|---|---|---|---|---|---|---|---|
| IgG Day | Average | Std Dev | CV | Average | Std Dev | CV | Average | Std Dev | CV |
| 0.2 | 212.84 | 83.84 | 39.39 | 156.37 | 83.84 | 53.62 | 191.15 | 83.84 | 43.86 |
| 2 | 148.65 | 40.73 | 27.40 | 142.37 | 40.73 | 28.61 | 129.59 | 40.73 | 31.43 |
| 5 | 123.48 | 116.80 | 94.59 | 112.40 | 116.80 | 103.91 | 90.00 | 116.80 | 129.77 |
| 8 | 74.34 | 35.29 | 47.47 | 90.73 | 35.29 | 38.89 | 46.10 | 35.29 | 76.54 |
| 14 | 41.93 | 35.29 | 84.16 | 61.16 | 35.29 | 57.69 | 4.39 | 35.29 | 803.67 |
| $t_{1/2}$ (days) | 6.00 | | | 10.02 | | | 2.59 | | |

Taken together, these results indicate that certain TREM2 antibodies, such as anti-TREM2 antibody #4, have a longer half-life relative to other TREM2 antibodies, such as anti-TREM2 antibody #6, in TREM transgenic mice.

Example 8: Analysis of Soluble TREM2 (sTREM2) Levels in TREM Transgenic Mice Methodologies Measurement of Soluble Plasma TREM2 Levels:

Soluble plasma levels of human and mouse TREM2 were measured in wild-type and TREM transgenic mice by ELISA assay according to standard techniques. Custom ELISAs were developed that can measure TREM2 tissue expression or sTREM2 in plasma or CSF that specifically detect human or mouse TREM2.

For the human specific TREM2 ELISA, capture antibody T2KO-8F11 (bin 2) was plated at 2 µg/ml in PBS overnight at 4 C (100 µL per well in high bind Elisa plates). The plates were washed thrice with a plate washer and 300 µL PBS+ 0.05% Triton per well. As a standard 156-10,000 pg/ml human TREM2–Fc (R&D Systems) was added to the plates, as well as diluted plasma or brain samples in binding buffer (PBS+1% BSA). Plates containing samples and standard were incubated at RT for 1 hour. The plates were washed thrice with a plate washer and 300 µL PBS+0.05% Triton per well. Biotinylated goat anti-human TREM2 polyclonal antibody (R&D Systems) was added at 1:2,000 dilution in binding buffer and incubated for 1 hour at RT. The plates were washed thrice with a plate washer and 300 µL PBS+

0.05% Triton per well. Streptavidin-HRP (1:200 in binding buffer, R&D Systems) was added to the plates and incubated for 20-30 minutes at RT. The plates were washed thrice with a plate washer and 300 μL PBS+0.05% Triton per well. 100 μL TMB substrate solution was added and incubated until color developed. The reaction was stopped by adding 50 μL of 2N sulfuric acid and the plate was read in a Synergy H1 plate reader at 450 and 630 nm.

The same general procedures were used for the mouse TREM2 specific ELISA with the following changes: capture antibody was T2KO-7E5 (2 μg/mL), the standard was mouse TREM2-Fc (R&D Systems) and the detection antibody rat anti-human/mouse TREM2 (R&D Systems, 1:5000). Data were analyzed in Excel and Graph Pad Prism.

In Vivo Administration of Anti-TREM2 Antibodies:

WT and TREM2 BAC Tg mice were injected on day 0 with 20 mg/kg 9F5 muIgG1 (n=4 BAC 257, n=4 WT), T21-9 muIgG1 (n=4 BAC 101) or control muIgG1 (n=2 BAC 101, n=2 BAC 257). The mice were a mix of two BAC strains (lines 101 and 257). These two BAC strains are derived from two different founders and they were characterized and shown to express high levels of human TREM2. Blood for plasma was collected in heparinized tubes one week prior to study initiation and on Days 0 (4 hrs after injections), 2, 5, 8 and 14. Plasma was isolated by spinning blood samples for 5 minutes at 5,000 rpm and collection of supernatant.

Results

Figure 12B:
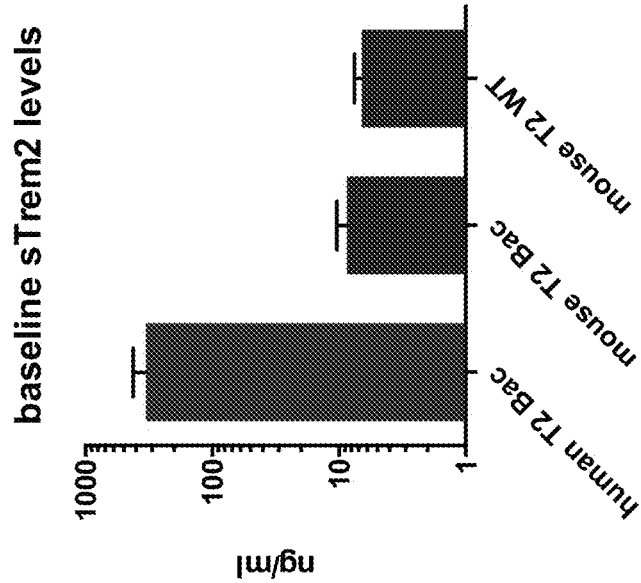
FIGS. 12A-12B show soluble TREM2 plasma levels quantified in samples from the indicated mouse lines.
Figure 12A:
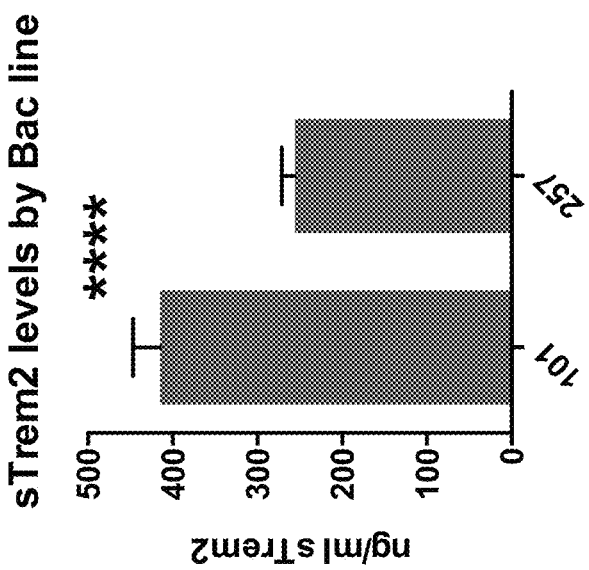

The serum levels of soluble mouse and human TREM2 were measured in wild-type and TREM transgenic mice. The transgenic mouse line Bac101 was found to have higher levels of soluble TREM2 as compared to the Bac257 mouse line (FIG. 12A). Furthermore, the levels of soluble mouse TREM2 in the plasma from Bac101 and wild-type mice were similar (FIG. 12B).

These results indicate that soluble human TREM2 can be detected in the plasma of the TREM transgenic mice and potentially used as a biomarker for antibodies or other reagents binding to and either activating TREM2 or blocking or increasing shedding of TREM2.

SEQUENCES

All polypeptide sequences are presented N-terminal to C-terminal unless otherwise noted.

Human TREM1 polypeptide-isoform 1
(SEQ ID NO: 1)
MRKTRLWGLLWMLFVSELRAATKLTEEKYELKEGQTLDVKCDYTLEKFAS

SQKAWQIIRDGEMPKTLACTERPSKNSHPVQVGRIILEDYHDHGLLRVRM

VNLQVEDSGLYQCVIYQPPKEPHMLFDRIRLVVTKGFSGTPGSNENSTQN

VYKIPPTTTKALCPLYTSPRTVTQAPPKSTADVSTPDSEINLTNVTDIIR

VPVFNIVILLAGGFLSKSLVFSVLFAVTLRSFVP

Human TREM1 polypeptide-isoform 2
(SEQ ID NO: 2)
MRKTRLWGLLWMLFVSELRAATKLTEEKYELKEGQTLDVKCDYTLEKFAS

SQKAWQIIRDGEMPKTLACTERPSKNSHPVQVGRIILEDYHDHGLLRVRM

VNLQVEDSGLYQCVIYQPPKEPHMLFDRIRLVVTKGFRCSTLSFSWLVDS

Human TREM1 polypeptide-isoform 3
SEQ ID NO: 3)
MRKTRLWGLLWMLFVSELRAATKLTEEKYELKEGQTLDVKCDYTLEKFAS

SQKAWQIIRDGEMPKTLACTERPSKNSHPVQVGRIILEDYHDHGLLRVRM

VNLQVEDSGLYQCVIYQPPKEPHMLFDRIRLVVTKGFSGTPGSNENSTQN

VYKIPPTTTKALCPLYTSPRTVTQAPPKSTADVSTPDSEINLTNVTDIIR

YSFQVPGPLVWTLSPLFPSLCAERM

Human TREML1 polypeptide-isoform a
(SEQ ID NO: 4)
MGLTLLLLLLLGLEGQGIVGSLPEVLQAPVGSSILVQCHYRLQDVKAQKV

WCRFLPEGCQPLVSSAVDRRAPAGRRTFLTDLGGGLLQVEMVTLQEEDAG

EYGCMVDGARGPQILHRVSLNILPPEEEEETHKIGSLAENAFSDPAGSAN

PLEPSQDEKSIPLIWGAVLLVGLLVAAVVLFAVMAKRKQGNRLGVCGRFL

SSRVSGMNPSSVVHHVSDSGPAAELPLDVPHIRLDSPPSFDNTTYTSLPL

DSPSGKPSLPAPSSLPPLPPKVLVCSKPVTYATVIFPGGNKGGGTSCGPA

QNPPNNQTPSS

Human TREML1 polypeptide-isoform b
(SEQ ID NO: 5)
MGLTLLLLLLLGLEGQGIVGSLPEVLQAPVGSSILVQCHYRLQDVKAQKV

WCRFLPEGCQPLVSSAVDRRAPAGRRTFLTDLGGGLLQVEMVTLQEEDAG

EYGCMVDGARGPQILHRVSLNILPPEEEEETHKIGSLAENAFSDPAGSAN

PLEPSQDEKSIPLIWGAVLLVGLLVAAVVLFAVMAKRKQESLLSGPPRQ

Human TREML1 polypeptide-isoform c
(SEQ ID NO: 6)
MGLTLLULLLGLEEEEETHKIGSLAENAFSDPAGSANPLEPSQDEKSIP

LIWGAVLLVGLLVAAVVLFAVMAKRKQGNRLGVCGRFLSSRVSGMNPSSV

VHHVSDSGPAAELPLDVPHIRLDSPPSFDNTTYTSLPLDSPSGKPSLPAP

SSLPPLPPKVLVCSKPVTYATVIFPGGNKGGGTSCGPAQNPPNNQTPSS

Human TREM2 polypeptide-isoform 1
(SEQ ID NO: 7)
MEPLRLLILLFVTELSGAHNTTVFQGVAGQSLQVSCPYDSMIKHWGRRKA

WCRQLGEKGPCQRVVSTHNLWLLSFLRRWNGSTAITDDTLGGTLTITLRN

LQPHDAGLYQCQSLHGSEADTLRKVLVEVLADPLDHRDAGDLWFPGESES

FEDAHVEHSISRSLLEGEIPFPPTSILLLLACIFLIKILAASALWAAAWH

GQKPGTHPPSELDCGHDPGYQLQTLPGLRDT

Human TREM2 polypeptide-isoform 2
(SEQ ID NO: 8)
MEPLRLLILLFVTELSGAHNTTVFQGVAGQSLQVSCPYDSMIKHWGRRKA

WCRQLGEKGPCQRVVSTHNLWLLSFLRRWNGSTAITDDTLGGTLTITLRN

LQPHDAGLYQCQSLHGSEADTLRKVLVEVLADPLDHRDAGDLWFPGESES

FEDAHVEHSISRAERHVKEDDGRKSPGEVPPGTSPACILATWPPGLLVLL

WQETTLPEHCFSWTLEAGTG

Human TREM2 polypeptide-isoform 3
(SEQ ID NO: 9)
MEPLRLLILLFVTELSGAHNTTVFQGVAGQSLQVSCPYDSMIKHWGRRKA

WCRQLGEKGPCQRVVSTHNLWLLSFLRRWNGSTAITDDTLGGTLTITLRN

LQPHDAGLYQCQSLHGSEADTLRKVLVEVLADPLDHRDAGDLWFPGESES

FEDAHVEHSISRPSQGSHLPSCLSKEPLGRRNPLPTHFHPSPPGLHLSHQ

DSSSQRPLGCSLAWTEARDTSTQ

-continued

Human TREML2 polypeptide
(SEQ ID NO: 10)

MAPAFLLLLLLWPQGCVSGPSADSVYTKVRLLEGETLSVQCSYKGYKNRV

EGKVWCKIRKKKCEPGFARVWVKGPRYLLQDDAQAKVVNITMVALKLQDS

GRYWCMRNTSGILYPLMGFQLDVSPAPQTERNIPFTHLDNILKSGTVTTG

QAPTSGPDAPFTTGVMVFTPGLITLPRLLASTRPASKTGYSFTATSTTSQ

GPRRTMGSQTVTASPSNARDSSAGPESISTKSGDLSTRSPTTGLCLTSRS

LLNRLPSMPSIRHQDVYSTVLGVVLTLLVLMLIMVYGFWKKRHMASYSMC

SDPSTRDPPGRPEPYVEVYLI

Human TREML4 polypeptide
(SEQ ID NO: 11)

MAWGGVHTCCFHLCCCCSWPQGAVPEELHKHPGQTLLLQCQYSPKRGPYQ

PKSWCQQTSPSRCTLLVTSSKPWTAVQKSHYTIWDKPNAGFFNITMIQLT

QNDSGFYWCGIYNASENIITVLRNISLVVSPAPTTSPMWTLPWLPTSTVL

ITSPEGTSGHPSINGSETRKSRAPACLGSGGPRFLVLVLCGLLLAKGLML

---

What is claimed is:

1. A transgenic non-human animal whose genome comprises human genes present on a bacterial artificial chromosome comprising the endogenous human transcriptional regulatory elements of the human genes,
wherein the transgenic non-human animal is a mouse,
wherein the human genes are Triggering receptor expressed on myeloid cells 1 (TREM1), Triggering receptor expressed on myeloid cells-like protein 1 (TREML1), and Triggering receptor expressed on myeloid cells 2 (TREM2),
wherein the human TREM1, TREML1 or TREM2 genes are expressed in peripheral and/or bone-marrow-derived macrophages of the transgenic non-human animal.

2. The transgenic non-human animal of claim 1, wherein the human TREM1 gene encodes a polypeptide at least 95% identical to a sequence selected from the group consisting of SEQ ID NOS: 1-3.

3. The transgenic non-human animal of claim 1, wherein the human TREML1 gene encodes a polypeptide at least 95% identical to a sequence selected from the group consisting of SEQ ID NOS: 4-6.

4. The transgenic non-human animal of claim 1, wherein the human TREM2 gene encodes a polypeptide at least 95% identical to a sequence selected from the group consisting of SEQ ID NOS: 7-9.

5. The transgenic non-human animal of claim 1, wherein expression of the human TREM1, TREML1 or TREM2 genes in peripheral and/or bone-marrow-derived macrophages of the transgenic non-human animal recapitulates the expression pattern of the human TREM1, TREML1 or TREM2 genes in a corresponding human cell.

6. The transgenic non-human animal of claim 1, wherein the peripheral or bone-marrow-derived macrophages have one or more macrophage functions selected from the group consisting of:

(a) phagocytosis;
(b) antigen presentation;
(c) immune cell recruitment;
(d) immune cell maturation, migration, proliferation, differentiation, and/or survival;
(e) modulation of adaptive immune cells;
(f) expression and/or secretion of one or more cytokines and/or chemokines produced by macrophages or microglia;
(g) tumor infiltration, tumor cell recognition, and/or tumor cell killing;
(h) anti-parasitic activities;
(i) bactericidal activities;
(j) clearance of cellular debris and/or protein aggregates; and
(k) any combinations thereof.

7. The transgenic non-human animal of claim 1, wherein the transgenic non-human animal has been bred with a disease model non-human animal, and wherein the disease model non-human animal is a mouse.

8. The transgenic non-human animal of claim 7, wherein the disease model non-human animal is a model of one or more diseases selected from the group consisting of neurodegenerative diseases, immune-related diseases, infectious diseases, and proliferative disorders.

9. The transgenic non-human animal of claim 7, wherein the disease model non-human animal is a model of one or more diseases selected from the group consisting of dementia, frontotemporal dementia (FTD), Alzheimer's disease, Parkinson's disease, amyotrophic lateral sclerosis (ALS), Huntington's disease, taupathy disease, Nasu-Hakola disease, and multiple sclerosis.

10. The transgenic non-human animal of claim 1, wherein the transgenic non-human animal comprises an antibody that binds to human TREM2.

* * * * *